United States Patent
Kano et al.

(10) Patent No.: US 10,206,587 B2
(45) Date of Patent: Feb. 19, 2019

(54) IMAGE PROCESSING APPARATUS, IMAGE PROCESSING METHOD, AND STORAGE MEDIUM

(71) Applicant: Toshiba Medical Systems Corporation, Otawara-shi (JP)

(72) Inventors: Akira Kano, Kawasaki (JP); Kenji Hirohata, Kouto (JP); Junichiro Ooga, Kawasaki (JP); Mitsuaki Kato, Kawasaki (JP); Takuya Hongo, Yokohama (JP); Akihiro Goryu, Kawasaki (JP); Shigeo Kaminaga, Otawara (JP); Yasuko Fujisawa, Nasushiobara (JP); Satoshi Wakai, Nasushiobara (JP); Yoshihiro Ikeda, Sakura (JP); Kazumasa Arakita, Nasushiobara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 15/344,159

(22) Filed: Nov. 4, 2016

(65) Prior Publication Data

US 2017/0071479 A1 Mar. 16, 2017

Related U.S. Application Data

(63) Continuation-in-part of application No. 14/713,364, filed on May 15, 2015.

(30) Foreign Application Priority Data

May 16, 2014 (JP) .................................. 2014-102818
May 16, 2014 (JP) .................................. 2014-102830

(Continued)

(51) Int. Cl.
*A61B 5/05* (2006.01)
*A61B 5/02* (2006.01)
(Continued)

(52) U.S. Cl.
CPC ........ *A61B 5/02007* (2013.01); *A61B 5/0044* (2013.01); *A61B 5/02* (2013.01);
(Continued)

(58) Field of Classification Search
None
See application file for complete search history.

(56) References Cited

U.S. PATENT DOCUMENTS 6,117,087 A * 9/2000 Kamm .................. A61B 5/021
600/481
6,471,656 B1 * 10/2002 Shalman .............. A61B 5/0215
600/486

(Continued)

FOREIGN PATENT DOCUMENTS

JP 2008-241432 A 10/2008
JP 2009-195586 A 9/2009

OTHER PUBLICATIONS

Khalid (The effect of Doppler phenomenon on the speed of blood flow).*

(Continued)

*Primary Examiner* — Joel F Brutus
(74) *Attorney, Agent, or Firm* — Oblon, McClelland, Maier & Neustadt, L.L.P.

(57) ABSTRACT

An image processing apparatus according to an embodiment includes a processing circuitry. The processing circuitry is configured to obtain images in a time series including images of a blood vessel of a subject and correlation information indicating a correlational relationship between physical indices of the blood vessel and function indices of (Continued)

the blood vessel related to vascular hemodynamics, calculate blood vessel morphology indices in a time series indicating morphology of the blood vessel of the subject, on a basis of the images in the time series, and identify a function index of the blood vessel of the subject, by using a physical index of the blood vessel of the subject obtained from the blood vessel morphology indices, on a basis of the correlation information.

28 Claims, 22 Drawing Sheets

(30) Foreign Application Priority Data

May 16, 2014 (JP) ................................. 2014-102901
May 15, 2015 (JP) ................................. 2015-100453

(51) Int. Cl.
| | | |
|---|---|---|
| A61B 5/00 | (2006.01) | |
| A61B 5/026 | (2006.01) | |
| A61B 5/055 | (2006.01) | |
| A61B 5/107 | (2006.01) | |
| A61B 34/00 | (2016.01) | |
| A61B 5/044 | (2006.01) | |

(52) U.S. Cl.
CPC ............ *A61B 5/026* (2013.01); *A61B 5/0263* (2013.01); *A61B 5/055* (2013.01); *A61B 5/107* (2013.01); *A61B 5/1075* (2013.01); *A61B 34/00* (2016.02); *A61B 5/044* (2013.01); *A61B 5/1079* (2013.01); *A61B 5/7246* (2013.01); *A61B 5/7278* (2013.01); *A61B 5/748* (2013.01); *A61B 2576/00* (2013.01)

(56) References Cited

U.S. PATENT DOCUMENTS

| | | | |
|---|---|---|---|
| 7,653,510 B2 | 1/2010 | Hirohata et al. | |
| 2009/0238424 A1* | 9/2009 | Arakita ................. | A61B 6/032 382/128 |
| 2012/0022350 A1* | 1/2012 | Teixeira ............... | A61B 5/0205 600/324 |
| 2012/0041318 A1* | 2/2012 | Taylor ................ | A61B 5/02007 600/504 |
| 2012/0243761 A1* | 9/2012 | Senzig ................. | G06T 11/008 382/131 |
| 2014/0088414 A1* | 3/2014 | Mittal .................... | A61B 6/481 600/425 |

OTHER PUBLICATIONS

Kadooka Yoshimasa, "Heart Simulation Leading to Tailor-Made Treatment—Introduction of the world's most advanced heart simulator and its application—", ITU Journal, vol. 41, No. 6, 2011, pp. 41-44.

James K. Min et al., "Rationale and design of the DeFACTO (Determination of Fractional Flow Reserve by Anatomic Computed Tomographic AngiOgraphy) study", Journal of Cardiovascular Computed Tomography, 2011, vol. 5, pp. 301-309.

U.S Office Action dated Feb. 27, 2017 in U.S. Appl. No. 14/713,364.

\* cited by examiner

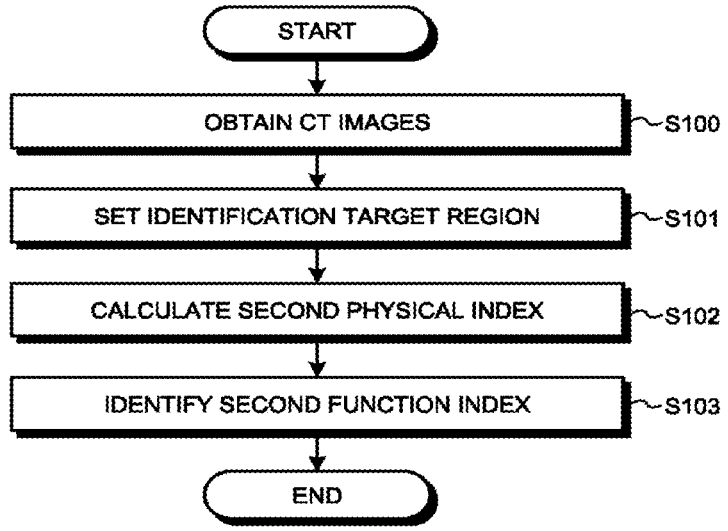
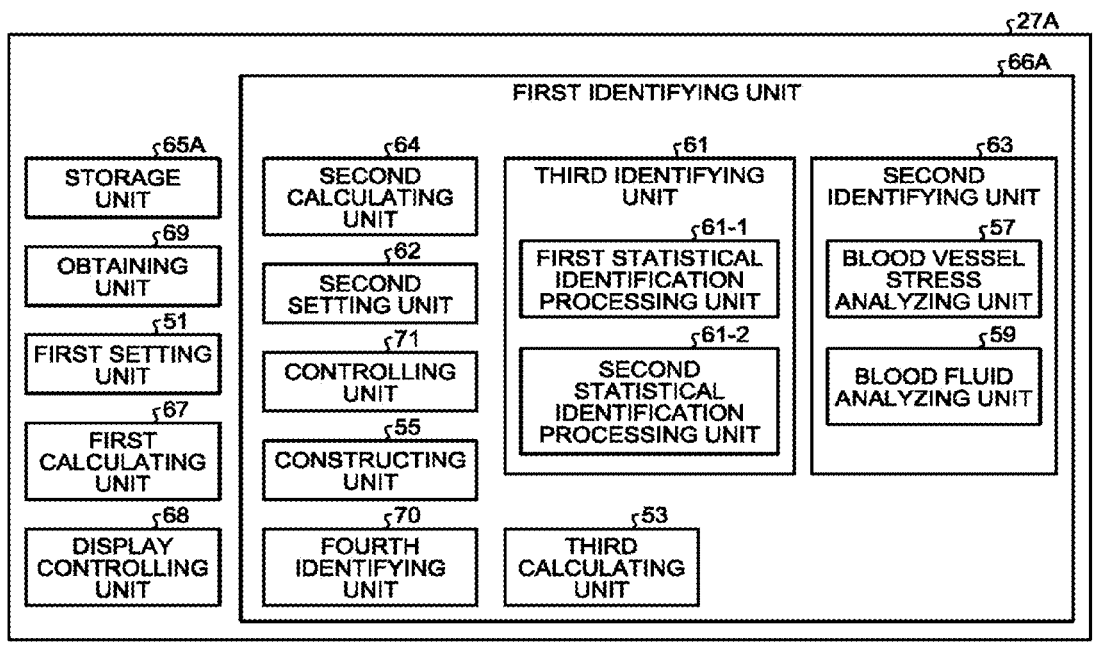

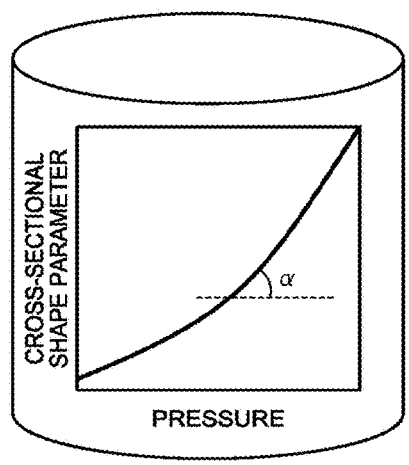 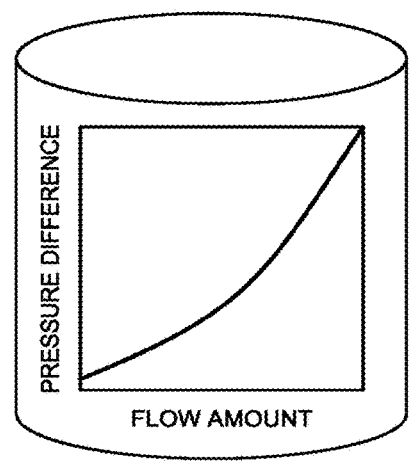

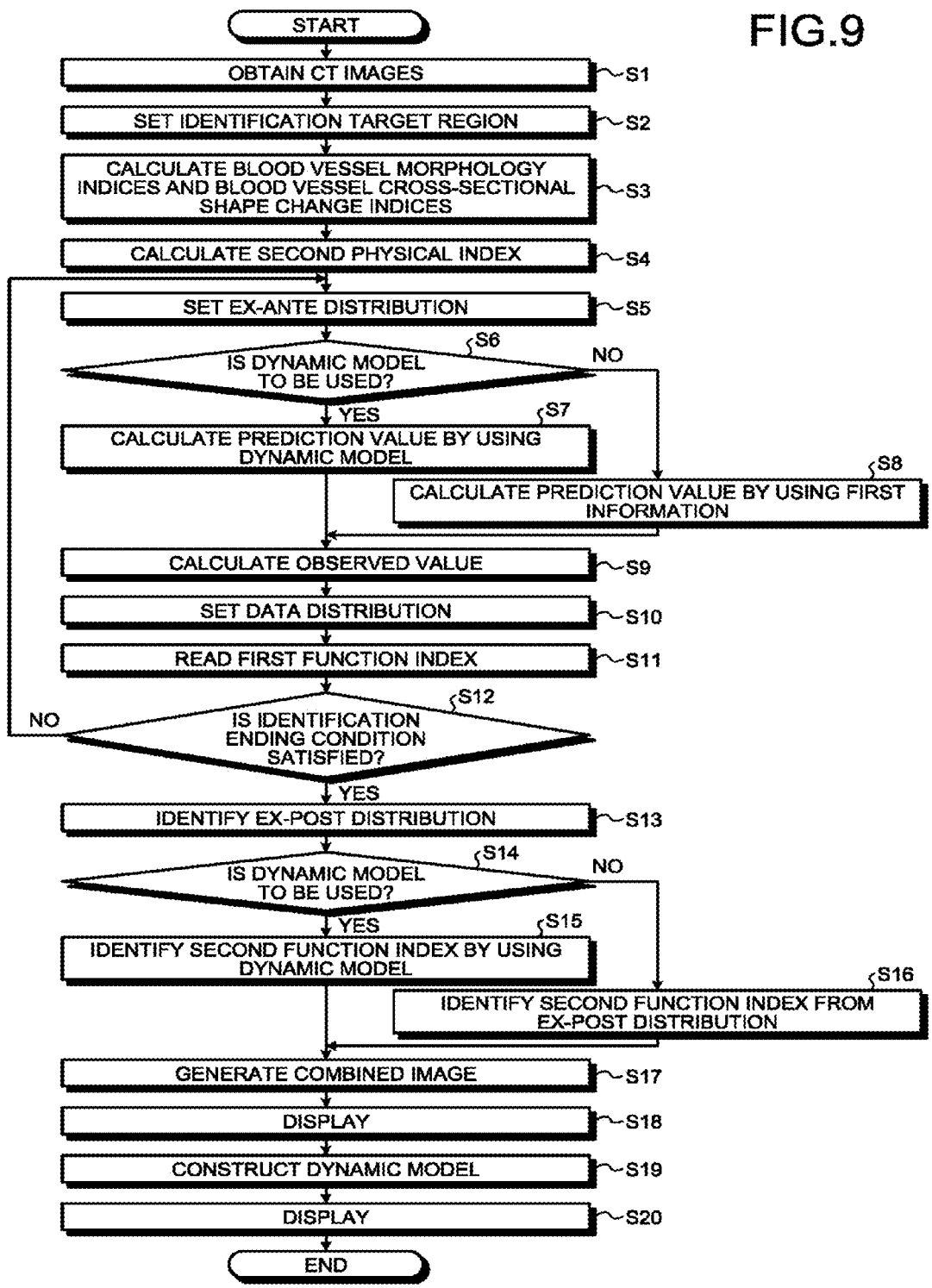

IMAGE PROCESSING APPARATUS, IMAGE PROCESSING METHOD, AND STORAGE MEDIUM

CROSS-REFERENCE TO RELATED APPLICATIONS

This application is a continuation-in-part (CIP) of application Ser. No. 14/713,364 filed May 15, 2015, the entire contents of which are incorporated herein by reference. This application is also based upon and claims the benefit of priority from Japanese Patent Applications No. 2014-102818, No. 2014-102830, No. 2014-102901, each filed on May 16, 2014; and Japanese Patent Application No. 2015-100453, filed on May 15, 2015, the entire contents of all of which are incorporated herein by reference.

FIELD

Embodiments described herein relate generally to an image processing apparatus, an image processing method, and a storage medium.

BACKGROUND

Causes of ischemic diseases of an organ can be roughly divided into hemodynamic failure and function failure of the organ itself. For the situations where the cause is hemodynamic failure, it is in demand to provide an evaluation index that can suggest a treatment method in a non-invasive manner and a technique that can be used in diagnosis processes.

For example, stenosis, which is an example of hemodynamic failure in coronary arteries, is a serious pathological issue that may lead to an ischemic heart disease. Ischemic heart diseases require to determine whether a drug treatment should be performed or a stent treatment should be performed, or the like. As a diagnosis method for evaluating hematogenous ischemia of coronary arteries, a recommended method in recent years has been a method by which a Fractional Flow Reserve (FFR) value is measured while using a wire guide, by performing a coronary angiography (CAG) examination that employs a catheter.

In this situation, for example, there is a possibility that the need to perform the catheter surgery may be eliminated, if it is possible to evaluate homogenous ischemia of coronary arteries, by using an X-ray Computed Tomography image (hereinafter, simply "CT image"), a Magnetic Resonance Angiography (MRA) image, or an ultrasound image of the heart.

BRIEF DESCRIPTION OF THE DRAWINGS

FIG. 6 is a flowchart of a flow in a blood vessel analyzing process;

FIG. 7 is a functional block diagram of another image processing apparatus;

FIGS. 8A and 8B are drawings of examples of first information and second information;

FIG. 9 is a flowchart of a flow in a blood vessel analyzing process;

DETAILED DESCRIPTION

Figure 1:
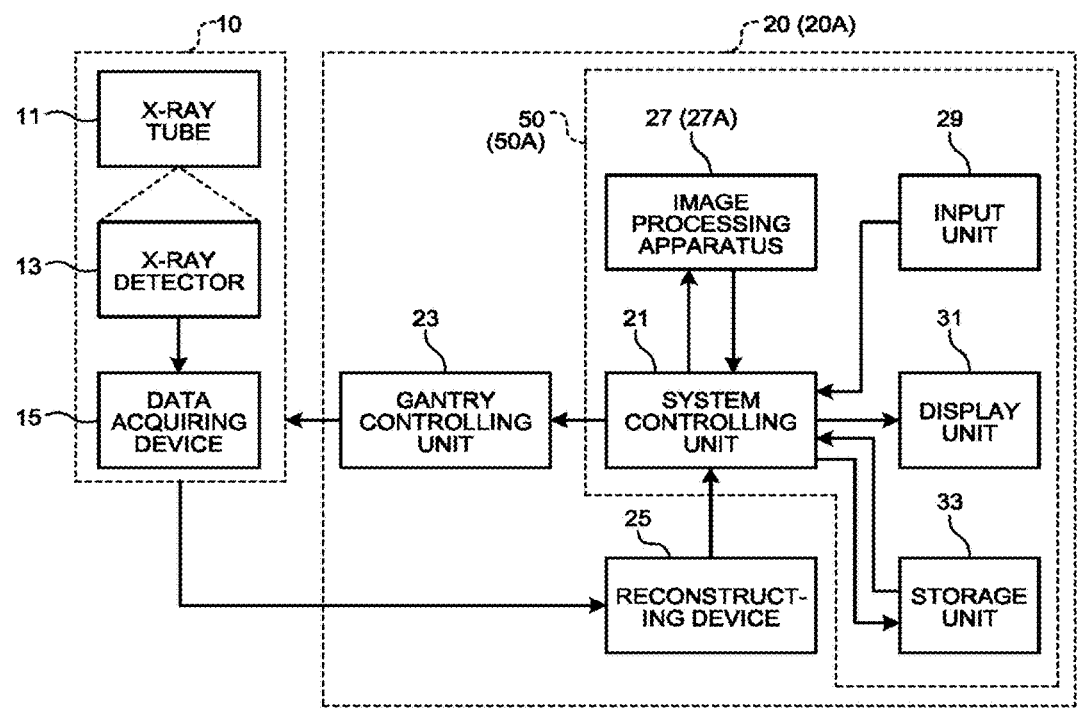
FIG. 1 is a hardware diagram of a medical image diagnosis apparatus.

Exemplary embodiments of an image processing apparatus, an image processing method, and a storage medium will be explained in detail below, with reference to the accompanying drawings.

An image processing apparatus according to an embodiment includes a processing circuitry. The processing circuitry is configured to obtain images in a time series including images of a blood vessel of a subject and correlation information indicating a correlational relationship between physical indices of the blood vessel and function indices of the blood vessel related to vascular hemodynamics, calculate blood vessel morphology indices in a time series indicating morphology of the blood vessel of the subject, on a basis of the images in the time series, and identify a function index of the blood vessel of the subject, by using a physical index of the blood vessel of the subject obtained from the blood vessel morphology indices, on a basis of the correlation information.

First Embodiment

To begin with, a first embodiment will be explained.

An image processing apparatus according to the first embodiment is configured to calculate a physical index of an identification target region from blood vessel morphology indices calculated on the basis of images in a time series and to identify a function index of a blood vessel of a subject on the basis of correlation information and the calculated physical index. In this situation, for example, the correlation information may be a database (DB) or a table in which physical indices and function indices are kept in correspondence with one another or may be a statistical model, a stochastic model, a mathematical model, or the like.

With this configuration, by identifying the function index of the blood vessel of the subject serving as an identification target, on the basis of the images in the time series including images of the blood vessel of the subject, it is possible to identify the function index of the blood vessel in a non-invasive manner. Further, by identifying the function index of the blood vessel of the subject serving as the identification target on the basis of the correlation information indicating a correlational relationship between the physical indices and the function indices of the blood vessel, it is possible to identify the function index of the blood vessel at a high speed.

A blood vessel analyzing apparatus, a blood vessel analyzing method, and a storage medium according to the first embodiment are applicable to a computer apparatus used for analyzing a blood vessel region included in images generated by an image diagnosis apparatus. In the first embodiment, an example will be explained in which medical images are used as the images. The computer apparatus may be incorporated in the medical image diagnosis apparatus or may be configured with a workstation or the like that is separate from the medical image diagnosis apparatus. In the following sections, a medical image diagnosis apparatus that has incorporated therein the computer apparatus to which the blood vessel analyzing apparatus and the blood vessel analyzing method according to the first embodiment are applied will be explained in detail, with reference to the accompanying drawings.

The medical image diagnosis apparatus according to the first embodiment is able to take, as an analysis target thereof, a blood vessel in any site of a human body, such as a cardiac blood vessel, a carotid artery, or a cerebral artery. In the following sections, the explanation will be continued with an example in which a cardiac blood vessel is used as an analysis target.

Examples of cardiac blood vessels include the coronary arteries and the aorta. The coronary arteries start from the coronary artery starting part of the aorta and run over the surface of the myocardia so as to extend from the epicardium side into the endocardium side. The coronary arteries branch into numerous capillary vessels at the inner layers of the myocardia. After the branching, the numerous capillary vessels are integrated together again so as to form the great cardiac vein, which connects to the coronary sinus. The coronary blood vessel system is distinctive in that, unlike other organs, perfusion needs to be guaranteed through dynamic changes caused by contraction and relaxation of the myocardia.

A characteristic of the coronary blood flow lies in that the flowing amount is larger when the perfusion pressure becomes lower during a left ventricle expansion period than during a contraction period when the internal pressure at the coronary artery starting part becomes higher due to a mechanical blood flow obstruction action caused by the contraction of the myocardia. For this reason, a normal coronary artery blood flow-rate waveform exhibits two peaks during the contraction period and the expansion period, and the blood flow in the expansion period is predominant. It is known that distinctive blood flow waveforms can be observed with some diseases. For example, with hypertrophic cardiomyopathy or aortic valve stenosis, retrograde waves can be observed during a contraction period. With aortic regurgitation, prograde waves during contraction periods may be larger. Further, prograde waveforms during expansion periods are closely related to the left ventricle expanding function, in particular, the left ventricle relaxation. In an example of a delay in the left ventricle relaxation, there is a tendency that peaks in the waveform in expansion periods are shifted to later times and that the degree of deceleration becomes gradual. Further, with those medical cases, it is considered that the coronary blood flow amounts during expansion periods do not sufficiently increase if tachycardia is present and that myocardial ischemia may thus be promoted.

Anatomically speaking, the coronary blood flow is generated as a result of coronary perfusion pressure (i.e., the pressure at the aorta starting part where the coronary arteries branch) being applied to the left and right coronary arteries branching from the aorta starting part, the coronary perfusion pressure being equal to aorta pressure. Important elements that determine the coronary blood flow are the driving pressure, which is the aortic pressure, as well as a coronary blood vessel resistance. It is known that approximately 20% of the coronary blood vessel resistance is present in coronary blood vessels having a large diameter of 140 μm to 180 μm or larger, whereas a large portion of the rest of the resistance components is present in microvasculature of 100 μm to 150 μm or smaller. Accordingly, the resistance value is dependent on tonus of coronary microvasculature, unless what is called a coronary stenosis or the like is present.

Blood vessel resistance factors include blood vessel characteristics, arteriosclerosis, vascular stenosis, blood viscosity, and mechanical factors. The tonus of the coronary microvasculature is defined by blood vessel characteristics, myocardial metabolism (myocardial oxygen consumption), neurohumoral factors, mechanical factors, and various types of blood vessel operational substances and the blood viscosity that serve as humoral factors. Further, the tonus of the coronary microvasculature is also affected by various pathological issues such as cardiac hypertrophy and coronary sclerosis and may lead to a coronary circulatory disorder.

The pulsatile movement of the blood flows in the coronary arteries is affected by pulsatile movement patterns of the coronary blood flows, control of intramyocardial blood flows caused by the myocardial contraction, and responses of intramyocardial blood vessels to mechanical stimulations. Examples of mechanisms where a blood flow is obstructed by the myocardial contraction include an increase in myocardial internal pressure, changes in the volume of the intramyocardial blood vessels, and compressions of the intramyocardial blood vessels. Factors that define the blood flow in myocardial expansion periods include the coronary artery pressure during expansion periods, extravascular forces during expansion periods, heart rate, the percentage of expansion periods in the cardiac cycle, and myocardial relaxation.

The medical image diagnosis apparatus according to the first embodiment is applicable to any type of medical image diagnosis apparatus provided with an imaging mechanism used for scanning a subject. For example, the medical image diagnosis apparatus according to the first embodiment may be used for, as appropriate, X-ray computed tomography apparatuses (X-ray CT apparatuses), magnetic resonance diagnosis apparatuses, ultrasound diagnosis apparatuses, Single Photon Emission CT (SPECT) apparatuses, Positron Emission Tomography (PET) apparatuses, and radiation treatment apparatuses. To provide specific explanations below, the medical image diagnosis apparatus according to the first embodiment is assumed to be an X-ray computed tomography apparatus.

FIG. 1 is a schematic hardware diagram of a medical image diagnosis apparatus (an X-ray computed tomography apparatus) according to the first embodiment. As illustrated in FIG. 1, the X-ray computed tomography apparatus includes a CT gantry 10 and a console 20. The CT gantry 10 is configured, under control of a gantry controlling unit 23 included in the console 20, to perform a scan on an imaging target site of a subject while using X-rays. The imaging target site may be the heart, for example.

The CT gantry 10 includes an X-ray tube 11, an X-ray detector 13, and a data acquiring device 15. The X-ray tube 11 and the X-ray detector 13 are installed with the CT gantry 10 so as to be rotatable on a rotation axis Z. The X-ray tube 11 is configured to radiate the X-rays onto the subject into whom a contrast agent has been injected. The X-ray detector 13 is configured to detect X-rays that were generated by the X-ray tube 11 and have passed through the subject and to generate electrical signals corresponding to the intensities of the detected X-rays.

The data acquiring device 15 is configured to read the electrical signals from the X-ray detector 13 and to convert the read electrical signals into digital data. A set of digital data corresponding to one view is called a raw data set. Raw data sets that are in time series and are related to a plurality of scanning times are transferred to the console 20 by a non-contact data transfer device (not illustrated).

The console 20 has a system controlling unit 21 serving as a hub and includes the gantry controlling unit 23, a reconstructing device 25, and a blood vessel analyzing apparatus 50.

The gantry controlling unit 23 is configured to control devices provided in the console 20 in accordance with a scan condition that is set by a user via an input unit 29.

The reconstructing device 25 is configured to generate data of CT images related to the subject on the basis of the raw data sets. More specifically, first, the reconstructing device 25 generates projection data sets by performing a pre-processing process on the raw data sets. Examples of the pre-processing processes include a logarithmic conversion, a non-uniformity correction, and a calibration correction. Subsequently, the reconstructing device 25 generates the CT images by performing an image reconstructing process on the projection data sets. As an algorithm used for reconstructing the images, it is possible to use any of existing algorithms, such as analytic image reconstruction methods that implement a Filtered BackProjection (FBP) method or the like and successive approximation image reconstruction methods that implement a Maximum Likelihood Expectation Maximization (ML-EM) method, an Ordered Subset Expectation Maximization (OS-EM) method, or the like.

The reconstructing device 25 generates the CT images in a time series, on the basis of the projection data sets in the time series. The CT images include pixel regions (hereinafter, "blood vessel regions") related to blood vessels of which the contrast is enhanced by the contrast agent. The CT images may be represented by slice data expressing a two-dimensional spatial distribution of the CT values or may be represented by volume data expressing a three-dimensional spatial distribution of the CT values. In the following explanation, the CT images are assumed to be represented by volume data. The CT images in the time series ate stored in a storage unit 33 and a storage unit 65 included in an image processing apparatus 27 (explained later).

The blood vessel analyzing apparatus 50 is an apparatus configured to perform a blood vessel analysis. The blood vessel analyzing apparatus 50 includes a system controlling unit 21, the image processing apparatus 27, the input unit 29, a display unit 31, and the storage unit 33.

The blood vessel analyzing apparatus 50 may be incorporated in the medical image diagnosis apparatus (the X-ray computed tomography apparatus) or may be a computer apparatus separate from the medical image diagnosis apparatus. If the blood vessel analyzing apparatus 50 is separate from the medical image diagnosis apparatus, the blood vessel analyzing apparatus 50 may acquire medical images such as the CT images in the time series from the medical image diagnosis apparatus or a Picture Archiving and Communication System (PACS) via a network.

The input unit 29 is configured to receive inputs of various types of commands and information from the user. As the input unit 29, a keyboard, a mouse, and/or a switch may be used.

The display unit 31 is configured to display the CT images and various types of information such as analysis results. As the display unit 31, for example, a Cathode Ray Tube (CRT) display device, a liquid crystal display device, an organic Electroluminescence (EL) display device, a plasma display device, or the like may be used as appropriate.

The storage unit 33 is configured to store therein various types of data such as the projection data in the time series, the CT images in the time series, and the like. For example, the storage unit 33 may be configured by using a storage device such as a Random Access Memory (RAM), a Read-Only Memory (ROM), a flash memory, a hard disk, or an optical disk. For example, the storage unit 33 stores therein the CT images in the time series in a medical image file format that is compliant with the Digital Imaging and Communications in Medicine (DICOM) standard. Further, the storage unit 33 may store therein medical data acquired by an external device, in such a manner that the medical data is kept in association with the CT images in the time series, within the medical image file.

The system controlling unit 21 includes a Central Processing Unit (CPU), a Read-Only Memory (ROM), and a RAM. The system controlling unit 21 functions as a hub of the X-ray computed tomography apparatus. The system controlling unit 21 is configured to control the image processing apparatus 27 and to cause the image processing apparatus 27 to perform a blood vessel analyzing process according to the first embodiment.

The image processing apparatus 27 is configured to perform the blood vessel analyzing process according to the first embodiment. The image processing apparatus 27 includes a CPU, a ROM, and a RAM.

In this situation, a computer program (hereinafter, "program") for executing various types of processes performed by the system controlling unit 21 and the image processing apparatus 27 is provided as being incorporated, in advance, in a ROM, the storage unit 33, or the like. The program may be provided as being recorded on a computer-readable storage medium such as a Compact Disk Read-Only Memory (CD-ROM), a Flexible Disk (FD), a Compact Disk Readable (CD-R), or a Digital Versatile Disk (DVD), in a file in a format that is installable or executable for those devices. Further, the program may be provided or distributed by being stored in a computer connected to a network such as the Internet and downloaded via the network. For example, the program is structured with a module including various functional units described later. As actual hardware, as a result of the CPU reading and executing the program from the storage medium such as a ROM, multiple modules are loaded into a main storage device and are generated in the main storage device.

The image processing apparatus 27 according to the first embodiment is configured to identify a second function index of an identification target region, on the basis of the CT images in the time series (the medical images) and correlation information (explained in detail later).

The CT images in the time series correspond to the images and the abovementioned medical images. The medical images used in an analysis performed by the image processing apparatus 27 according to the first embodiment do not necessarily have to be CT images in a time series and may be any images in which it is possible to identify shapes of blood vessels of the subject. For example, the medical images used in the analysis may be Magnetic Resonance Imaging (MRI) images or ultrasound echo images.

In the first embodiment, an example will be explained in which the CT images in the time series are used as the medical images.

The CT images in the time series are represented by data expressing a three-dimensional spatial distribution of the CT values in the time series. For example, the CT images in the time series include approximately twenty images per heartbeat, i.e., CT images corresponding to approximately twenty cardiac phases.

The identification target region is region for which the second function index is to be identified. The identification target region is set in a blood vessel region included in a medical image. In the first embodiment, an example will be explained in which the identification target region is set in an analysis target region within the blood vessel region.

Function indices are indices related to vascular hemodynamics. For example, a function index may be an index indicating functions of a blood vessel related to stenosis. Specific examples of the function indices include a Fractional Flow Reserve (FFR) value, a dynamic index for the inside of a blood vessel, a blood flow amount index, FFR difference, and stenosis ratio. The first embodiment will be explained while referring to a function index of the identification target region as the second function index. Further, when being collectively used in the explanation, a first function index and the second function index will simply be referred to as function indices.

The FFR value is defined as a ratio of the maximum coronary blood flow in the presence of a stenosis to the maximum coronary blood flow in the absence of a stenosis. The FFR value substantially matches a pressure index or a flow amount index of a location distant from a stenosis with respect to a location close to the stenosis. The flow amount index indicates a flow amount ratio or a flow amount difference of the blood flow amount in a coronary artery in a location distant from a stenosis, with respect to the blood flow amount in the coronary artery in a location close to the stenosis. The pressure index indicates a pressure ratio or a pressure difference of the coronary artery internal pressure in a location distant from a stenosis with respect to the coronary artery internal pressure in a location close to the stenosis. The coronary artery internal pressure in a location close to the stenosis may be aortic pressure measured in a location near a stenosis starting part.

The FFR difference refers to a difference in FFR between two points that are separate from each other along a blood vessel, with a measuring point on the blood vessel as a midpoint therebetween, for a predetermined distance toward each of both sides of the midpoint, which is also called $\Delta$FFR. The stenosis ratio is a value indicating the degree of narrowing in the blood vessel in a stenosis region, and is represented as a ratio between the distance of the blood vessel diameter of a reference blood vessel and that of a blood vessel in the stenosis region. For example, the stenosis ratio is expressed as $(B-A)/B \times 100$, where A is the blood vessel diameter serving as a reference that is determined based on the blood vessel of a healthy person, and B is the blood vessel diameter of the blood vessel in the stenosis region. As the blood vessel diameter A of a healthy person, an average blood vessel diameter obtained from past image data of a lot of healthy people or a blood vessel diameter obtained from past image data (i.e., before stenosis occurs) of the same subject may be used. However, the blood vessel diameter A is not limited to a blood vessel diameter of a healthy person. The blood vessel diameter A may be a blood vessel diameter on a position specified by an operator as a position near the stenosis region and on which stenosis has not occurred. Further, instead of the blood vessel diameter of a healthy person, a diameter specified as a diameter of a smallest round shape in which the internal wall of the blood vessel on the stenosis region can be put may be used as the blood vessel diameter A.

The dynamic index refers to an index based on dynamics and related to the blood vessel wall and blood. Dynamic indices related to blood vessel walls can be classified into, for example, indices related to displacements of the blood vessel wall, indices related to stress or strain caused on the blood vessel wall, indices related to a distribution of internal pressure applied to the vascular lumen, indices related to material characteristics expressing the hardness of the blood vessel, and the like. An index related to the material characteristics expressing the hardness of the blood vessel and the like may be expressed by an average slope of a curve expressing a relationship between stress and strain of a blood vessel tissue.

Blood flow amount indices serving as a dynamic index related to blood denote indices of hemodynamics related to the blood flowing in the blood vessel. Examples of the blood flow amount indices include a blood flow amount, a blood flow rate, and a blood viscosity level.

More specifically, the dynamic index indicates a change in the pressure between a blood vessel expansion time and a blood vessel contraction time, a pressure loss between before and after a stenosis, and a pressure loss between an aortic part and a coronary artery part.

The blood flow amount index is an index of hemodynamics related to the blood flowing in the blood vessel. More specifically, the blood flow amount index indicates a change in the blood flow amount between a blood vessel expansion time and a blood vessel contraction time, a flow amount ratio between coronary arteries (between a coronary artery having a stenosis and a coronary artery having no stenosis), or the like.

In the first embodiment, an example will be explained in which the function indices (the first and the second function indices) are FFR values. Details of the first function index will be explained later.

Conventionally, it has been difficult to obtain such function indices easily. Further, in conventional structural fluid analyses of blood vessels, a large amount of analysis resources and analysis time are required.

To cope with this situation, the image processing apparatus 27 according to the first embodiment is configured to identify the second function index of the identification target region, on the basis of the CT images in the time series and the correlation information (explained in detail later) obtained from the reconstructing device 25.

The image processing apparatus 27 according to the first embodiment includes an obtaining unit, a first calculating unit, and a first identifying unit. The obtaining unit is configured to obtain images in a time series including images of a blood vessel of a subject and correlation information indicating a correlational relationship between physical indices of the blood vessel and function indices of the blood vessel related to vascular hemodynamics. The first calculating unit is configured to calculate blood vessel morphology indices in a time series indicating morphology of the blood vessel of the subject, on the basis of the images in the time series. The first identifying unit is configured to identify a function index of the blood vessel of the subject, by using a physical index of the blood vessel of the subject obtained from the blood vessel morphology indices, on the basis of the correlation information.

In addition, the image processing apparatus 27 further includes a first setting unit. The first setting unit is configured to set an identification target region for the function index of the blood vessel, in a blood vessel region included in the images. Further, the first calculating unit calculates the physical index of the identification target region from the blood vessel morphology indices. Further, the first identifying unit identifies the function index of the blood vessel of the subject, on the basis of the correlation information and the physical index calculated by the first calculating unit.

Figure 2:
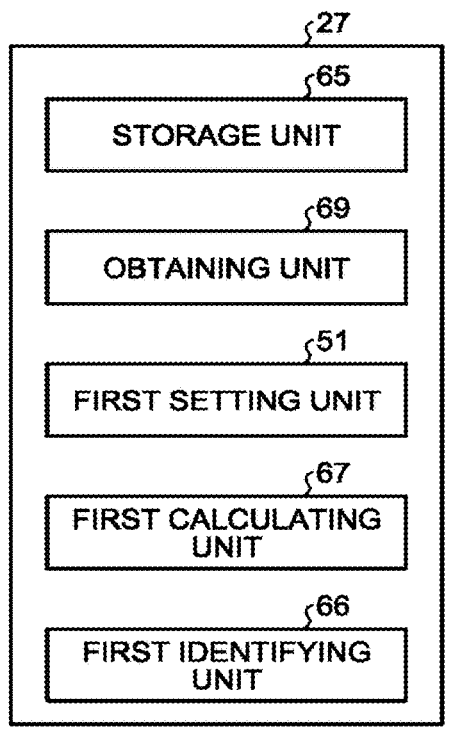
FIG. 2 is a functional block diagram of an image processing apparatus.

FIG. 2 is a functional block diagram of the image processing apparatus according to the first embodiment.

As illustrated in FIG. 2, the image processing apparatus 27 includes the storage unit 65, an obtaining unit 69, a first setting unit 51, a first calculating unit 67, and a first identifying unit 66.

A part or all of the obtaining unit 69, the first setting unit 51, the first calculating unit 67, and the first identifying unit 66 may be realized, for example, by causing a processing apparatus such as a Central Processing Unit (CPU) to execute a program (i.e., realized by software), or may be realized by hardware such as an Integrated Circuit (IC), or may be realized by both software and hardware.

The storage unit 65 is configured to store therein various types of data. For example, the storage unit 65 is configured by using a storage device such as a Random Access Memory (RAM), a Read-Only Memory (ROM), a flash memory, a hard disk, an optical disk, or the like. The storage unit 65 may integrally be formed with the storage unit 33 (see FIG. 1). The storage unit 65 stores therein the CT images in the time series generated by the reconstructing device 25. Further, the storage unit 65 has stored therein the correlation information, in advance.

The inventors of the present disclosure have discovered that there is a strong correlation between the physical indices and the function indices. Thus, the image processing apparatus 27 according to the first embodiment generates the correlation information in advance and stores the generated correlation information into the storage unit 65. Further, the image processing apparatus 27 identifies the function index of the identification target region by using the correlation information. Consequently, the image processing apparatus 27 according to the first embodiment is able to identify the function index of the blood vessel in a non-invasive manner and at a high speed. In this situation, as for the correlation information, a plurality of CT images are obtained from clinical tests, so as to generate the correlation information in advance from the obtained CT images.

Figure 3:
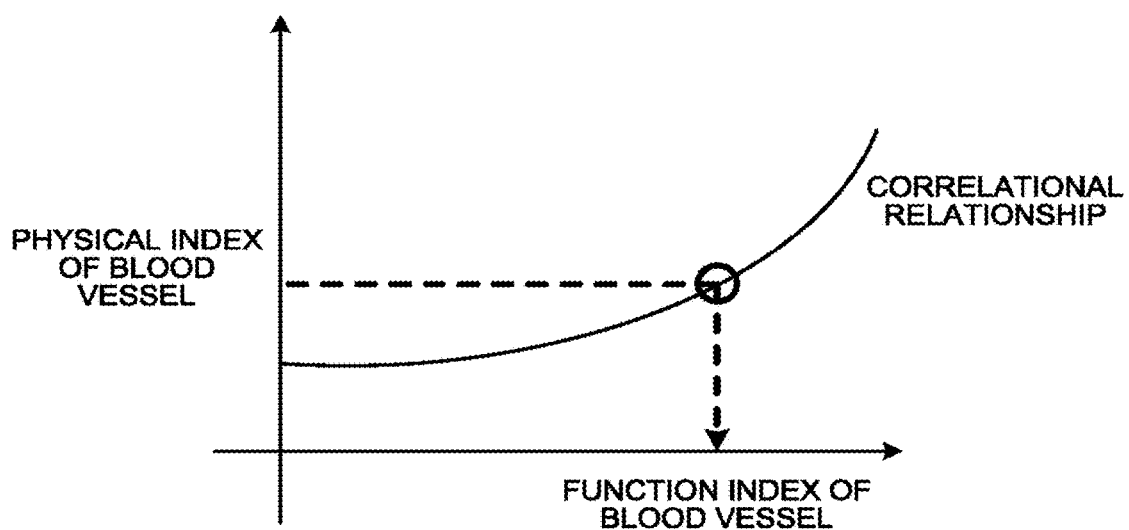
FIG. 3 is a drawing of an example of correlation information.

FIG. 3 is a drawing of an example of the correlation information. As illustrated in FIG. 3, the correlation information is information indicating a correlational relationship between physical indices of a blood vessel and function indices of the blood vessel related to vascular hemodynamics. By referring to the correlation information, it is possible to identify a function index of the blood vessel by using a physical index of the blood vessel.

For example, the correlation information is information indicating a correlation between first physical indices of the blood vessel and first function indices of the blood vessel related to stenosis. The correlation information may be, for example, a database (DB) in which the first physical indices and the first function indices are kept in correspondence with one another. Alternatively, the correlation information may be a table in which these indices are kept in correspondence with one another or may be a statistical model, a stochastic model, a mathematical model, or the like.

The first physical indices are physical indices of the blood vessel. The first physical indices may be, for example, blood vessel cross-sectional shape change indices or blood flow resistance indices.

The blood vessel cross-sectional shape change indices are indices indicating changes in the cross-sectional shape of the blood vessel from an expansion time to a contraction time or from a contraction time to an expansion time, with respect to a coronary artery blood vessel. The blood vessel cross-sectional shape change indices may be, for example, blood vessel cross-sectional shape change indices of a coronary artery or blood vessel cross-sectional shape change indices of the aorta.

As the blood vessel cross-sectional shape change indices of a coronary artery, blood vessel cross-sectional shape change indices of the exit of the coronary artery can be used. The coronary artery exit is such an end of the coronary artery that is positioned on the downstream side in terms of the blood flow direction. The blood vessel cross-sectional shape change indices of a coronary artery may be, for example, coefficients indicating changes in the cross-sectional area of the vascular lumen from either a blood vessel expansion time or a maximum flow amount time to a contraction time (e.g., cardiac phases of 70 to 100%). The change indices are each expressed as a value obtained by dividing a standard deviation by an average value. However, the values do not have to be from a blood vessel expansion time or a maximum flow amount time. The blood vessel cross-sectional shape change indices may be corrected by using a rigidity index related to an expansion/contraction deformation on a cross-sectional plane of the blood vessel. The rigidity index is an index related to the hardness of the blood vessel and has a correlation with blood vessel thickness information and CT value information (a degree of calcification) obtained from the CT images of the blood vessel. For example, a correlational relationship between the blood vessel cross-sectional shape change indices and the rigidity index are defined in advance, so as to correct the blood vessel cross-sectional shape change indices by using the obtained rigidity index.

The blood vessel cross-sectional shape change indices of the aorta are used as blood vessel cross-sectional shape change indices of the entrance of a coronary artery (i.e., a surrounding region of the coronary artery starting part). The coronary artery entrance is such an end of the coronary artery that is positioned on the upstream side in terms of the blood flow direction. The blood vessel cross-sectional shape change indices of the aorta may be, for example, a temporal change ratio or a change amount in an average of the cross-sectional areas of a plurality of cross-sectional planes that are measured in positions away from the coronary artery starting part by short distances (e.g., a number of centimeters approximately) on the upstream side in terms of the blood flow direction; coefficients indicating changes thereof from either a blood vessel expansion time or a maximum flow amount time to a contraction time (e.g., cardiac phases of 70 to 100%); or a dispersion in the cross-sectional areas of a single cross-sectional plane. Instead of the cross-sectional areas, it is also acceptable to use a temporal change ratio or a change amount related to changes in the volume of the vascular lumen, or coefficients indicating changes thereof from either a blood vessel expansion time or a maximum flow amount time to a contraction time (e.g., cardiac phases of 70 to 100%), in consideration of changes in the cross-sectional area in the central line direction. The change amounts may be expressed by using indices related to concentration or dispersion of a contrast agent within the blood vessel.

In the first embodiment, an example will be explained in which the blood vessel cross-sectional shape change indices of a coronary artery (i.e., the blood vessel cross-sectional shape change indices at the coronary artery exit) are used as the blood vessel cross-sectional shape change indices.

The blood flow resistance indices are indices indicating a relationship between pressures losses of the coronary artery and blood flow amounts. A blood flow resistance index may be, for example, a value obtained by dividing a pressure difference between the aorta (i.e., the coronary artery entrance) and the coronary artery exit by the flow amount.

The first function indices are function indices that are related to a stenosis in the blood vessel and that correspond to the first physical indices in the correlation information.

Figure 4A:
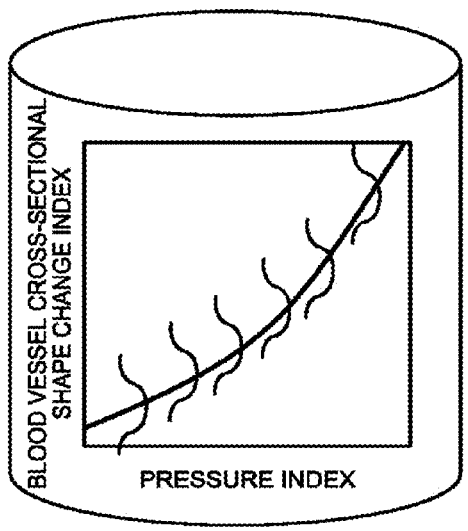
FIGS. 4A and 4B are drawings of specific examples of the correlation information.
Figure 4B:
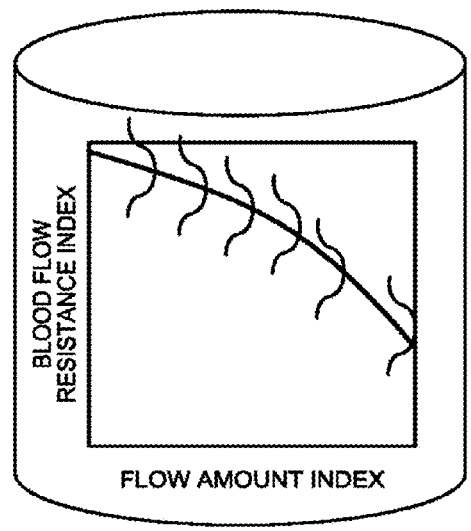

FIGS. 4A and 4B are drawings of specific examples of the correlation information. In the first embodiment, an example will be explained in which the storage unit 65 has stored therein two types of correlation information, in advance.

FIG. 4A is a drawing of correlation information (hereinafter, "the first correlation information") indicating a correlation between the blood vessel cross-sectional shape change indices of the coronary artery and the pressure indices serving as the first function indices. As noted above, the pressure indices each indicate a pressure ratio or a pressure difference of coronary artery internal pressure in a location distant from a stenosis with respect to coronary artery internal pressure in a location close to the stenosis.

FIG. 4B is a drawing of correlation information (hereinafter, "the second correlation information") indicating a correlation between the blood flow resistance indices and the flow amount indices serving as the first function indices. As noted above, the flow amount indices each indicate a flow amount ratio or a flow amount difference of the blood flow amount in the coronary artery in a location distant from a stenosis, with respect to the blood flow amount in the coronary artery in a location close to the stenosis.

The storage unit 65 does not necessarily have to store therein two types of correlation information, as long as the storage unit 65 has stored therein one or more types of correlation information in advance. For example, the storage unit 65 may store therein one type or three or more types of correlation information, in advance. Further, the types of correlation information stored in the storage unit 65 are not limited to those illustrated in FIGS. 4A and 4B.

Figure 5A:
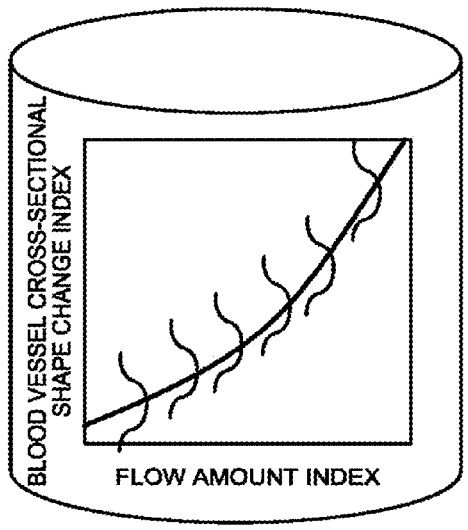
FIGS. 5A and 5B are drawings of other specific examples of the correlation information.
Figure 5B:
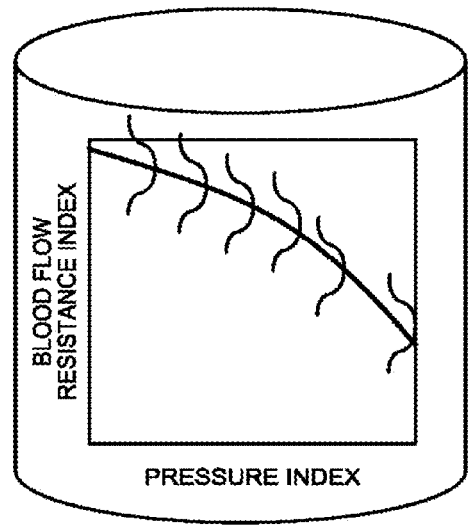

FIGS. 5A and 5B are drawings of other specific examples of the correlation information. For example, the storage unit 65 may have stored therein third correlation information (see FIG. 5A) and fourth correlation information (see FIG. 5B) in advance. The third correlation information is correlation information indicating a correlation between the blood vessel cross-sectional shape change indices of the coronary artery and the flow amount indices serving as the first function indices. The fourth correlation information is correlation information indicating a correlation between the blood flow resistance indices and the pressure indices serving as the first function indices.

The explanation will be continued with reference back to FIG. 2.

The obtaining unit 69 is configured to obtain the medical images in the time series related to the blood vessel of the subject. In the first embodiment, the obtaining unit 69 obtains the CT images in the time series from the storage unit 65, as the medical images.

The first setting unit 51 is configured to set the identification target region for the second function index, in the analysis target region within the blood vessel region included in the CT images.

The first setting unit 51 first sets the analysis target region within the blood vessel region included in the CT images in the time series. The analysis target region is set in an arbitrary part of the blood vessel region related to the coronary artery. After that, the first setting unit 51 further sets the identification target region for the second function index in the analysis target region. For example, according to an instruction from the user via the input unit 29 or through an image processing process, the first setting unit 51 sets the analysis target region in the blood vessel region and further sets the identification target region.

In the first embodiment, an example will be explained in which the first setting unit 51 sets a region including the coronary artery entrance (the aorta) and the coronary artery exit, as the identification target region for the second function index.

The first calculating unit 67 is configured to calculate a second physical index of the identification target region set by the first setting unit 51, on the basis of the CT images in the time series. The definition of the second physical index is the same as that of the first physical indices. In the following explanations, when not distinguished from each other, the first and the second physical indices may simply be referred to as physical indices.

The first calculating unit 67 calculates, as the second physical index, a second physical index of the same type as the first physical indices indicated by the correlation information stored in the storage unit 65.

For example, let us assume that the storage unit 65 has stored therein the first correlation information illustrated in FIG. 4A and the second correlation information illustrated in FIG. 4B. In that situation, the first calculating unit 67 calculates, as the second physical index, at least one selected from between the blood vessel cross-sectional shape change index and the blood flow resistance index with respect to the coronary artery (the coronary artery exit).

The second physical index calculated by the first calculating unit 67 does not necessarily have to be one or both of the blood vessel cross-sectional shape change index and the blood flow resistance index, as long as the second physical index is of the same type as the first physical indices indicated by the correlation information stored in the storage unit 65. Further, when the storage unit 65 has stored therein a plurality of pieces of correlation information, the first calculating unit 67 may calculate a second physical index of a type that is indicated by at least one of the plurality of pieces of correlation information.

In the first embodiment, the example will be explained in which the storage unit 65 has stored therein the first correlation information illustrated in FIG. 4A and the second correlation information illustrated in FIG. 4B. In that situation, for example, the first calculating unit 67 calculates, as the second physical indices, the blood flow resistance index and the blood vessel cross-sectional shape change index of the coronary artery (i.e., the exit of the stenosis region).

A publicly-known method may be used as the method implemented by the first calculating unit 67 for calculating the second physical index on the basis of the CT images in the time series. For example, the first calculating unit 67 may calculate the second physical index from the blood vessel morphology indices. In that situation, the first calculating unit 67 may obtain the blood vessel morphology indices from a third calculating unit 53 (omitted from the first embodiment). Further, in that situation, the image processing apparatus 27 may be configured so as to further include the third calculating unit 53. The third calculating unit 53 will be explained in a second embodiment.

The first identifying unit 66 is configured to identify the second function index of the identification target region, on the basis of the correlation information and the second physical index calculated by the first calculating unit 67.

More specifically, the first identifying unit 66 identifies such a function index from the correlation information that corresponds to a physical index equal to the physical index calculated by the first calculating unit 67, as a function index of the blood vessel of the subject.

For example, the first identifying unit 66 identifies such a first function index from the correlation information that corresponds to the first physical index equal to the second physical index calculated by the first calculating unit 67, as the second function index of the identification target region. The first physical index from the correlation information that is equal to the second physical index calculated by the first calculating unit 67 denotes such a first physical index from the correlation information that is of the same type as, and has the same value as, the second physical index.

To explain further in detail, let us discuss an example in which the storage unit 65 has stored therein the first correlation information illustrated in FIG. 4A. In that situation, the first identifying unit 66 identifies a pressure index corresponding to the blood vessel cross-sectional shape change index of the coronary artery calculated by the first calculating unit 67, as the second function index of the identification target region.

Thus, the image processing apparatus 27 is able to identify the second function index of the identification target region in the non-invasive manner and at a high speed.

Next, details of the blood vessel analyzing process performed by the medical image diagnosis apparatus according to the first embodiment will be explained.

First, a flow in the blood vessel analyzing process will be explained by using an example in which the first identifying unit 66 identifies such a first function index from the correlation information that corresponds to the first physical index equal to the second physical index calculated by the first calculating unit 67, as the second function index of the identification target region.

FIG. 6 is a flowchart of a flow in the blood vessel analyzing process performed by the image processing apparatus 27.

First, the obtaining unit 69 obtains CT images in a time series (step S100).

After that, the first setting unit 51 sets an identification target region in the CT images in the time series obtained at step S100 (step S101).

Subsequently, the first calculating unit 67 calculates the second physical index of the identification target region set at step S101, on the basis of the CT images in the time series obtained at step S100 (step S102).

After that, the first identifying unit 66 identifies such a first function index from the correlation information that corresponds to the first physical index equal to the second physical index calculated by the first calculating unit 67, as the second function index of the identification target region (step S103).

After that, the present routine is ended. In addition, a display process at steps S17 to S20 explained in the second embodiment may further be performed (see FIG. 9; details will be explained later). In that situation, the image processing apparatus 27 may be configured so as to include a display controlling unit 68 (see FIG. 7; detailed will be explained later) described below in the second embodiment.

As explained above, the blood vessel analyzing apparatus 50 according to the first embodiment includes the storage unit 65, the obtaining unit 69, the first setting unit 51, the first calculating unit 67, and the first identifying unit 66. The storage unit 65 has stored therein, in advance, the correlation information indicating the correlation between the first physical indices related to the stenosis in the blood vessel and the first function indices of the blood vessel. The obtaining unit 69 is configured to obtain the medical images in the time series related to the blood vessel of the subject. The first setting unit 51 is configured to set the identification target region for the second function index, in the analyzing target region within the blood vessel region included in the medical images. The first calculating unit 67 is configured to calculate the second physical index of the identification target region on the basis of the medical images. The first identifying unit 66 is configured to identify the second function index of the identification target region, on the basis of the correlation information and the calculated second physical index.

The inventors of the present disclosure have discovered that there is a strong correlation between the physical indices and the function indices. Thus, the blood vessel analyzing apparatus 50 identifies the second function index of the identification target region, by using the correlation information.

Consequently, the blood vessel analyzing apparatus 50 according to the first embodiment is able to identify the function index of the blood vessel in the non-invasive manner and at a high speed.

For example, a conventional structural fluid analysis takes a long period of time (e.g., twelve hours or longer) to perform the analysis. In contrast, because the blood vessel analyzing apparatus 50 according to the first embodiment uses the correlation information, it is possible to simplify at least one step (process) among the plurality of processes performed for the purpose of identifying the function index. Thus, the blood vessel analyzing apparatus 50 according to the first embodiment is able to identify the function index of the blood vessel in the non-invasive manner and at a high speed.

Further, the first identifying unit 66 identifies such a first function index from the correlation information that corresponds to the first physical index equal to the calculated second physical index, as the second function index of the identification target region.

Consequently, in addition to the advantageous effects described above, the blood vessel analyzing apparatus 50 according to the first embodiment is further able to identify the function index at a high speed.

Second Embodiment

Next, the second embodiment will be explained.

An image processing apparatus according to the second embodiment is configured to set an ex-ante distribution of a latent variable related to at least one selected from between a shape in a stress-free state (hereinafter, "stress-free shape") and a physical property value of an identification target region and to further calculate a prediction value of a blood flow amount index or a blood vessel morphology index of the identification target region, on the basis of the ex-ante distribution. Further, on the basis of the images of the subject in the time series, the image processing apparatus is configured to calculate an observed value of either the blood flow amount index or the blood vessel morphology index. After that, the image processing apparatus is configured to identify an ex-post distribution of the latent variable on the basis of the prediction value, the observed value, and the function index obtained on the basis of the correlation information in such a manner that the calculated prediction value matches the observed value, and to further identify a function index of the blood vessel of the subject, on the basis of an identified value in the ex-post distribution.

For example, observed variables such as the blood vessel morphology index and the blood flow amount index that are measured from the images in the time series may have uncertainty. When a latent variable is statistically identified in the presence of uncertainty, if the statistical identifying process was performed while envisioning every possible value of the latent variable, the image analyzing process would require an extremely long period of time. In contrast, according to the configuration described above, because the ex-post distribution of the latent variable is identified in such a manner that the prediction value matches the observed value, it is possible to perform the identifying process while using a probability distribution indicated by the function index as a constraint condition. Consequently, it is possible to identify the function index of the blood vessel in a non-invasive manner and at a high speed.

FIG. 1 is a schematic hardware diagram of a medical image diagnosis apparatus (an X-ray computed tomography apparatus) according to the second embodiment. As illustrated in FIG. 1, the X-ray computed tomography apparatus includes the CT gantry 10 and a console 20A. The X-ray computed tomography apparatus has the same configuration as the configuration in the first embodiment except that the X-ray computer tomography apparatus includes the console 20A, in place of the console 20 described in the first embodiment.

The console 20A has the system controlling unit 21 serving as a hub and includes the gantry controlling unit 23, the reconstructing device 25, and a blood vessel analyzing apparatus 50A. The console 20A has the same configuration as the configuration of the console 20 described in the first embodiment, except that the console 20A includes the blood vessel analyzing apparatus 50A, in place of the blood vessel analyzing apparatus 50.

The blood vessel analyzing apparatus 50A is an apparatus configured to perform a blood vessel analysis. The blood vessel analyzing apparatus 50A includes the system controlling unit 21, an image processing apparatus 27A, the input unit 29, the display unit 31, and the storage unit 33. The blood vessel analyzing apparatus 50A has the same configuration as the configuration of the blood vessel analyzing apparatus 50 described in the first embodiment, except that the blood vessel analyzing apparatus 50A includes the image processing apparatus 27A, in place of the image processing apparatus 27. Only the different parts will be explained below.

The image processing apparatus 27A is configured to identify the second function index of the identification target region, on the basis of the CT images (the medical images) in the time series and the correlation information.

In the second embodiment, the first identifying unit is configured to set the ex-ante distribution of the latent variable related to at least one selected from between the stress-free shape and the physical property value of the identification target region. Further, the first identifying unit is configured, on the basis of the ex-ante distribution, to calculate a prediction value of at least one selected from between the blood flow amount index and the blood vessel morphology index, with respect to the identification target region. Further, the first identifying unit is configured to calculate an observed value of at least one selected from between the blood flow amount index and the blood vessel morphology index, on the basis of the images. Further, the first identifying unit is configured to identify an ex-post distribution of the latent variable on the basis of the prediction value, the observed value, and such a function index from the correlation information that corresponds to the physical index equal to the physical index calculated by the calculating unit, in such a manner that the prediction value matches the observed value. Further, the first identifying unit is configured to identify a function index of the blood vessel of the subject, on the basis of an identified value in the ex-post distribution.

Further, in the second embodiment, the image processing apparatus 27A further includes a display controlling unit. The display controlling unit is configured to cause a display unit to display a combined image obtained by combining a first image indicating the correlation information with a second image indicating the function index identified by the first identifying unit.

FIG. 7 is a functional block diagram of the image processing apparatus 27A according to the second embodiment.

As illustrated in FIG. 7, the image processing apparatus 27A includes a storage unit 65A, the obtaining unit 69, the first setting unit 51, the first calculating unit 67, a first identifying unit 66A, and the display controlling unit 68.

A part or all of the obtaining unit 69, the first setting unit 51, the first calculating unit 67, the first identifying unit 66A, and the display controlling unit 68 may be realized, for example, by causing a processing apparatus such as a CPU to execute a program (i.e., realized by software), or may be realized by hardware such as an IC, or may be realized by both software and hardware.

The obtaining unit 69, the first setting unit 51, and the first calculating unit 67 are the same as those in the first embodiment. Thus, the explanation thereof will be omitted.

The storage unit 65A is configured to store therein various types of data. For example, the storage unit 65A is configured by using a storage device such as a Random Access Memory (RAM), a Read-Only Memory (ROM), a flash memory, a hard disk, an optical disk, or the like. The storage unit 65A may integrally be formed with the storage unit 33 (see FIG. 1). In the same manner as in the first embodiment, the storage unit 65A stores therein the CT images in the time series generated by the reconstructing device 25. Further, in the same manner as in the first embodiment, the storage unit 65A has stored the correlation information therein, in advance. The correlation information is the same as that in the first embodiment. For example, the storage unit 65A has stored therein the correlation information illustrated in FIGS. 4A, 4B, 5A, and 5B in advance.

In the second embodiment, the storage unit 65A has further stored therein first information and second information, in advance.

The first information is information in which a latent variable is kept in correspondence with at least one selected from between the blood flow amount indices and the blood vessel morphology indices. The first information may be a database (DB) or may be a table.

The latent variable is a hypothetical parameter that is not directly observed from the CT images in the time series. In the second embodiment, the latent variable is a variable related to at least one selected from between a stress-free shape and a physical property value, with respect to the identification target region (described in detail later) in the blood vessel.

More specifically, the latent variable denotes at least one selected from between a material deformation parameter and a cross-sectional shape parameter.

The material deformation parameter is a latent variable indicating material characteristics of the blood vessel. The material deformation parameter indicates a blood vessel deformation ratio in response to pressure, or the like. More specifically, the material deformation parameter is a modulus of elasticity and may be, for example, a Young's modulus or a Poisson's ratio. Details of the material deformation parameter will be explained later.

The cross-sectional shape parameter is a latent variable indicating the shape of the blood vessel in a stress-free state. The cross-sectional shape parameter may be expressed by, for example, the cross-sectional area of the vascular lumen, the thickness of the blood vessel wall, the radius of the vascular lumen, the diameter of the vascular lumen, or the like.

The cross-sectional shape parameter may include a load condition parameter, a boundary condition parameter, a variance distribution parameter, and the like.

The load condition parameter is a latent variable indicating a distribution of internal pressure applied to the vascular lumen, an average pressure level inside the blood vessel, or the like. The boundary condition parameter indicates a boundary condition for a structure analysis or a fluid analysis. The boundary condition indicates a blood flow rate, pressure from the blood flow, or a changing ratio of either of these. The variance distribution parameter is a variance distribution parameter related to uncertainty of the blood vessel morphology indices or the blood vessel cross-sectional shape change indices in a time series.

The variance distribution parameter related to the uncertainty of the blood vessel morphology indices or the blood vessel cross-sectional shape change indices in the time series expresses, as a probability distribution, uncertainty of boundary coordinates of a blood vessel tissue or blood and a feature point (e.g., a blood vessel branching part or a contrast agent dispersion positional arrangement) in a spatial coordinate system, or uncertainty of a geometric structure parameter (e.g., the radius of the lumen on a cross-sectional plane perpendicular to the central line), or uncertainty of the medical image data itself (e.g., CT values and boundary threshold values), in consideration of the fact that medical image data has a variance distribution due to noise in the CT values and a probability distribution due to ambiguity of boundary threshold values for a biological tissue.

The blood flow amount indices included in the first information are indices indicating the blood flow that flows through the blood vessel in a stress-free state. The blood flow amount indices each indicate, for example, a flow amount, a flow rate, an average flow rate on a cross-sectional plane in the central line direction, or an average flow amount on a cross-sectional plane in the central line direction. Alternatively, pressure levels (the internal pressure inside the blood vessel) corresponding to the blood flow may be used as the blood flow amount indices.

The blood vessel morphology indices are indices indicating morphology of the blood vessel. For example, the blood vessel morphology indices are each expressed with three-dimensional coordinates or a geometric index. For example, the blood vessel morphology indices are each expressed with three-dimensional coordinates of a plurality of pixels in a region where either a cross-sectional plane perpendicular to the central line of the blood vessel or a plane perpendicular to the plane of the vascular lumen intersects the vascular lumen, the blood vessel wall, and a plaque region. Further, for example, the geometric index is expressed with the radius or the diameter of the vascular lumen for every certain angle on a cross-sectional plane perpendicular to the central line of the blood vessel and a directional vector at 0°, or an average area or an average radius with respect to all the angles on the cross-sectional plane, or the volume of the vascular lumen defined by a plurality of cross-sectional planes perpendicular to the central line direction of the blood vessel, or a blood vessel wall volume or a plaque volume defined by a plurality of cross-sectional planes perpendicular to the plane of the lumen of the blood vessel. Alternatively, the geometric index may be expressed with a cross-sectional area, the diameter, or the radius of the vascular lumen.

In the second embodiment, an example will be explained in which the first information is information in which the latent variable is kept in correspondence with the blood flow amount indices. Further, in the second embodiment, an example will be explained in which pressure levels are used as the blood flow amount indices.

FIGS. 8A and 8B are drawings of examples of the first information and the second information (details will be explained later).

FIG. 8A is a drawing of an example of the first information. In the example illustrated in FIG. 8A, the first information is information in which a cross-sectional shape parameter serving as a latent variable, a material deformation parameter serving as another latent variable, and pressure levels serving as the blood flow amount indices are kept in correspondence with one another. In FIG. 8A, the material deformation parameter is expressed with the slope a. In other words, in the example in FIG. 8A, the storage unit 65A has stored therein, in advance, the first information indicating relationships between the cross-sectional shape parameter and the pressure levels each of which corresponds to a different one of a plurality of material deformation parameter values (the slope a in FIG. 8A) exhibiting the mutually-different values.

The second information is information in which pressure differences are kept in correspondence with flow amounts. FIG. 8B is a drawing of an example of the second information. The pressure differences indicate differences in the pressure between before and after the stenosis part. In the second embodiment, an example will be explained in which the pressure differences indicate differences in the pressure between the coronary artery entrance (the aorta) and the coronary artery exit.

The first information and the second information may be calculated from the CT images of the subject in the time series and stored in the storage unit 65A.

Returning to the description of FIG. 7, the first identifying unit 66A is configured to identify the second function index of the identification target region by performing a Monte Carlo simulation.

More specifically, the first identifying unit 66A is configured to identify the ex-post distribution by setting a data distribution related to errors between the prediction value and observed value and performing a statistical identifying process on a probability distribution indicated by the function index of the blood vessel and the data distribution, with respect to the ex-ante distribution. After that, the first identifying unit 66A keeps resetting the ex-ante distribution and performing the statistical identifying process, until the ex-post distribution satisfies an identification ending condition.

Further, the first identifying unit 66A calculates, as the prediction value, at least one selected from between the blood flow amount index and the blood vessel morphology index that is from the first information and that corresponds to the latent variable indicated by the ex-ante distribution. In that situation, the obtaining unit 69 further obtains the first information in which the latent variable is kept in correspondence with at least one selected from between the blood flow amount indices and the blood vessel morphology indices.

Further, the first identifying unit 66A calculates blood vessel morphology indices in a time series and blood vessel cross-sectional shape change indices in a time series with respect to the analysis target region in the blood vessel region, on the basis of the images. Further, the first identifying unit 66A tentatively constructs a dynamic model related to the analysis target region, on the basis of the images, the blood vessel morphology indices in the time series, and the blood vessel cross-sectional shape change indices in the time series. Further, the first identifying unit 66A calculates the prediction value by analyzing the dynamic model.

Further, the first identifying unit 66A identifies the function index of the blood vessel of the subject by constructing a dynamic model to which an identified value in the ex-post distribution is assigned and performing either a blood vessel stress analysis or a blood fluid analysis on the dynamic model.

The first identifying unit 66A includes a second setting unit 62, a second identifying unit 63, a second calculating unit 64, a third identifying unit 61, a fourth identifying unit 70, the third calculating unit 53, a constructing unit 55, and a controlling unit 71.

The second setting unit 62 is configured to set the ex-ante distribution of the latent variable related to at least one selected from between the stress-free shape and the physical property value of the identification target region. The ex-ante distribution indicates the probability distribution of values which the latent variable can possibly take.

In this situation, it is not possible to calculate a latent variable that indicates the actual blood vessel, directly from the CT images. For this reason, the image processing apparatus 27A determines tentative values of the latent variable as the ex-ante distribution. For example, the second setting unit 62 sets an ex-ante distribution of the material deformation parameter and the cross-sectional shape parameter, as the ex-ante distribution of the latent variable.

In the second embodiment, the second setting unit 62 sets, as the ex-ante distributions of the latent variable of the identification target region, an ex-ante distribution of the latent variable of the coronary artery exit in a stress-free state and an ex-ante distribution of the latent variable of the coronary artery entrance (i.e., the aorta) in a stress-free state. The ex-ante distributions set for the coronary artery exit and the coronary artery entrance may have mutually the same values or mutually-different values.

The second identifying unit 63 is configured to calculate the prediction value of at least one selected from between the blood flow amount index and the blood vessel morphology index of the identification target region, on the basis of the ex-ante distributions set by the second setting unit 62.

For example, the second identifying unit 63 calculates the prediction value by using the first information (see FIG. 8A). Alternatively, the second identifying unit 63 may calculate the prediction value by using a dynamic model constructed by the constructing unit 55.

First, an example will be explained in which the second identifying unit 63 calculates the prediction value by using the first information.

The second identifying unit 63 calculates, as the prediction value, at least one selected from between the blood flow amount index and the blood vessel morphology index that is from the first information and that corresponds to the ex-ante distribution of the latent variable set by the second setting unit 62. The first information may be generated from the CT images in the time series in advance and stored in the storage unit 65A.

Let us assume that the first information illustrated in FIG. 8A is stored in the storage unit 65A. Let us also assume that the second setting unit 62 has set an ex-ante distribution of the cross-sectional shape parameter and the material deformation parameter, as the ex-ante distribution of the latent variable. In that situation, the second identifying unit 63 first reads such a pressure level that corresponds to the set material deformation parameter (the slope a in FIG. 8A) and the set cross-sectional shape parameter, as a blood flow amount index.

More specifically, the second identifying unit 63 reads, from the first information, the pressure level corresponding to the ex-ante distribution of the latent variable of the coronary artery exit in the stress-free state. Further, the second identifying unit 63 reads, from the first information, the pressure level corresponding to the ex-ante distribution of the latent variable of the coronary artery entrance (i.e., the aorta exit) in the stress-free state. Subsequently, the second identifying unit 63 calculates the pressure difference between the pressure levels. After that, the second identifying unit 63 reads such a flow amount that corresponds to the calculated pressure difference, from the second information (see FIG. 8B). By performing these processes, for example, the second identifying unit 63 calculates the blood flow amount as the prediction value of the blood flow amount index.

Alternatively, the second identifying unit 63 may calculate a pressure difference or a pressure ratio between a pressure level corresponding to the ex-ante distribution of the latent variable of the coronary artery exit in the stress-free state and a pressure level corresponding to the ex-ante distribution of the latent variable of the coronary artery entrance in the stress-free state, as the prediction value of the pressure index.

Next, an example will be explained in which the second identifying unit 63 identifies the prediction value by using the dynamic model constructed by the constructing unit 55.

First, a dynamic model constructing process performed by the constructing unit 55 will be explained.

The constructing unit 55 is configured to tentatively construct the dynamic model related to the analysis target region, on the basis of a shape history (the blood vessel morphology indices in the time series) and a forced displacement history (the blood vessel cross-sectional shape change indices in the time series) calculated by the third calculating unit 53, as well as the CT images in the time series.

Before the explanation of the constructing unit 55, the third calculating unit 53 will be explained. The third calculating unit 53 is configured to calculate the blood vessel morphology indices in the time series and the blood vessel cross-sectional shape change indices in the time series, from the CT images in the time series. More specifically, by performing an image processing process on the CT images in the time series, the third calculating unit 53 calculates the blood vessel morphology indices in the time series and the blood vessel cross-sectional shape change indices in the time series, with respect to the coronary artery entrance (e.g., the aorta) serving as an identification target region and the coronary artery exit serving as another identification target region.

To explain in detail, the third calculating unit 53 performs an image analyzing process and a tracking process. The third calculating unit 53 calculates the blood vessel morphology indices in the time series by performing the image analyzing process on the CT images in the time series. Further, the third calculating unit 53 calculates the blood vessel cross-sectional shape change indices in the time series, by performing the tracking process on the CT images in the time series.

To explain further in detail, when performing the image analyzing process, the third calculating unit 53 extracts a blood vessel region from each of the CT images in the time series and specifies a pixel region related to the vascular lumen (hereinafter, "vascular lumen region") and a pixel region related to the blood vessel wall (hereinafter, "blood vessel wall region"). After that, the third calculating unit 53 specifies, as the blood vessel morphology index, three-dimensional coordinates of a plurality of pixels in a region where either a cross-sectional plane perpendicular to the central line of the blood vessel or a plane perpendicular to the plane of the vascular lumen intersects the vascular lumen, the blood vessel wall, and a plaque region.

In this situation, as noted above, each of the blood vessel morphology indices does not necessarily have to be the three-dimensional coordinates, but may be a geometric index such as the radius or the diameter of the vascular lumen for every certain angle on a cross-sectional plane perpendicular to the central line and a directional vector at 0°, or an average area or an average radius with respect to all the angles on a cross-sectional plane, or the volume of the vascular lumen defined by a plurality of cross-sectional planes perpendicular to the central line direction, or a blood vessel wall volume or a plaque volume defined by a plurality of cross-sectional planes perpendicular to the plane of the lumen.

In the second embodiment, as an example, the third calculating unit 53 calculates the blood vessel morphology indices of the aorta that is the coronary artery entrance and the blood vessel morphology indices of the coronary artery exit, each serving as the identification target region. For example, the blood vessel morphology indices of the aorta may each be expressed by cross-sectional areas of a plurality of cross-sectional planes positioned a little (e.g., a number of centimeters approximately) above the coronary artery starting part. The blood vessel morphology indices of the coronary artery exit may each be expressed by, for example, vascular lumen cross-sectional areas obtained by sectioning the coronary artery from a blood vessel expansion time to a contraction time along the central line direction at constant intervals. Alternatively, the diameters in a stress-free state or the radii in a stress-free state may be used in place of the cross-sectional areas.

Further, the third calculating unit 53 performs the tracking process as follows: The third calculating unit 53 sets a plurality of tracked points such as a feature point, a feature shape, a representative point, a pixel, or the like in the blood vessel region, the blood, the contrast agent, or protons, according to an instruction from the user via the input unit 29 or through an image processing process. For example, the third calculating unit 53 sets a set of tracked points including a blood vessel branching part, a feature shape on the surface, and the like. Further, by performing an interpolating process or the like, the third calculating unit 53 calculates a temporal change in displacements of a node in the blood vessel wall surface, the blood vessel wall interior, or the blood vessel lumen of the dynamic model, on the basis of displacement data of the set of tracked points obtained from the tracking process performed at different points in time (in different cardiac phases), so as to provide the calculated result as a forced displacement.

The forced displacement denotes a forced displacement caused by an overall movement due to the pulsatile movement of the heart, local stretching and shrinking, torsion, and shear deformations.

Further, for example, the third calculating unit 53 defines the node on the blood vessel central line in the dynamic model. The third calculating unit 53 may extract a deformation related to stretching and shrinking, torsion, and bending with respect to the central line direction of the blood vessel, from the temporal change in the displacements of the node in the blood vessel wall surface, the blood vessel wall interior, or the blood vessel lumen of the dynamic model and may use the extracted deformation as a forced displacement of the node on the blood vessel central line and a cross-sectional plane perpendicular to the central line. As explained here, as the blood vessel cross-sectional shape change indices, the forced displacement data (the forced displacement history) of the node at the different points in time in the dynamic model is specified.

In the second embodiment, the type of the dynamic model is not particularly limited, unless otherwise noted. It is assumed that an initial dynamic model denotes a dynamic model that has assigned thereto a sampling set (a set made up of combinations of parameters) related to the parameters of the latent variable obtained from a probability distribution of the latent variable or a range of the variable.

Further, the constructing unit 55 first constructs a shape model on the basis of the CT images in the time series and the shape history. The shape model schematically expresses a geometric structure of the blood vessel region at each of different points in time. The shape model is divided into a plurality of discretized regions, for example. The apex of each of the discretized regions is called a node.

The constructing unit 55 may construct the shape model for each of the different points in time, on the basis of the blood vessel region included in the CT image at each of the different points in time and the blood vessel morphology indices in the time series calculated by the third calculating unit 53 or may construct the shape model for each of the different points in time, on the basis of the blood vessel region included in a CT image in a specific temporal phase and the blood vessel morphology index calculated by the third calculating unit 53. Further, for example, when it is assumed that no residual stress is present in the blood vessel corresponding to the analysis target region in an initial load state, it is assumed that, to determine a temporal phase in the stress-free state, the temporal phase in which the blood vessel corresponding to the analysis target region contracts the most represents the stress-free state.

When having constructed the shape model, the constructing unit 55 sets sampling values obtained from an ex-ante distribution or a range of variable of the latent variable, into the dynamic model. For example, the sampling values are values sampled from a set made up of combinations of the parameters of each latent variable, by implementing a Markov chain Monte Carlo method. As noted above, there are a plurality of types of latent variables including the material deformation parameter, the cross-sectional shape parameter, and the like. For this reason, the combinations of the parameters of each latent variable denote combinations of the values (the parameters) of the latent variable of each of the different types.

When having constructed the shape model, the constructing unit 55 assigns the blood vessel cross-sectional shape change indices in the time series, i.e., the forced displacement history, calculated by the third calculating unit 53, to the shape model.

In other words, the constructing unit 55 generates a tentative dynamic model, by assigning the ex-ante distribution of the latent variable and the forced displacement history to the shape model.

Alternatively, as noted above, the second identifying unit 63 may calculate the prediction value by using the dynamic model constructed by the constructing unit 55.

In that situation, the second identifying unit 63 identifies the prediction value by performing an inverse analysis on the tentative dynamic model generated by assigning the ex-ante distribution (the latent variable) set by the second setting unit 62 and the forced displacement history, to the shape model.

For example, the second identifying unit 63 includes a blood vessel stress analyzing unit 57 and a blood fluid analyzing unit 59.

The blood vessel stress analyzing unit 57 is configured to calculate the prediction value of the blood vessel morphology indices in the time series by performing a blood vessel stress analysis on the tentative dynamic model. The blood vessel indices may be any of the blood vessel morphology indices described above and may preferably be, for example, cross-sectional shape indices of the lumen region or the cross-sectional shape indices of the blood vessel wall, with respect to the blood vessel central line direction.

More specifically, each of the cross-sectional shape indices of the lumen region is at least one selected from between coordinate values of a pixel of interest in the lumen region and a geometric structure parameter of the lumen region (the radius of the lumen region, the diameter of the lumen region, or the like). Further, each of the cross-sectional shape indices of the blood vessel wall region is, specifically, at least one selected from between coordinate values of a pixel of interest in the blood vessel wall region and a geometric structure parameter of the blood vessel wall region (the radius of the blood vessel wall region, the diameter of the wall region, or the like). In this situation, the prediction value denotes a calculated value of the blood vessel morphology index calculated by performing the blood vessel stress analysis on the tentative dynamic model.

The blood fluid analyzing unit 59 calculates a prediction value of the blood flow amount indices in the time series, by performing a blood fluid analysis on the dynamic model constructed tentatively. The blood flow amount indices are at least one selected from among: blood flow amounts, blood flow rates, and spatial/temporal average values thereof. In that situation, the prediction value denotes a calculated value of the blood flow amount index calculated by performing the blood fluid analysis on the tentative dynamic model.

In the manner explained above, the second identifying unit 63 identifies the prediction value of at least one selected from between the blood flow amount index and the blood vessel morphology index, with respect to the identification target region, by using either the first information or the dynamic model.

The second calculating unit 64 is configured to calculate an observed value of at least one selected from between the blood flow amount index and the blood vessel morphology index, on the basis of the CT images in the time series.

In the second embodiment, for example, the second calculating unit 64 calculates the observed value of at least one selected from between the blood flow amount index and the blood vessel morphology index, by constructing a shape model from the CT images in the time series and analyzing the constructed shape model. The construction of the shape model is performed in the same manner as described above. In the second embodiment, the second calculating unit 64 calculates, for example, a total value of blood inflow amounts into coronary arteries, as the observed value of at least one selected from between the blood flow amount index and the blood vessel morphology index. The total value of blood inflow amounts denotes a total amount of blood flowing into a plurality of coronary arteries.

The third identifying unit 61 is configured to identify an ex-post distribution of the latent variable, on the basis of the prediction value, the observed value, and such a first function index from the correlation information that corresponds to the second physical index calculated by the first calculating unit 67, in such a manner that the predication value matches the observed value.

For example, let us assume that the observed value is A2 expressing a "total value of blood inflow amounts into the plurality of coronary arteries". Let us also assume that, calculated as the prediction value of the blood flow amount index is a flow amount A1 corresponding to the pressure difference between the pressure level corresponding to the ex-ante distribution of the latent variable of the coronary artery exit in the stress-free state and the pressure level corresponding to the ex-ante distribution of the latent variable of the coronary artery entrance (i.e., the aorta exit) in the stress-free state.

In that situation, the third identifying unit 61 first sets, for each of one or more coronary arteries, a data distribution related to an error between a sum of the flow amounts A1 each obtained as the prediction value for a different one of the coronary arteries and the observed value A2 expressing the "total value of blood inflow amounts into the plurality of coronary arteries". In that situation, for example, the data distribution is expressed with a flow amount index or the like. The flow amount index indicates a flow amount or a flow amount ratio between the coronary artery entrance and the coronary artery exit. In other words, the data distribution is expressed with a multivariate normal distribution function related to the error between the prediction value and the observed value.

For example, the third identifying unit 61 calculates, for each of the one or more coronary arteries, a post-correction flow amount A3 obtained by correcting the flow amount A1 serving as the prediction value, in such a manner that the sum of the flow amounts A1 each serving as the prediction value of a different one of the coronary arteries matches the observed value A2 expressing the "total value of blood inflow amounts into the plurality of coronary arteries". After that, the third identifying unit 61 calculates a normal distribution function value related to the error between the flow amount A1 that is the pre-correction prediction value and the flow amount A3 that is the post-correction value, for each of the one or more coronary arteries and further sets a product thereof as the data distribution. The data distribution may individually be set for each of the different points in time or may collectively be set for the plurality of points in time.

Subsequently, the third identifying unit 61 reads, from the correlation information, such a first function index that corresponds to the first physical index equal to the second physical index calculated by the first calculating unit 67 on the basis of the CT images in the time series. For example, let as assume that a blood vessel cross-sectional shape change index of the coronary artery entrance has been calculated as the second physical index. In that situation, the third identifying unit 61 reads, from the correlation information (e.g., the first correlation information illustrated in FIG. 4A), such a pressure index that corresponds to the calculated blood vessel cross-sectional shape change index, as the first function index. In that situation, alternatively, the third identifying unit 61 may read a flow amount index as the first function index, by reading such a flow amount that corresponds to a read pressure index, from the second information (see FIG. 8B).

Subsequently, the third identifying unit 61 identifies an identified value in the ex-post distribution of the latent variable, by performing a statistical identifying process on the probability distribution indicated by the abovementioned first function index and the abovementioned data distribution, with respect to the ex-ante distribution of the latent variable set by the second setting unit 62. The statistical identifying process may be implemented by using, for example, a hierarchical Bayesian model or a Markov chain model.

In this situation, until the ex-ante distribution identified by the third identifying unit 61 satisfies the identification ending condition, the controlling unit 71 controls the second setting unit 62 so as to keep resetting the ex-ante distribution and also controls the third identifying unit 61 so as to keep performing the statistical identifying process.

For this reason, the third identifying unit 61 identifies the ex-post distribution of the latent variable, by performing a Monte Carlo simulation while varying the value of the ex-ante distribution of the latent variable set by the second setting unit 62 until the identification ending condition is satisfied, while limiting the ex-ante distribution of the latent variable set by the second setting unit 62 to the probability distribution indicated by the abovementioned first function indices (an expected range of possible values of the latent variable corresponding to the first function indices). For example, the third identifying unit 61 calculates a probability distribution of the pressure index or the flow amount index on the basis of the first function indices, as the probability distribution indicated by the first function indices.

After that, the third identifying unit 61 identifies an identified value of the latent variable from a statistical value such as the most frequent value or an average value of the ex-post distribution, with respect to the ex-post distribution of the latent variable at the time when the identification ending condition is satisfied. For example, the third identifying unit 61 identifies an ex-post distribution related to pressure values of the vascular lumen as the ex-post distribution of the latent variable and further identifies a pressure value of the vascular lumen from the ex-post distribution.

For example, the third identifying unit 61 may be configured so as to include a first statistical identification processing unit 61-1 and a second statistical identification processing unit 61-2.

In that situation, the first statistical identification processing unit 61-1 is configured to set a data distribution based on the prediction value and the observed value of the blood vessel morphology index. After that, the first statistical identification processing unit 61-1 reads, from the correlation information, such a first function index that corresponds to the second physical index calculated by the first calculating unit 67 on the basis of the CT images in the time series. For example, when the blood vessel cross-sectional shape change index of the coronary artery (entrance) has been calculated as the second physical index, the third identifying unit 61 reads, from the correlation information (e.g., the first correlation information illustrated in FIG. 4A), such a pressure index that corresponds to the calculated blood vessel cross-sectional shape change index, as the first function index.

Subsequently, the first statistical identification processing unit 61-1 identifies the identified value in the ex-post distribution of the latent variable by performing the Monte Carlo simulation or the statistical identifying process, on the basis of the ex-ante distribution of the latent variable set by the second setting unit 62, the abovementioned first function index, and the abovementioned data distribution.

A process performed by the second statistical identification processing unit 61-2 is the same as the process performed by the first statistical identification processing unit 61-1, except that the index used for the calculation of the data distribution is different.

In other words, the second statistical identification processing unit 61-2 is configured to set a data distribution based on the prediction value and the observed value of the blood flow amount index.

After that, the second statistical identification processing unit 61-2 reads, from the correlation information, such a first function index that corresponds to the second physical index calculated by the first calculating unit 67 on the basis of the CT images in the time series. For example, when the blood flow resistance index has been calculated as the second physical index, the third identifying unit 61 reads, from the correlation information (e.g., the second correlation information illustrated in FIG. 4B), such a flow amount index that corresponds to the calculated blood flow resistance index, as the first function index.

Subsequently, the second statistical identification processing unit 61-2 identifies the identified value in the ex-post distribution of the latent variable by performing the Monte Carlo simulation or the statistical identifying process, on the basis of the ex-ante distribution of the latent variable set by the second setting unit 62, the abovementioned first function index, and the abovementioned data distribution.

In this situation, the observed value of the blood flow amount index is assumed to be, for example, a change in the blood flow amount sent out to the aorta. Further, it is acceptable to use the observed value of the blood vessel morphology index, as a change value in the volume of the left ventricle (a Cardiac Function Analysis [CFA] value) measured by performing an image processing process on the CT images in the time series. A flow rate or a flow amount may be calculated by calculating a temporal change in the moving amount of a feature point, by performing a tracking process on the images of the contrast agent after the contrast agent is injected into the coronary artery. Alternatively, a flow rate or a flow amount may be calculated by obtaining a change amount in the concentration of the contrast agent in the blood vessel central line direction or in a specific temporal region and dividing the change in the concentration by the interval distance between the regions in the central line direction or calculating a temporal change ratio of the change in the concentration. For an MRI process, a tracking process is performed on images of protons, whereas for an ultrasound echo process, a flow amount is calculated by implementing a contrast echocardiography method.

Further, when the coordinate values of the pixels in the analysis target region are not assumed to be definitive values, i.e., when it is assumed that the geometric structure of the analysis target region has uncertainty, the geometric structure may be included in the latent variable.

The statistical identifying process by the first statistical identification processing unit 61-1 and the statistical identifying process by the second statistical identification processing unit 61-2 both do not necessarily have to be performed. In other words, it is acceptable to perform one selected from between the statistical identifying process by the first statistical identification processing unit 61-1 and the statistical identifying process by the second statistical identification processing unit 61-2.

The fourth identifying unit 70 is configured to identify the second function index of the identification target region, on the basis of the identified value in the ex-post distribution of the latent variable identified by the third identifying unit 61.

If the identified value in the ex-post distribution of the latent variable is a value indicating a function index, the fourth identifying unit 70 identifies the identified value as the second function index. For example, if the identified value in the ex-post distribution of the latent variable is a pressure ratio, the fourth identifying unit 70 identifies the pressure ratio as the second function index.

Alternatively, the fourth identifying unit 70 may identify the second function index of the identification target region by using a dynamic model. In that situation, the fourth identifying unit 70 constructs the dynamic model, by assigning the identified value in the ex-post distribution of the latent variable that was identified, to the shape model. The method used for constructing the shape model or the dynamic model is the same as the method used by the constructing unit 55. The fourth identifying unit 70 may transmit a construction instruction that includes the identified value in the ex-post distribution of the latent variable that was identified, to the constructing unit 55. In that situation, when having received the construction instruction, the constructing unit 55 may construct a dynamic model by assigning the identified value in the ex-post distribution included in the construction instruction to the shape model and may transmit the constructed dynamic model to the fourth identifying unit 70.

After that, the fourth identifying unit 70 identifies the second function index of the identification target region by performing either a blood vessel stress analysis or a blood fluid analysis on the constructed dynamic model.

The display controlling unit 68 is configured to generate the combined image obtained by combining the first image indicating the correlation information stored in the storage unit 65A with the second image indicating the second function index identified by the first identifying unit 66A. Further, the display controlling unit 68 causes the display unit 31 to display the generated combined image.

For example, as illustrated in FIGS. 4A, 4B, 5A, and 5B, the display controlling unit 68 uses, as the first image, an image in which the vertical axis expresses a physical index (the blood vessel cross-sectional shape change index or the blood flow resistance index), whereas the horizontal axis expresses a function index (the pressure index or the flow amount index), while, in addition, a curve indicating the correlational relationship between these two indices is rendered. Further, for example, the display controlling unit 68 generates a combined image in which the second image indicating the identified second function index is combined with the first image and causes the display unit 31 to display the combined image. For example, the display controlling unit 68 uses, as the second image, an image in which a point-like graphic element is arranged on the horizontal axis rendered in the first image in such a position that corresponds to the value of the identified second function index. Alternatively, the display controlling unit 68 may further combine a third image indicating the second physical index calculated by the first calculating unit 67 with the first image. For example, the display controlling unit 68 uses, as the third image, an image in which a point-like graphic element is arranged on the vertical axis rendered in the first image in such a position that corresponds to the value of the calculated second physical index. In that situation, it is desirable to arrange the graphic element in the second image and the graphic element in the third image to be displayed in mutually-different colors to an extent that enables the user to recognize the difference. In this situation, the shapes of the graphic elements included in the second and the third images do not necessarily have to be points. The graphic elements may have a square/rectangular shape, a triangular shape, a diamond shape, or the like.

By viewing the combined image, the user is able to easily understand the function index (the second function index) of the blood vessel of the subject.

Alternatively, the display controlling unit 68 may construct a dynamic model in which the second function index identified by the first identifying unit 66A is assigned to a shape model and cause the display unit 31 to display an image of the dynamic model. The construction of the dynamic model may be performed in the same manner as performed by the constructing unit 55.

Next, details of a blood vessel analyzing process performed by a medical image diagnosis apparatus according to the second embodiment will be explained.

In the second embodiment, the first identifying unit 66A identifies a stenosis region by using either the dynamic model or the first information and the like.

FIG. 9 is a flowchart of a flow in a blood vessel analyzing process performed by the image processing apparatus 27A. FIG. 9 illustrates a procedure in a situation where the first identifying unit 66A identifies the stenosis region by using either the dynamic model or the first information and the like.

First, the obtaining unit 69 obtains the CT images in the time series (step S1).

Subsequently, the first setting unit 51 sets an identification target region in the CT images in the time series obtained at step S1 (step S2).

After that, the third calculating unit 53 calculates blood vessel morphology indices in a time series and blood vessel cross-sectional shape change indices in a time series, on the basis of the CT images in the time series obtained at step S1 (step S3).

Subsequently, the first calculating unit 67 calculates a second physical index of the identification target region set at step S2, on the basis of the CT images in the time series obtained at step S1 (step S4).

After that, the second setting unit 62 sets an ex-ante distribution of a latent variable related to at least one selected from between the shape in a stress-free state and the physical property value, with respect to the identification target region (step S5).

Subsequently, the second identifying unit 63 judges whether a dynamic model is to be used or not for calculating a prediction value of at least one selected from between the blood flow amount index and the blood vessel morphology index with respect to the identification target region (step S6).

For example, first judgment information indicating whether a dynamic model is to be used or not for the calculation of the prediction value is stored in the storage unit 65A, in advance. It is possible to change the first judgement information as appropriate according to an instruction from the user through an operation on the input unit 29 or the like.

For example, the user inputs, via the input unit 29, information indicating whether or not the speed is prioritized in the calculation of the prediction value. When having received information indicating that the speed is prioritized, the second identifying unit 63 stores first judgment information indicating that the prediction value is to be calculated by using the first information into the storage unit 65A, in advance. On the contrary, when having received information indicating that the speed is not prioritized, the second identifying unit 63 stores first judgment information indicating that the predication value is to be calculated by using the dynamic model into the storage unit 65A in advance. After that, when performing the process at step S6, the second identifying unit 63 makes the judgment at step S6 by assessing the first judgment information.

When the second identifying unit 63 has determined that a dynamic model is to be used (step S6: Yes), the second identifying unit 63 calculates the prediction value of at least one selected from between the blood flow amount index and the blood vessel morphology index with respect to the identification target region, by using the dynamic model, on the basis of the ex-ante distribution set at step S5 (step S7). After that, the process proceeds to step S9.

On the contrary, when the second identifying unit 63 has determined that a dynamic model is not to be used (step S6: No), the second identifying unit 63 calculates the prediction value of at least one selected from between the blood flow amount index and the blood vessel morphology index with respect to the identification target region, by using the first information, on the basis of the ex-ante distribution set at step S5 (step S8). After that, the process proceeds to step S9.

Subsequently, the second calculating unit 64 calculates an observed value of at least one selected from between the blood flow amount index and the blood vessel morphology index, on the basis of the CT images in the time series obtained at step S1 (step S9).

The image processing apparatus 27A is configured so that the processes at steps S1 through S9 are performed in parallel for each of a plurality of coronary arteries. Alternatively, the processes at steps S1 through S9 may sequentially (i.e., serially) be performed for each of the plurality of coronary arteries.

After that, the third identifying unit 61 sets a data distribution indicating a multivariate normal distribution function related to the error between the prediction value and the observed value of each of the one or more coronary arteries (step S10).

Subsequently, the third identifying unit 61 reads, from the correlation information, such a first function index that corresponds to the first physical index equal to the second physical index calculated at step S4 (step S11).

After that, the third identifying unit 61 performs a Monte Carlo simulation where the processes at steps S5 through S12 are repeated while varying the value of the ex-ante distribution of the latent variable set at step S5, so that the third identifying unit 61 keeps judging in the negative at step S12 (step S12: No) until the identification ending condition is satisfied, while limiting the ex-ante distribution of the latent variable set by the second setting unit 62 to the probability distribution indicated by the first function index read at step S11.

The judgment of whether the identification ending condition is satisfied or not is made by judging whether the error between the prediction value and the observed value is equal to or smaller than a predetermined threshold value. Alternatively, the judgment of whether the identification ending condition is satisfied or not may be made by judging whether the Monte Carlo simulation has been performed for each of all the values in the abovementioned expected range.

When having judged in the affirmative at step S12 (step S12: Yes), the third identifying unit 61 identifies the ex-post distribution of the latent variable identified when the affirmative judgment was made at step S12, as a final ex-post distribution (step S13). After that, the third identifying unit 61 identifies an identified value of the latent variable on the basis of a statistical value such as the most frequent value or an average value of the ex-post distribution.

Subsequently, the fourth identifying unit 70 judges whether a dynamic model is to be used or not for identifying the second function index (step S14).

For example, second judgment information indicating whether a dynamic model is to be used or not for the calculation of the second function index is stored in the storage unit 65A, in advance. It is possible to change the second judgement information as appropriate according to an instruction from the user through an operation on the input unit 29 or the like.

For example, the user inputs, via the input unit 29, information indicating whether or not the speed is prioritized in the identification of the second function index. When having received information indicating that the speed is prioritized, the fourth identifying unit 70 stores second judgment information indicating that the identified value in the ex-post distribution is used without any modification as the second function index, into the storage unit 65A in advance. On the contrary, when having received information indicating that the speed is not prioritized, the fourth identifying unit 70 stores second judgment information indicating that the second function index is to be identified by using a dynamic model, into the storage unit 65A in advance.

When the fourth identifying unit 70 has determined that a dynamic model is to be used (step S14: Yes), the process proceeds to step S15. At step S15, the fourth identifying unit 70 identifies a second function index of the identification target region, by analyzing a dynamic model in which the identified value in the ex-post distribution of the latent variable identified at step S13 is assigned to a shape model (step S15). After that, the process proceeds to step S17.

On the contrary, when the fourth identifying unit 70 has determined that a dynamic model is not to be used (step S14: No), the process proceeds to step S16. At step S16, the fourth identifying unit 70 identifies the identified value in the ex-post distribution of the latent variable identified at step S13, as the second function index (step S16). After that, the process proceeds to step S17.

Subsequently, the display controlling unit 68 generates a combined image obtained by combining a first image indicating the correlation information stored in the storage unit 65A with a second image indicating the second function index identified at step S15 or S16 (step S17). After that, the display controlling unit 68 causes the display unit 31 to display the generated combined image (step S18).

Subsequently, the display controlling unit 68 constructs a dynamic model in which the second function index identified at either step S15 or step S16 is assigned to a shape model (step S19). After that, the display controlling unit 68 causes the display unit 31 to display an image of the dynamic model constructed at step S19 (step S20). Thus, the present routine is ended.

Another mode is also acceptable in which the display process is not performed in one of both of the processes at steps S17 and S18 and the processes at steps S19 and S20.

Incidentally, it is desirable to configure the image processing apparatus 27A so as to store, into the storage unit 65A, at least one selected from between the second function index identified by the first identifying unit 66A and the dynamic model constructed by assigning the second function index to the shape model. Further, it is also desirable to store the second function index and the dynamic model so as to be kept in association with subject information, medical examination information, or the like, for the purpose of facilitating searches or the like. In that situation, the dynamic model may be stored in the storage unit 65A in a data format showing numerical values obtained from the dynamic model in the form of a database or a table.

Further, in the blood vessel analyzing process illustrated in FIG. 9, when the dynamic model is constructed multiple times, dynamic models constructed by using mutually the same method may be used, or dynamic models constructed by using mutually-different methods may be used. When dynamic models constructed by using mutually-different methods are used, for example, it is acceptable to, at first, tentatively identify the latent variable by using a simplified dynamic model, before accurately identifying the latent variable by using a continuum dynamic model. By performing the statistical identifying process in the two separate stages while using the mutually-different methods, it is possible to converge the parameters of the latent variable in a shorter period of time. Examples of the method using a simplified dynamic model include a method that uses a formula of material dynamics of a thick-walled cylinder regarding an internal pressure and an external pressure, as well as a Hagen-Poiseuille flow and a modified Bernoulli equation. Examples of the method using a continuum dynamic model include a Finite Element Method (FEM) structural fluid analysis. Details of the identifying method that uses the simplified dynamic model and the identifying method that uses the continuum dynamic model will be explained later.

The image processing apparatus 27A according to the second embodiment uses such a first function index that is exhibited in the correlation information and that corresponds to the physical index (the first physical index equal to the second physical index) calculated from the CT images, as a constraint condition.

After that, while using the first function index, the third identifying unit 61 performs a statistical identifying process based on a Markov random field theory and a hierarchical Bayesian model on a super-multi-degree-of-freedom large scale problem. The third identifying unit 61 identifies the ex-post distribution of the latent variable, by integrating together a plurality of probability distributions (in the present example, the abovementioned data distribution, the probability distribution corresponding to the first function index, and the ex-ante distribution set by the second setting unit 62) and interpolating missing data. To perform this process, the third identifying unit 61 performs an estimating process by using the hierarchical Bayesian method based on a model that uses the Markov random field theory. In this mechanism, on the basis of actual measured results for the deformation state of the structure serving as the analysis target, it is possible to estimate a pressure level and a flow amount distribution with respect to certain latent variables (e.g., a load condition parameter and a boundary condition parameter) on the basis of an identified intermediate variable.

In coronary artery structural fluid analyses, problems of identifying a material deformation parameter, a boundary condition parameter, and a load condition parameter are considered to be non-linear inverse analyses, and it is often the situation that the uniqueness and the stability of solutions are not guaranteed. Because material characteristics of biological tissues and a range in which blood pressure values can realistically fall are predictable as transcendental information, it is also acceptable to set these values as probability distributions of constraint conditions. Further, because it is also possible to predict that pressure levels and displacements are smooth spatially and temporally, it is also acceptable to set these types of information as probability distributions of constraint conditions.

Alternatively, if it is possible to take the fact that the blood flow does not have any reflux into consideration, it is also acceptable to use the fact that the slope of an overall pressure distribution in the blood vessel central line direction is negative (a pressure decrease is present) as a constraint condition. With respect to the load condition parameter (the internal pressure distribution or the like), the boundary condition parameter, and the material deformation parameter, it is possible to set, as a data distribution, a squared error distribution of the observed value of the blood vessel cross-sectional shape change index based on the CT images in the time series and the prediction value of the blood vessel cross-sectional shape change index based on the dynamic model.

It is also acceptable to add a squared error distribution related to an observable average flow amount, as a data distribution. On the basis of these ex-ante distributions and data distributions, it is possible to identify the ex-post distribution by using a hierarchical Bayesian model and a Monte Carlo method. On the basis of an event probability and a dispersion of the ex-post distribution, it is possible to obtain an identified value of the parameter of the latent variable. When the event probability is higher and the dispersion is smaller, it is considered that the identified value has a higher degree of certainty.

Even if the ex-post distribution is a multi-peak distribution, the identified value having the smallest dispersion may be selected from among a plurality of identified values. Alternatively, when there is a possibility that multiple identified values may be present, it is possible to perform a structural fluid analysis by using each of different identification conditions, so as to recognize the possibility of each situation and to utilize the identified value and the analysis result as guideline information for diagnoses and clinical preventions. Because the CT images in the time series also include errors, the blood vessel morphology index related to the nodes in the dynamic model also includes errors. For this reason, it is also acceptable to treat each of the blood vessel morphology indices as, for example, a probability variable of a normal distribution that uses the prediction value of the blood vessel morphology index measured from the CT images in the time series as an average value and to set a constraint condition while including a constraint where the spatial order of the positions are maintained.

Further, during the process of identifying the identified value in the ex-post distribution, there may be a situation where no uniqueness is exhibited and there are a plurality of possible candidates. In that situation, robustness (stability) of each of the candidates for the identified value is judged by checking change amounts of a sample set made up of identified values of the latent variable, with respect to a sampling point of a random number that follows the uncertainty of the blood vessel morphology index measured from the CT images in the time series. A final identified value may be determined on the basis of the robustness of each of the candidates for the identified value.

<Dynamic Models>

Next, details of the dynamic model will be explained. The constructing unit 55 is able to construct different types of dynamic models in accordance with each kind of dynamic model. When a Finite Element Method (FEM) based on continuum dynamics is used, the constructing unit 55 constructs both a shape model (a FEM model) for performing a stress analysis on the blood vessel wall and a shape model (a FEM model) for performing a fluid analysis on the blood.

When a simplified identifying method based on material dynamics is used, a relationship among pressure levels, moduli of elasticity, and displacements is calculated in an approximate manner, by using a formula of a thick-walled cylinder in material dynamics to which internal pressure is applied. In that situation, a thick-walled cylinder approximation is used as a shape model for each of a plurality of discretized regions arranged in the central line direction. More specifically, the constructing unit 55 specifies a vascular lumen shape, a blood vessel wall surface shape, and the center of the cross-sectional plane, with respect to each of cross-sectional planes that pass through nodes that are discretely arranged on the central line.

After that, on the basis of the vascular lumen shapes and the blood vessel wall surface shapes, the constructing unit 55 calculates an average area, an average radius of the lumen, and an average wall thickness. Further, the constructing unit 55 constructs a shape model by performing a thick-walled cylinder approximation on the blood vessel region in each of the discretized regions, on the basis of the average area, the average radius of the lumen, and the average wall thickness.

When a simplified identifying method based on fluid dynamics is used, a relational expression between flow amounts and pressure losses related to fluid dynamics is used for calculating an average pressure level and an average flow amount of the blood flow, in an approximate manner.

As explained above, the image processing apparatus 27A is able to identify the latent variable by using the formula related to material dynamics and the relational expression between flow amounts and pressure losses. For example, let us discuss an example in which, as a dynamic model, a formula of a thick-walled tube in material dynamics is used for the deformation of the blood vessel so that a change in the tube diameter is expressed by using a change in the internal pressure and a modulus of elasticity.

When the initial shape is assumed to correspond to a stress-free state (e.g., the state in which the blood vessel contracts the most), by setting the moduli of elasticity of the blood vessel wall and the plaque to certain values, it is possible to obtain a relational expression between a temporal change amount in the observed value of the blood vessel cross-sectional shape change index such as an average radius of the vascular lumen and a change amount in the internal pressure. Observed values of the blood vessel cross-sectional shape change index can be measured from the CT images in the time series. The temporal change in the internal pressure distribution of the blood vessel is determined so as to match the temporal change amount in the observed value of the blood vessel cross-sectional shape change index. By performing a fluid analysis of the blood under the condition of the internal pressure distribution, it is possible to measure a prediction value of the blood flow amount index. If the prediction value of the blood flow amount index does not match the observed value, the image processing apparatus 27A further performs the same analysis after changing the modulus of elasticity of either the blood vessel wall or the plaque that was initially determined.

By repeatedly performing this process, the image processing apparatus 27A is able to determine the latent variable indicating the moduli of elasticity of the blood vessel wall and the plaque, the internal pressure distribution, a pressure boundary condition for the fluid analysis, or the like that matches the observed value of the blood vessel cross-sectional shape change index and the observed value of the blood flow amount index. In order to implement this determination method more efficiently and stably, it is also acceptable to use a statistical identifying method based on a hierarchical Bayesian model and a Markov chain Monte Carlo method.

As explained above, the image processing apparatus 27A included in the blood vessel analyzing apparatus 50A according to the second embodiment includes the storage unit 65A, the obtaining unit 69, the first setting unit 51, the first calculating unit 67, and the first identifying unit 66A. The storage unit 65A has stored therein, in advance, the correlation information indicating the correlation between the first physical indices related to the stenosis in the blood vessel and the first function indices of the blood vessel. The obtaining unit 69 is configured to obtain the images in the time series related to the blood vessel of the subject. The first setting unit 51 is configured to set the identification target region for the second function index, in the blood vessel region included in the images. The first calculating unit 67 is configured to calculate the second physical index of the identification target region, on the basis of the medical images. The first identifying unit 66A is configured to identify the second function index of the identification target region, on the basis of the correlation information and the calculated second physical index.

Further, the first identifying unit 66A includes the second setting unit 62, the second identifying unit 63, the second calculating unit 64, the third identifying unit 61, the fourth identifying unit 70, and the constructing unit 55.

The second setting unit 62 is configured to set the ex-ante distribution of the latent variable related to at least one selected from between the shape in the stress-free state and the physical property value, with respect to the identification target region. On the basis of the ex-ante distribution, the second identifying unit 63 is configured to calculate the prediction value of at least one selected from between the blood flow amount index and the blood vessel morphology index with respect to the identification target region. The second calculating unit 64 is configured to calculate the observed value of at least one selected from between the blood flow amount index and the blood vessel morphology index, on the basis of the medical images in the time series. The third identifying unit 61 is configured to identify the ex-post distribution of the latent variable, on the basis of the prediction value, the observed value, and such a first function index from the correlation information that corresponds to the first physical index equal to the calculated second physical index, in such a manner that the prediction value matches the observed value. The fourth identifying unit 70 is configured to identify the second function index of the identification target region, on the basis of the identified value in the ex-post distribution.

In this situation, the observed variables such as the blood vessel morphology index and the blood flow amount index measured from the CT images in the time series have uncertainty. When a latent variable is statistically identified in the presence of such uncertainty, if the statistical identifying process was performed while envisioning every possible value of the latent variable, the image analyzing process would require an extremely long period of time. To cope with this situation, it is necessary to identify the ex-post distribution of the latent variable under an appropriate constraint condition.

In the second embodiment, after the third identifying unit 61 has identified the ex-post distribution of the latent variable, on the basis of the prediction value, the observed value, and such a first function index from the correlation information that corresponds to the first physical index equal to the calculated second physical index, in such a manner that the prediction value matches the observed value, it is possible to perform the identifying process while using the probability distribution indicated by the first function index as the constraint condition.

Consequently, the blood vessel analyzing apparatus 50A according to the second embodiment is able to identify the function index (the second function index) of the blood vessel in the non-invasive manner and at a high speed.

Further, in the second embodiment, the image processing apparatus 27A includes the storage unit 65A, the obtaining unit 69, the first setting unit 51, the first calculating unit 67, the first identifying unit 66A, and the display controlling unit 68.

The storage unit 65A has stored therein, in advance, the correlation information indicating the correlation between the first physical indices related to the stenosis in the blood vessel and the first function indices of the blood vessel. The obtaining unit 69 is configured to obtain the images in the time series related to the blood vessel of the subject. The first setting unit 51 is configured to set the identification target region for the second function index, in the blood vessel region included in the images. The first calculating unit 67 is configured to calculate the second physical index of the identification target region, on the basis of the medical images. The first identifying unit 66A is configured to identify the second function index of the identification target region, on the basis of the correlation information and the calculated second physical index. The display controlling unit 68 is configured to cause the display unit 31 to display the combined image 80 obtained by combining the first image indicating the correlation information with the second image indicating the second function index.

With these arrangements, by viewing the combined image 80, the user is able to easily understand the function index (the second function index) of the blood vessel of the subject.

In the second embodiment, the example is explained in which the first identifying unit 66A includes the constructing unit 55. However, when no dynamic model is constructed, it is acceptable to use a configuration in which the constructing unit 55 is not provided.

Third Embodiment

Next, a third embodiment will be explained.

An image processing apparatus according to the third embodiment is configured to identify a function index of a blood vessel of a subject, by further using a change amount in the concentration in the images in the time series including images of the blood vessel of the subject.

With the configuration described above, by utilizing blood vessel deformation data indicating a change amount of a cross-sectional plane, a change amount in the blood flow resistance, or the like, as well as contrast agent flow amount information indicating a change amount in the concentration, or the like, it is possible to identify the function index of the blood vessel indicating a blood pressure level, a flow amount, an FFR value, a pressure level of the blood vessel wall, or the like, in a non-invasive manner and at a high speed. Further, it is possible to identify the function index of the blood vessel with a high level of precision.

Stenosis in coronary arteries can be a serious pathological issue that may lead to an ischemic heart disease. The FFR value mentioned above substantially matches the ratio of coronary artery internal pressure of a location distant from a stenosis to coronary artery internal pressure of a location close to the stenosis. Further, if it is possible to perform a stenosis analysis on the coronary artery by using a heart CT, it is possible to reduce invasiveness, to reduce the burden on the subject, and to save the medical costs, compared to an FFR measuring process that involves catheter surgery. In other words, if it is possible to measure a pressure difference between before and after the stenosis on the basis of CT images by performing a structural fluid analysis, quantification of impacts of the stenosis is expected to be possible.

Clinically speaking, as methods for evaluating kinetics of coronary circulations, methods such as ultra-high-speed CT, cineangiogram, ultrasound methods, nuclear medical imaging methods including Single Photon Emission Tomography (SPECT) and Positron Emission Tomography (PET), and nuclear Magnetic Resonance Imaging (MRI) methods have been developed and introduced and are being useful in the evaluation of diagnoses and treatment methods.

It is, however, difficult to accurately capture images of coronary microvasculature by using a medical image diagnosis apparatus. Further, even if the shape of a blood vessel is clear, there are many situations where medical images include noise and where there is an ambiguity in the setting of threshold values for the boundaries of biological tissues. As explained herein, shapes of blood vessels obtained from medical image diagnosis apparatuses have uncertainty.

When CT images are utilized in a clinical application, there are many situations where an analysis is performed by using, as an analysis target, only a region positioned on the upstream side of coronary microvasculature such as a region from the aorta starting part to a part of a coronary artery having a large diameter. Because the blood flows in the coronary arteries are significantly affected also by the tonus of the coronary microvasculature, it is an issue that needs to be addressed to appropriately set boundary conditions used in a fluid analysis to analyze a flow amount, a pressure level, or a change ratio in either of these, with respect to the exit of the region of a coronary artery having a large diameter.

Further, the blood flows in the coronary arteries are affected by mechanical factors due to the pulsatile movement of the heart (an overall movement due to the pulsatile movement, a forced displacement caused by local stretching and shrinking, torsion, and shear deformations, or an external force). When only a fluid analysis is performed, because it is not possible to take the impact of the mechanical factors such as the pulsatile movement of the heart into account, it is not possible to accurately measure a flow amount distribution and an internal pressure distribution of the blood flows.

Further, structure-fluid coupled analyses taking the impact of mechanical factors into account have also been performed on the heart and blood vessel systems that are rendered in images. However, even when the structure-fluid coupled analyses are performed, there are many situations where it is difficult to properly set boundary conditions for the entrance and the exit of a blood vessel and material models of blood vessels and plaques that are used in a fluid analysis of the blood (including a contrast agent).

Further, when there is microvasculature that is not rendered in images, there are some situations where it is not possible to take the impact of the microvasculature on the blood flows into account. For this reason, there is a possibility that results of structure-fluid coupled analyses may not properly realize the actual blood flows or the actual blood vessel deformations. Further, when the boundary conditions, the load conditions, and the material models are not appropriate or when the blood vessels involve a significantly large move, there are some situations where problems are found in convergence properties and analysis stability.

As explained above, there are some situations where conventional structural fluid analyses of blood vessels require a large amount of analysis resources and analysis time and where analysis results have a large error. Thus, there may be a problem in utilizing these analyses at clinical sites realistically.

A configuration of the medical image diagnosis apparatus according to the third embodiment is the same as that illustrated in FIG. 1. Thus, the explanation thereof will be omitted. A blood vessel analyzing apparatus according to the third embodiment will be explained below.

Figure 10:
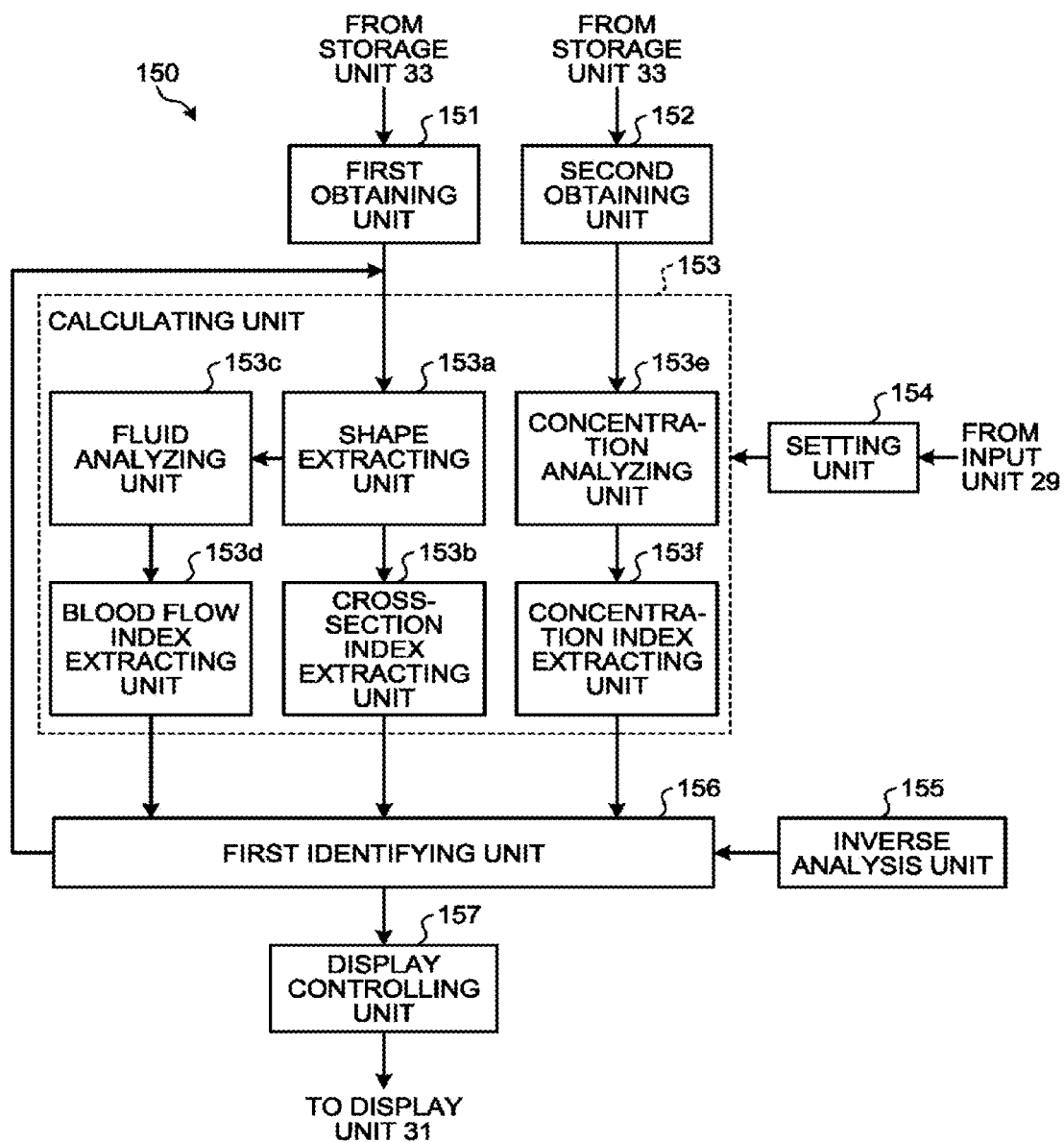
FIG. 10 is a functional block diagram illustrating functions of a blood vessel analyzing apparatus according to an embodiment.

FIG. 10 is a functional block diagram illustrating functions of a blood vessel analyzing apparatus 150 according to the third embodiment. In the present example, some of the constituent elements that have substantially the same functions as those illustrated in FIG. 1 will be referred to by using the same reference characters, and detailed explanations thereof will be omitted. As illustrated in FIG. 10, the blood vessel analyzing apparatus 150 includes a first obtaining unit 151, a second obtaining unit 152, a calculating unit 153, a setting unit 154, an inverse analysis unit 155, a first identifying unit 156, and a display controlling unit (an output unit) 157. The first obtaining unit 151, the second obtaining unit 152, the calculating unit 153, the setting unit 154, and the first identifying unit 156 accomplish the similar functions as the obtaining unit 69, the first calculating unit 67, the first setting unit 51, and the first identifying unit 66 illustrated in FIG. 2, and the different portion of concrete processes according to the embodiments will be described mainly here. A part or all of the functions of the blood vessel analyzing apparatus 150 illustrated in FIG. 10 may be configured by using hardware or may be configured as a blood vessel analyzing program by using software. Further, a blood vessel analyzing program executed by the blood vessel analyzing apparatus 150 may be provided as a computer program product as being written on a computer-readable storage medium such as a CD-ROM, a DVD, or the like, in a file that is in an installable format or an executable format.

The first obtaining unit 151 is configured to obtain four-dimensional (4D) image data (data in which volume data expressing a three-dimensional spatial distribution of CT values is indicated in a time series) of a blood vessel from the storage unit 33, for example. Alternatively, the first obtaining unit 151 may be provided with a function for generating 4D image data that can be used in a blood vessel analysis.

The second obtaining unit 152 is configured to obtain contrast agent image data of blood vessels and heart tissues from the storage unit 33, for example. Alternatively, the second obtaining unit 152 may be provided with a function for generating the contrast agent image data.

The calculating unit 153 includes a shape extracting unit 153$a$, a cross-section index extracting unit 153$b$, a fluid analyzing unit 153$c$, a blood flow index extracting unit 153$d$, a concentration analyzing unit 153$e$, and a concentration index extracting unit 153$f$.

The shape extracting unit 153$a$ is configured to extract shape change data indicating a chronological change in the blood vessel shape, from the 4D image data of the blood vessels obtained by the first obtaining unit 151. For example, the shape extracting unit 153$a$ extracts shapes of the aorta and one or more coronary arteries.

The cross-section index extracting unit 153$b$ extracts a blood vessel cross-sectional shape change index by using the shape change data extracted by the shape extracting unit 153$a$. For example, on the basis of the 4D image data of the blood vessels, the cross-section index extracting unit 153$b$ extracts blood vessel cross-sectional shape change indices (indices of a cross-sectional plane of the aorta blood vessel in a surrounding region of the coronary artery starting part and of a blood vessel cross-sectional plane in a surrounding region of the exit of a coronary artery analysis target) either from an expansion time to a contraction time or from a contraction time to an expansion time of each of the coronary artery blood vessels. For example, the cross-section index extracting unit 153$b$ extracts the index indicating a change in the cross-sectional plane of the aorta and the indices each indicating a change in the cross-sectional plane of a different one of the plurality of coronary arteries.

In a specific example, the blood vessel cross-sectional shape change index of a coronary artery may be, for example, a change coefficient (a value obtained by dividing a standard deviation by an average value) of the vascular lumen cross-sectional area from either a blood vessel expansion time or the maximum flow amount time to a contraction time (e.g., cardiac phases of 70 to 100%) of the coronary artery. In this situation, it is assumed that the cardiac phases are expressed in the range of 0% to 100%. Further, examples of the blood vessel cross-sectional shape change index of the aorta include a temporal change ratio or a change amount in an average cross-sectional area of a plurality of cross-sectional planes positioned a little (a number of centimeters approximately) above the coronary artery starting part, as well as a change coefficient from a blood vessel expansion time (or the maximum flow amount time) to a contraction time (cardiac phases of 70 to 100%). Alternatively, in place of the cross-sectional area, the cross-section index extracting unit 153b may use, as the index, a temporal change ratio or a change amount related to a change in the volume of the vascular lumen, or a change coefficient from a blood vessel expansion time (or the maximum flow amount time) to a contraction time (cardiac phases of 70 to 100%), in which the change in the cross-sectional area in the central line direction of the blood vessel is taken into account. A change amount in the cross-sectional area in CT images is a value affected by the contrast agent concentration and dispersion in the blood vessel.

The fluid analyzing unit 153c is configured to analyze changes in fluid, by using the blood flowing in a blood vessel as the fluid. On the basis of an analysis result obtained by the fluid analyzing unit 153c, the blood flow index extracting unit 153d is configured to extract a blood flow resistance such as, for example, a relationship between pressures losses and flow amounts of a coronary artery.

Figure 13:
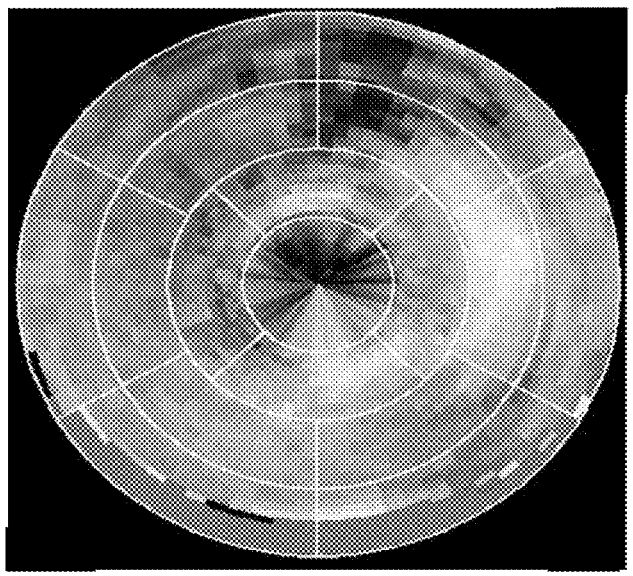
FIG. 13 is a drawing illustrating a display screen with a contrast agent concentration map showing a developed view of heart walls.

The concentration analyzing unit 153e is configured to analyze contrast agent concentration levels of the blood vessels and the heart tissues. For example, a contrast agent concentration map is a map in which the cardiac walls are developed and divided into sections, as illustrated in FIG. 13 (explained later). The divided sections represent regions in each of which a coronary artery guarantees the blood flow.

On the basis of an analysis result obtained by the concentration analyzing unit 153e, the concentration index extracting unit 153f is configured to extract indices (concentration indices) each indicating a change in the contrast agent concentration in the blood vessels and the heart tissues (e.g., the aorta, the coronary arteries, and the myocardia). In a specific example, the index indicating a change in the contrast agent concentration in a blood vessel may be, for example, a change amount between before and after a stenosis, a temporal change amount, or a change amount of which the value is normalized in consideration of dependency thereof on the blood vessel cross-sectional area or on the contrast agent concentration level, with respect to the CT value (an average value or the largest value) on a blood vessel cross-sectional plane in the central line direction. Further, the index indicating a change in the contrast agent concentration of the myocardia may be a contrast agent concentration ratio calculated for the regions in each of which a coronary artery guarantees the blood flow, as well as a contrast agent concentration level that takes into account a change in the contrast agent concentration level in the thickness direction of the myocardium. For example, in the example illustrated in FIG. 13 (explained later), the region having a higher concentration level on the left end of the circle is a region where it is conjectured that the blood flow is not sufficiently reaching, when it is assumed that there is a correlation between the concentration index and the blood flow.

The setting unit 154 is configured to configure a setting into the calculating unit 153 in accordance with information input by the user via the input unit 29. For example, in accordance with an input from the user, the setting unit 154 sets a first region serving as an analysis target and a second region used for an identifying process performed on the first region, in the image data in the time series indicating the blood vessels of the subject. In the present example, the first region is set in a coronary artery, for instance, whereas the second region is set in the aorta, for instance.

The inverse analysis unit 155 is configured to output, to the first identifying unit 156, a mathematical model such as, for example, a polynomial expression used for analyzing the stenosis in a blood vessel or a multivariate statistical model. More specifically, the inverse analysis unit 155 outputs, to the first identifying unit 156, the mathematical model that makes it possible to perform an identifying process (an inverse analysis) to analyze the stenosis in the blood vessel, on the basis of the material model of the blood vessel, the boundary conditions for the entrance and the exit of the blood vessel serving as an analysis target, and the load condition.

In the third embodiment, the first identifying unit 156 is configured to identify a function index of the blood vessels of the subject, by further using a concentration change amount of the images.

More specifically, the first identifying unit 156 analyzes the stenosis in a blood vessel and, for example, estimates an FFR value, by using the mathematical model received from the inverse analysis unit 155, on the basis of the notion that the mathematical function of at least one of the plurality of indices extracted (calculated) by the calculating unit 153 has a strong correlation with a stenosis index (the FFR value). Alternatively, the first identifying unit 156 may estimate a pressure distribution and a flow amount distribution indicating a degree of the stenosis in the blood vessel (a degree of the blood flow obstruction). Alternatively, the index indicating the stenosis estimated by the first identifying unit 156 may express a change in the flow amount or a change in the pressure between an expansion time and a contraction time, a pressure loss between before and after the stenosis, a pressure loss between an aorta part and a coronary artery part, a flow amount ratio between coronary arteries (between a coronary artery having a stenosis and a coronary artery having no stenosis), or the like. In this situation, the first identifying unit 156 may be configured so as to judge the state of each of the blood vessels, by judging, for example, whether or not the index exceeds a predetermined threshold value.

The display controlling unit 157 is configured to cause the display unit 31 to display the result estimated by the first identifying unit 156. In other words, the display controlling unit 157 functions as an output unit configured to output the result estimated by the first identifying unit 156.

Figure 23:
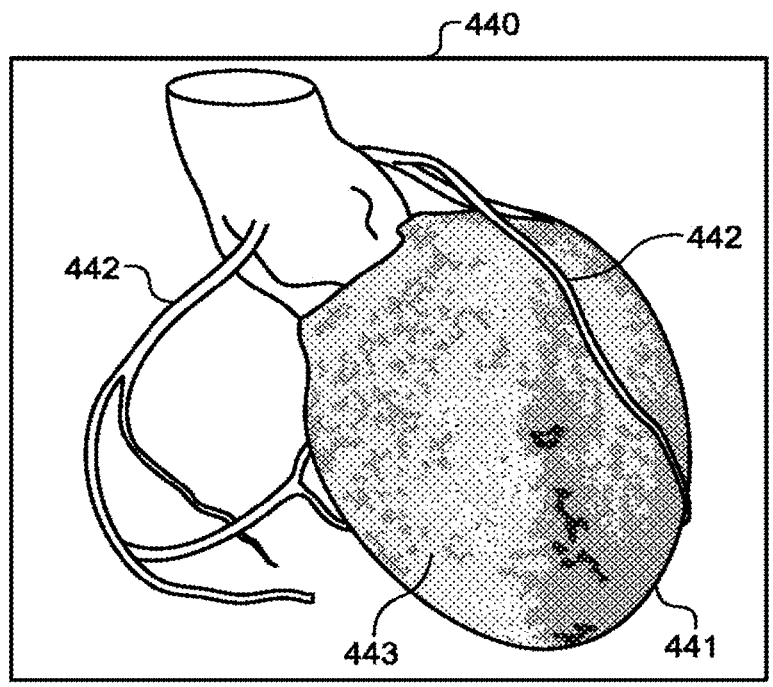
FIG. 23 is a drawing of another example of a reference image.

Next, examples of operations performed by the input unit 29 and the display unit 31 included in the medical image diagnosis apparatus will be explained. For example, after a blood vessel stenosis analysis has been performed by the medical image diagnosis apparatus, the display unit 31 displays a designation input screen in which an overall image of the heart and the blood vessels is displayed as a reference image as illustrated in FIG. 23 (explained later), and further displays a cursor on the designation input screen. The cursor moves in response to an operation by the user that is input via the input unit 29 and, for example, specifies a position in a coronary artery serving as an analysis target. When the position in the coronary artery has been specified via the input unit 29, the display unit 31 displays any of the analysis results explained later with reference to FIGS. 11 to 13, in response to an instruction received via the input unit 29.

Figure 11:
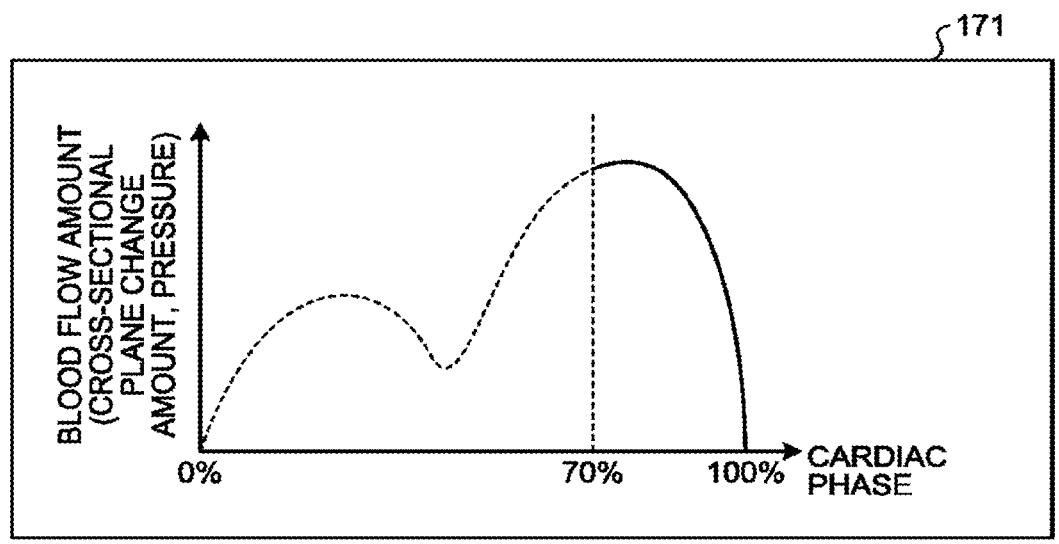
FIG. 11 is a drawing illustrating a display screen with a chart of a blood flow amount in a position in a coronary artery.

FIG. 11 is a drawing illustrating a display screen 171 with a chart of a blood flow amount in a position in a coronary artery specified on the designation input screen. As illustrated in FIG. 11, the display unit 31 displays changes in the blood flow amount (or the cross-sectional plane change amount or the pressure) with respect to changes in the cardiac phase in the position specified in the coronary artery.

Figure 12:
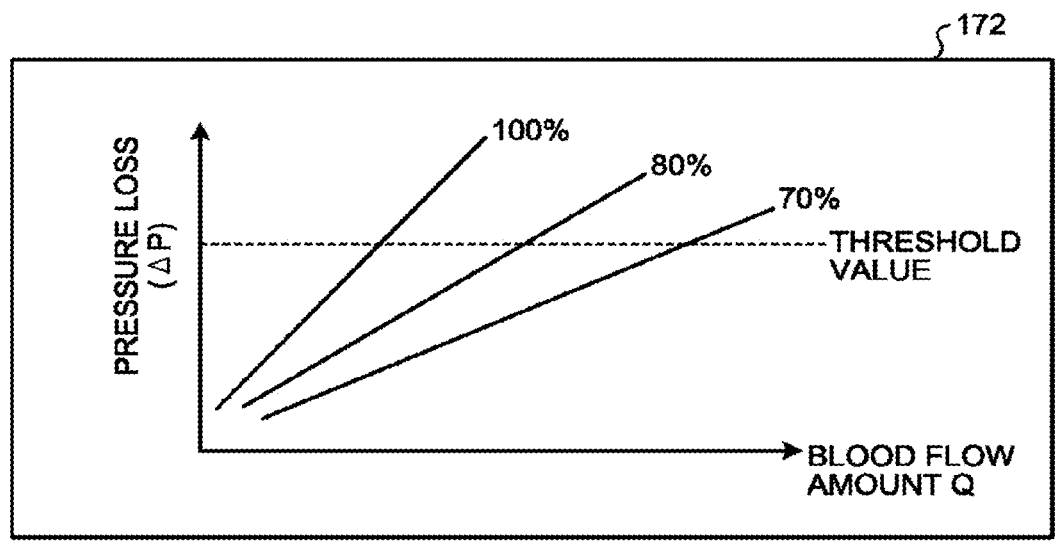
FIG. 12 is a drawing illustrating a display screen with a chart of pressure losses in a position in a coronary artery.

FIG. 12 is a drawing illustrating a display screen 172 with a chart of pressure losses (ΔP) in a position in the coronary artery specified on the designation input screen. As illustrated in FIG. 12, the display unit 31 displays changes in the pressure loss with respect to changes in a blood flow amount Q in the position specified in the coronary artery. Alternatively, the display unit 31 may be configured to display a threshold value used for judging whether the analysis result obtained by the blood vessel analyzing apparatus 150 is acceptable or not, together with the analysis result.

FIG. 13 is a drawing illustrating a display screen 173 with a contrast agent concentration map showing a developed view of heart walls including a region where the coronary artery specified on the designation input screen guarantees the blood flow. As illustrated in FIG. 13, the display unit 31 displays the contrast agent concentration map including the region where the specified coronary artery guarantees the blood flow.

A Modification Example of the Third Embodiment

Figure 14:
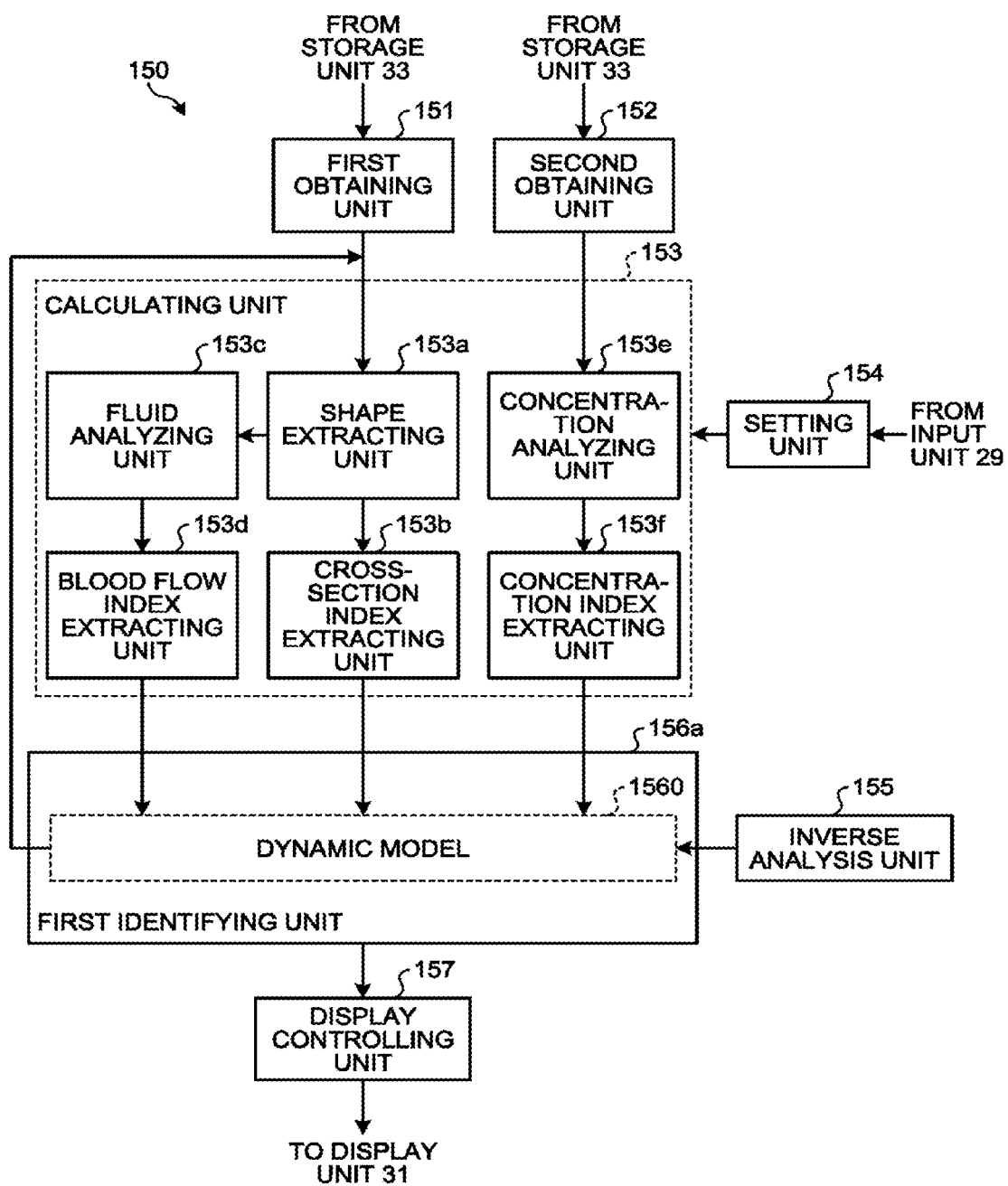
FIG. 14 is a functional block diagram of a modification example of the blood vessel analyzing apparatus according to the embodiment.

Next, a modification example of the blood vessel analyzing apparatus 150 will be explained. FIG. 14 is a functional block diagram illustrating functions in a modification example of the blood vessel analyzing apparatus 150. Some of the constituent elements of the functions in the modification example of the blood vessel analyzing apparatus 150 illustrated in FIG. 14 that are substantially the same as those of the functions in the blood vessel analyzing apparatus 150 illustrated in FIG. 10 are referred to by using the same reference characters. The first identifying unit 156a accomplishes the similar function as the first identifying unit 156 illustrated in FIG. 10, and the different portion of concrete processes according to the embodiments will be described mainly here.

The first identifying unit 156a includes a dynamic model 1560 and is configured to analyze a stenosis in a blood vessel and estimates, for example, an FFR value, by using the mathematical model received from the inverse analysis unit 155, on the basis of the notion that the mathematical function of at least one of the plurality of indices extracted (calculated) by the calculating unit 153 has a strong correlation with the stenosis index (the FFR value). The dynamic model 1560 may represent, for example, a structure analysis, a fluid analysis, a structure-fluid coupled analysis (a one-dimensional simplified mathematical model or a three-dimensional numerical value calculation model), or the like.

The dynamic model 1560 in this situation is the same as the one explained in the second embodiment. In the third embodiment, parameters related to latent variables such as a material model, a boundary condition, and a load condition are identified by an inverse analysis (a statistical identifying process) performed by the inverse analysis unit 155 on the basis of the dynamic model 1560. A precise latent variable identified by the inverse analysis is assigned to the dynamic model 1560. By using the dynamic model 1560 to which the precise latent variable is assigned, it is possible to perform a hemodynamic analysis based on a structural fluid analysis, a fluid analysis, a structure analysis, or an image analysis that takes into account impacts of external factors such as blood vessels and the heart positioned outside the analysis target blood vessel region to be made on the analysis target blood vessel region.

Further, in relation to the construction of the dynamic model 1560, the blood vessel analyzing apparatus 150 is able to solve the following four difficulties by identifying the latent variable by performing the inverse analysis: The first difficulty is in the method for identifying a material model of a coronary artery. The second difficulty is in incorporating impacts of deformation in the shape of the heart to be made on a coronary artery. The third difficulty is in the method for identifying a boundary condition for a coronary artery. The fourth difficulty is in performing an image analysis or a structural fluid analysis by using the shape of a blood vessel that has variances caused by the uncertainty of medical image data. By overcoming these four difficulties, the blood vessel analyzing apparatus 150 is able to realize an improvement in the precision level of the analysis, compared to conventional blood vessel structural fluid analyses in which the latent variables are not identified by performing an inverse analysis.

The blood vessel analyzing apparatus 150 may be configured as described below.

The blood vessel analyzing apparatus may be configured so that the setting unit sets the first region in a range apart from the coronary artery starting part by a predetermined distance on the downstream side thereof and sets the second region in a range apart from the aorta starting part by a predetermined distance on the aortic arch side.

The blood vessel analyzing apparatus may be configured so that the calculating unit calculates a change amount of each of the cross-sectional planes of the blood vessel in the first region and the second region, within a time period including an expansion and a contraction of a coronary vein during an expansion period of the left ventricle.

Further, the blood vessel analyzing apparatus may be configured so as to include an identifying unit configured to estimate an index of a blood flow on the basis of image data indicating a blood vessel of a subject and so as to further include an input unit configured to receive an input for specifying the first region set by the setting unit and an output unit configured to output at least one selected from among a change amount of a cross-sectional plane, a change amount in the blood flow resistance, and a change amount in the concentration of the image data calculated by the calculating unit or at least one selected from among a pressure level, a flow amount, and an FFR value of the blood in the first region, and a pressure level of the blood vessel wall estimated by the identifying unit.

Fourth Embodiment

Next, a fourth embodiment will be explained.

An image processing apparatus according to a fourth embodiment is configured, with respect to a blood vessel region included in images in a time series, to set a first cross-sectional plane of a blood vessel having a stenosis on the downstream side of the stenosis and to set a second cross-sectional plane of a blood vessel having no stenosis. Further, the image processing apparatus is configured to calculate blood vessel morphology indices in a time series, for each of the first and the second cross-sectional planes that were set and to further calculate a blood vessel cross-sectional shape change index for each of the first and the second cross-sectional planes on the basis of the calculated blood vessel morphology indices. After that, the image processing apparatus is configured to identify a function index of the blood vessel of the subject, by using the blood vessel cross-sectional shape change indices of the first and the second cross-sectional planes, as physical indices.

For instance, examples of methods for identifying a stenosis in a blood vessel include a method by which a stenosis index is analyzed by performing a structural fluid simulation that utilizes a three-dimensional analysis model, while using CT images. When this method is used, there may be some situations where it takes an extremely long calculation time to analyze a stenosis index. By using the configuration described above, however, it is possible to identify the function index of the blood vessel at a high speed, by identifying the function index of the blood vessel, on the basis of the blood vessel cross-sectional shape change indices of the cross-sectional plane of the blood vessel having a stenosis that is set on the downstream side of the stenosis and the cross-sectional plane that is set in the blood vessel having no stenosis.

A configuration of the medical image diagnosis apparatus according to the fourth embodiment is the same as that illustrated in FIG. 1. Thus, the explanation thereof will be omitted. The image processing apparatus 27 according to the fourth embodiment will be explained below, while a focus is placed on differences from the first embodiment.

In the fourth embodiment, with respect to the blood vessel region included in the images, the first setting unit is configured to set the first cross-sectional plane of the blood vessel having the stenosis on the downstream side of the stenosis and to set the second cross-sectional plane of the blood vessel having no stenosis. Further, with respect to each of the first and the second cross-sectional planes, the first calculating unit is configured to calculate the blood vessel morphology indices in the time series and to further calculate the blood vessel cross-sectional shape change indices for the first and the second cross-sectional planes on the basis of the calculated blood vessel morphology indices. Further, the first identifying unit is configured to identify the function index of the blood vessel of the subject, by using the blood vessel cross-sectional shape change indices of the first and the second cross-sectional planes as the physical indices.

In the fourth embodiment, the storage unit 65 has stored therein, as the correlation information, a one-dimensional mathematical model related to dynamics. In this situation, for example, the physical indices are the blood vessel cross-sectional shape change indices. More specifically, the blood vessel cross-sectional shape change indices each indicate a change amount in the radius of the blood vessel cross-sectional plane of a coronary artery. Further, the function index may be, for example, a Fractional Flow Reserve (FFR) value.

In other words, in the fourth embodiment, the storage unit 65 has stored therein the one-dimensional mathematical model related to dynamics that indicates a correlational relationship among the radius of the blood vessel cross-sectional plane of the coronary artery, the change amount in the radius, the wall thickness, and the FFR value. For example, the mathematical model in this situation is defined by using a one-dimensional material dynamic model indicating pressure levels and changes in the cross-sectional area of the coronary artery and a one-dimensional fluid dynamic model indicating pressure losses in the coronary artery.

For example, the one-dimensional material dynamic model indicating the pressure levels and the changes in the cross-sectional area of the coronary artery can be expressed by using Expressions (1) and (2) shown below:

$$P = \frac{4}{3}\frac{Eh}{r_0}\left(1 - \sqrt{\frac{A_0}{A}}\right) \quad (1)$$
$$= \frac{4}{3}\frac{Eh}{r_0}\left(1 - \frac{r_0}{r}\right)$$

$$dp = \frac{dp(r)}{dr}dr \quad (2)$$
$$= \frac{4}{3}\frac{Eh}{r^2}dr$$

In the expressions above, p denotes the pressure in the coronary artery, whereas E denotes a modulus of elasticity of the coronary artery. Further, A and $A_0$ denote the cross-sectional areas of a blood vessel cross-sectional plane of the coronary artery at two points in time; r and $r_0$ denote the radii of the cross-sectional plane of the blood vessel at the two points in time; and dr denotes the change amount between the radii of the blood vessel cross-sectional plane. Further, h denotes the wall thickness at the blood vessel cross-sectional plane of the coronary artery.

Further, for instance, the one-dimensional fluid dynamic model indicating the pressure losses of the coronary artery can be expressed by, for example, using Expressions (3) to (7) shown below:

$$p_1 - p_0 = R_1 Q_1 \quad (3)$$

$$dp_1 = R_1 dQ_1 \quad (4)$$

$$dp_3 = R_2 dQ_2 \quad (5)$$

$$p_1 = R_n Q_2^2 + p_3 \quad (6)$$

$$dp_1 = 2R_n Q_2 dQ_2 + dp_3 \quad (7)$$

In the expressions above, $p_0$ and $p_1$ denote the pressure levels of the two blood vessel cross-sectional planes; $dp_1$ denotes a pressure loss of the first cross-sectional plane of the coronary artery; and $dp_1$ denotes a pressure loss of the second cross-sectional plane of the coronary artery. Further, $R_1$ denotes a blood flow resistance of the first cross-sectional plane of the coronary artery; and $R_2$ denotes a blood flow resistance of the second cross-sectional plane of the coronary artery. Further, $Q_1$ denotes a blood flow amount at the first cross-sectional plane of the coronary artery; and $Q_2$ denotes a blood flow amount at the second cross-sectional plane of the coronary artery.

On the basis of Expressions (3) to (7) above, an FFR value can be expressed by using a mathematical model shown in Expression (8) below.

$$FFR = \frac{R_2 Q_2}{R_n Q_2^2 + R_2 Q_2} \quad (8)$$
$$= \frac{R_2}{R_n Q_2 + R_2}$$
$$= \frac{R_2 dQ_2}{R_n Q_2 dQ_2 + R_2 dQ_2}$$
$$= 2\frac{dp_3}{dp_1 + dp_3}$$
$$= 2\frac{Eh_3 \frac{dr_3}{r_3^2}}{Eh_1 \frac{dr_1}{r_1^2} + Eh_3 \frac{dr_3}{r_3^2}}$$
$$= 2\frac{h_3 r_1^2 dr_3}{h_1 r_3^2 dr_1 + h_3 r_1^2 dr_3}$$

By using the mathematical model shown above, if the radii $r_1$ and $r_3$, the change amounts $dr_1$ and $d_{r3}$ of the radii, and the wall thicknesses $h_1$ and $h_3$ of the two blood vessel cross-sectional planes are available, it is possible to obtain a single FFR value.

Further, in the fourth embodiment, the obtaining unit 69 is configured to obtain images in a time series including images of a blood vessel of a subject and the correlation information indicating a correlational relationship between the physical indices of the blood vessel and the function indices of the blood vessel related to vascular hemodynamics. More specifically, the obtaining unit 69 obtains the CT images in the time series including the images of the blood vessel of the subject, from the storage unit 65. For example, the obtaining unit 69 obtains the CT images of a ventricle expansion region corresponding to a range of the cardiac phases of 70 to 100%, from among the cardiac phases (0 to 100%) in one heartbeat of the heart. In this situation, the obtaining unit 69 obtains the CT images corresponding to two or more cardiac phases. Further, in the fourth embodiment, the obtaining unit 69 obtains, as the correlation information, a one-dimensional mathematical model that is related to dynamics and that indicates a correlational relationship between the radius of a blood vessel cross-sectional plane of a coronary artery, a change amount in the radius, the wall thickness, and an FFR value, from the storage unit 65.

Further, in the fourth embodiment, with respect to a blood vessel region included in the CT images in the time series obtained by the obtaining unit 69, the first setting unit 51 is configured to set the first cross-sectional plane of a blood vessel having a stenosis on the downstream side of the stenosis and to set the second cross-sectional plane of a blood vessel having no stenosis. For example, the first setting unit 51 sets the first cross-sectional plane in the vicinity of a distal part of a coronary artery having a stenosis and sets the second cross-sectional plane in the vicinity of a starting part of a coronary artery having no stenosis.

For example, on the basis of an indication of a position received from the operator via the input unit 29, the first setting unit 51 sets the first cross-sectional plane and the second cross-sectional plane. More specifically, for example, on the designation input screen displaying an overall image of the heart and the blood vessels as a reference image as illustrated in FIG. 23 (explained later), the first setting unit 51 receives, from the operator, an operation to designate a desired position in the vicinity of the distal part of the coronary artery having a stenosis and further sets the first cross-sectional plane in the received position. Further, on the designation input screen displaying the overall image of the heart and the blood vessels as the reference image as illustrated in FIG. 23, the first setting unit 51 receives, from the operator, an operation to designate a desired position in the blood vessel having no stenosis via the input unit 29 and further sets the second cross-sectional plane in the received position.

Further, for example, the first setting unit 51 may automatically set the first cross-sectional plane and the second cross-sectional plane by analyzing the CT images in the time series obtained by the obtaining unit 69. More specifically, for example, by analyzing the CT images in the time series, the first setting unit 51 specifies the coronary artery having a plaque and the coronary artery having no plaque. Further, the first setting unit 51 sets a first region in the coronary artery having the plaque in such a position that is away from the plaque by a predetermined distance on the downstream side thereof. Further, the first setting unit 51 sets a second region in the coronary artery having no plaque in such a position that is away from the starting part of the coronary artery by a predetermined distance on the downstream side thereof.

Figure 15:
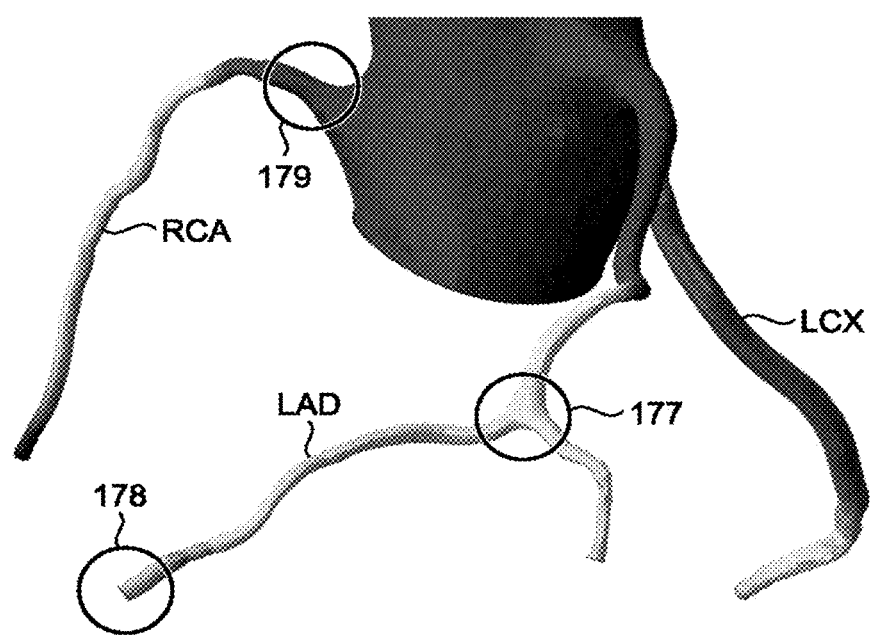
FIG. 15 is a drawing illustrating examples of setting a first cross-sectional plane and a second cross-sectional plane.

FIG. 15 is a drawing illustrating examples of setting the first cross-sectional plane and the second cross-sectional plane. For example, as illustrated in FIG. 15, let us assume that, for example, the left anterior descending coronary artery (LAD) has a stenosis part 177, whereas the right coronary artery (RCA) and the left circumflex coronary artery (LCX) each have no stenosis.

In that situation, for example, the first setting unit 51 sets a first cross-sectional plane in the vicinity 178 of a distal part of the LAD. Further, for example, the first setting unit 51 sets a second cross-sectional plane in the vicinity 179 of a starting part of the RCA. More specifically, for example, the first setting unit 51 sets the second cross-sectional plane within a range of 20 mm from the starting part of the RCA, as the cross-sectional plane in the vicinity of the starting part of the coronary artery. Alternatively, in the present example, the first setting unit 51 may set a second cross-sectional plane in the LCX. In another example, the first setting unit 51 may set a second cross-sectional plane within a range of 5 to 20 mm on the downstream side of the aorta, as the cross-sectional plane in the vicinity of the starting part of the coronary artery.

Further, in the fourth embodiment, the first calculating unit 67 is configured to calculate blood vessel morphology indices in a time series indicating morphology of a blood vessel of the subject, on the basis of the CT images in the time series obtained by the obtaining unit 69. In the fourth embodiment, the first calculating unit 67 calculates the blood vessel morphology indices in the time series for each of the first and the second cross-sectional planes set by the first setting unit 51. Further, in the fourth embodiment, the first calculating unit 67 calculates a blood vessel cross-sectional shape change index of each of the first and the second cross-sectional planes, on the basis of the calculated blood vessel morphology indices. In this situation, for example, the blood vessel morphology indices each indicate the radius and the wall thickness of each of the blood vessel cross-sectional planes. Further, the blood vessel cross-sectional shape change indices each indicate a change amount in the radius of each of the blood vessel cross-sectional planes.

Further, in the fourth embodiment, the first identifying unit 66 is configured to identify a function index of a blood vessel of the subject, by using a physical index of the blood vessel of the subject obtained from a blood vessel morphology index, on the basis of the correlation information. In the fourth embodiment, the first identifying unit 66 identifies the function index of the blood vessel of the subject, by using the blood vessel cross-sectional shape change index of each of the first and the second cross-sectional planes, as physical indices. More specifically, by using the one-dimensional mathematical model related to dynamics obtained by the obtaining unit 69, the first identifying unit 66 identifies an FFR value, on the basis of the radius of the blood vessel cross-sectional plane, the change amount in the radius, and the wall thickness on each of the first and the second cross-sectional planes calculated by the first calculating unit 67.

Figure 16:
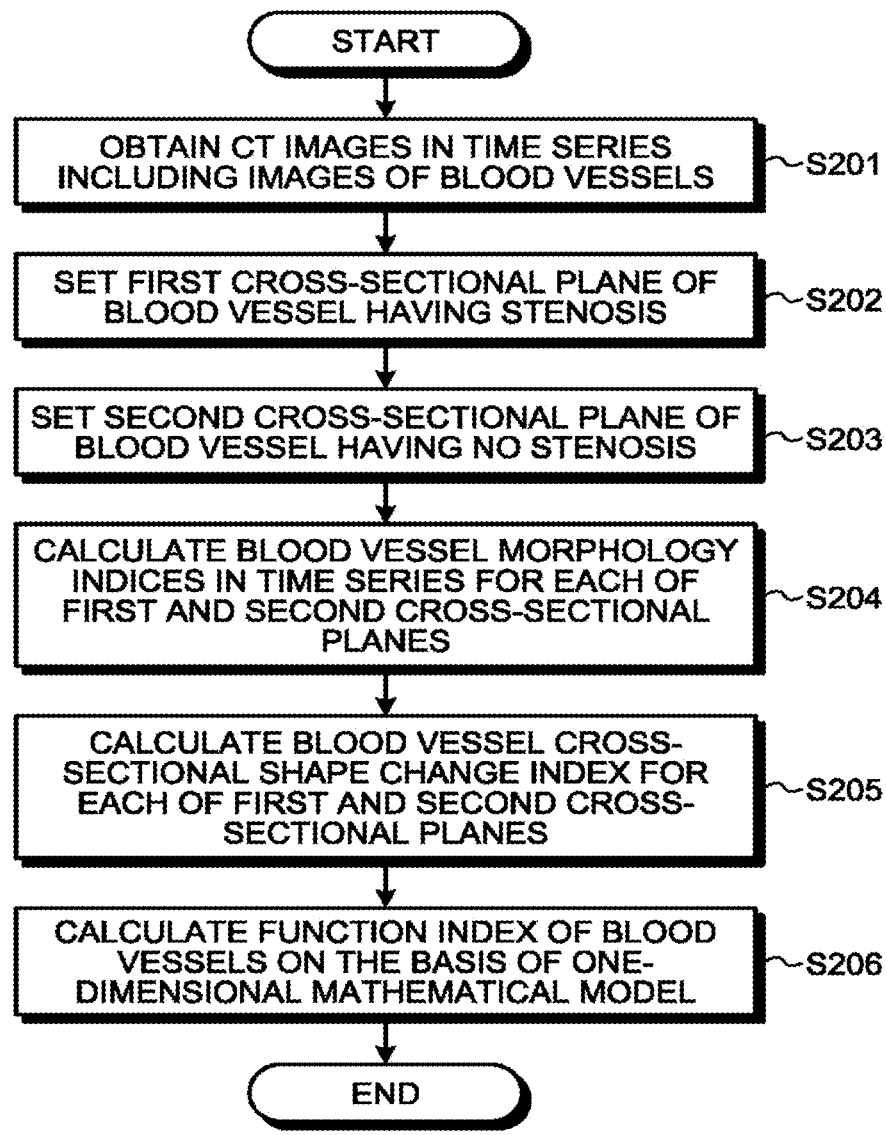
FIG. 16 is a flowchart of a flow in a blood vessel analyzing process.

Next, a flow in a blood vessel analyzing process performed by the image processing apparatus 27 according to the fourth embodiment will be explained. FIG. 16 is a flowchart of the flow in the blood vessel analyzing process performed by the image processing apparatus 27.

As illustrated in FIG. 16, in the image processing apparatus 27 according to the fourth embodiment, the obtaining unit 69 first obtains the CT images in the time series including images of blood vessels of the subject from the storage unit 65 (step S201).

Subsequently, with respect to a blood vessel region included in the obtained CT images in the time series, the first setting unit 51 sets the first cross-sectional plane in the blood vessel having a stenosis on the downstream side of the stenosis (step S202) and sets the second cross-sectional plane in the blood vessel having no stenosis (step S203).

Subsequently, the first calculating unit 67 calculates the blood vessel morphology indices in the time series for each of the first and the second cross-sectional planes that were set (step S204). Further, the first calculating unit 67 calculates the blood vessel cross-sectional shape change index for each of the first and the second cross-sectional planes, on the basis of the calculated blood vessel morphology indices (step S205). For example, the first calculating unit 67 calculates the radius and the wall thickness of the blood vessel cross-sectional planes as the morphology indices and calculates the change amount in the radius of each of the blood vessel cross-sectional planes as the blood vessel cross-sectional shape change indices.

Subsequently, the first identifying unit 66 calculates the function index of the blood vessels from the blood vessel cross-sectional shape change index of each of the first and the second cross-sectional planes, on the basis of the one-dimensional mathematical model related to dynamics obtained by the obtaining unit 69 (step S206). For example, the first identifying unit 66 identifies an FFR value as the function index.

As explained above, according to the fourth embodiment, it is possible to identify the function index of the blood vessel at a high speed, by identifying the function index of the blood vessel on the basis of the blood vessel cross-sectional shape change indices of the cross-sectional plane that is set in the blood vessel having a stenosis on the downstream side of the stenosis and the cross-sectional plane that is set in the blood vessel having no stenosis.

Further, according to the fourth embodiment, the function index of the blood vessel is identified from the CT images in the time series, on the basis of the one-dimensional mathematical model related to dynamics. Consequently, compared to, for example, a situation where a stenosis index is analyzed by performing a structural fluid simulation that utilizes a three-dimensional analysis model, it is possible to identify the function index of the blood vessel at a higher speed.

Fifth Embodiment

Next, a fifth embodiment will be explained.

An image processing apparatus according to the fifth embodiment is configured to cause a display unit to display information indicating an identified function index of a blood vessel of a subject.

In this configuration, the function index of the blood vessel of the subject related to vascular hemodynamics is identified and displayed, from the medical images in the time series indicating a blood vessel of the subject and an organ to which blood is supplied by the blood vessel. Consequently, according to the fifth embodiment, it is possible to aid a diagnosis process to evaluate hematogenous ischemia in the blood vessel.

A configuration of the medical image diagnosis apparatus according to the fifth embodiment is the same as that illustrated in FIG. 1. Thus, the explanation thereof will be omitted. An image processing apparatus according to the fifth embodiment will be explained below.

The image processing apparatus according to the fifth embodiment is configured to identify the function index of the blood vessel of the subject related to vascular hemodynamics such as stenosis, on the basis of the medical images in the time series and the correlation information and to cause the display unit 31 to further display the identified function index. In the fifth embodiment, an example will be explained in which CT images in a time series are used as the medical images. In this situation, the CT images in the time series are represented by data that expresses a three-dimensional spatial distribution of CT values in a time series. For example, the CT images in the time series include approximately twenty images in one heartbeat, i.e., CT images corresponding to approximately twenty cardiac phases.

The medical images in the time series in this situation do not necessarily have to be CT images and may be any images from which it is possible to observe a change in the shape of an organ and a blood vessel during at least one heartbeat. For example, the medical images may be MRI images, ultrasound images, three-dimensional (3D) angiography images, Intravascular Ultrasound (IVUS) images, or the like. Further, the CT images may be taken by performing a conventional imaging process while using an Area Detector CT (ADCT) apparatus or may be taken by performing a helical scan while using an ADCT apparatus or a helical CT apparatus.

In the fifth embodiment, the image processing apparatus further includes a display controlling unit. The display controlling unit is configured to cause the display unit to display the information indicating the function index of the blood vessel of the subject. Further, a calculating unit is configured to calculate, as the blood vessel morphology index, either a cross-sectional area or a unit volume of the blood vessel of the subject. After that, the display controlling unit causes the display unit to further display a change curve indicating a chronological change in either the cross-sectional area or the unit volume. In the fifth embodiment, the image processing apparatus includes a first calculating unit and a third calculating unit as calculating units.

Figure 17:
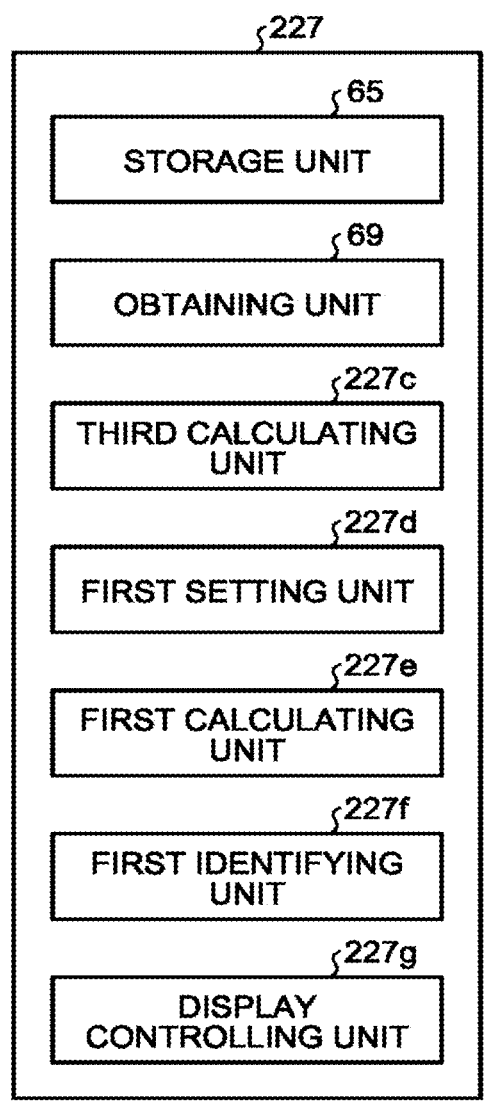
FIG. 17 is a functional block diagram of an exemplary configuration of an image processing apparatus.

FIG. 17 is a functional block diagram of an exemplary configuration of an image processing apparatus according to the fifth embodiment. For example, as illustrated in FIG. 17, an image processing apparatus 227 according to the fifth embodiment includes the storage unit 65, the obtaining unit 69, a third calculating unit 227c, a first setting unit 227d, a first calculating unit 227e, a first identifying unit 227f, and a display controlling unit 227g. In the present example, some of the constituent elements that have substantially the same functions as those illustrated in FIG. 2 will be referred to by using the same reference characters, and detailed explanations thereof will be omitted. The first setting unit 227d, the first calculating unit 227e, and the first identifying unit 227f accomplish the similar functions as the first setting unit 51, the first calculating unit 67 and the first identifying unit 66 illustrated in FIG. 2, and the different portion of concrete processes according to the embodiments will be described mainly here.

In this situation, a part or all of the obtaining unit 69, the first setting unit 227d, the third calculating unit 227c, the first calculating unit 227e, the first identifying unit 227f, and the display controlling unit 227g may be realized, for example, by causing a processing apparatus such as a CPU to execute a program (i.e., realized by software), or may be realized by hardware such as an IC, or may be realized by both software and hardware.

The third calculating unit 227c is configured to calculate the blood vessel morphology indices in the time series indicating morphology of the blood vessel of the subject, on the basis of the images in the time series obtained by the obtaining unit 69. For example, the third calculating unit 227c calculates the blood vessel morphology indices in the time series by performing an image analyzing process on the CT images in the time series.

In this situation, when performing the image analyzing process, the third calculating unit 227c detects an organ region and a blood vessel region from the CT images in the time series, by using a method such as segmentation or the like. Further, from the obtained blood vessel region, the third calculating unit 227c detects a central line indicating the blood vessel extending direction, as well as the internal wall and the external wall of the blood vessel. Further, as the blood vessel morphology indices, the third calculating unit 227c specifies three-dimensional coordinates of the pixels corresponding to the vascular lumen, the blood vessel wall, and a plaque region within the blood vessel region.

As noted above, the blood vessel morphology indices do not necessarily have to be the three-dimensional coordinates, but may be geometric indices such as the radius or the diameter of the vascular lumen for every certain angle on a cross-sectional plane in a uniaxial direction perpendicular to the central line and a directional vector at 0°, or an average area or an average radius with respect to all the angles on a cross-sectional plane, or the volume of the vascular lumen defined by a plurality of short-axis cross-sectional planes perpendicular to the central line direction, or a blood vessel wall volume or a plaque volume defined by a plurality of cross-sectional planes perpendicular to the plane of the vascular lumen.

Further, the third calculating unit 227c is configured to bring positions in the organ and the blood vessel that are anatomically the same as one another among a plurality of cardiac phases into correspondence with one another. For example, the third calculating unit 227c brings the same positions in the blood vessel and the organ into correspondence with one another, by performing a pattern matching process or a position alignment process on a blood vessel region and an organ region that were separated as segments from each of the CT images in the time series.

At this time, for example, the third calculating unit 227c establishes one of a plurality of cardiac phases as a reference phase, and establishes the CT image in the reference phase as a reference image. The third calculating unit 227c then aligns the positions of blood vessels and organs in the images in the other cardiac phases to those in the reference image. The reference phase is, for example, a cardiac phase in which the movements of the coronary arteries are minimized, and the CT image in the reference phase can be extracted by estimating the amount of motion artifacts in the CT image. Further, the reference phase may be a cardiac phase detected as that of which the amount of offset of the coronary arteries is smallest among each cardiac phase, or may be a cardiac phase arbitrarily selected and set by an operator. Alternatively, the reference phase may be a cardiac phase in which the best contrast of the CT image is achieved, or a cardiac phase in which the standard deviation (SD) of the CT images is minimized. Further alternatively, the reference phase may be a cardiac phase of an arbitrary time point, such as a cardiac phase of 70% when one heartbeat is divided into cardiac phases of 0% to 100%.

Further, for example, the third calculating unit 227c sets a plurality of tracked points such as an anatomical feature point or feature shape, a representative point, a pixel, or the like in the organ and the blood vessel, according to an instruction from the operator via the input unit 29 or through an image processing process. For example, the third calculating unit 227c sets a set of tracked points of a feature shape or the like, at a blood vessel branching part or on the surface. Further, the third calculating unit 227c brings the anatomically same positions in the organ and the blood vessel during a plurality of heartbeats into correspondence with one another, on the basis of displacement data of the set of tracked points obtained from a tracking process performed at mutually-different points in time (in mutually-different cardiac phases).

After that, the third calculating unit 227c calculates the blood vessel morphology indices in the time series indicating the morphology of the blood vessel of the subject, on the basis of the CT images in the time series.

In the fifth embodiment, the third calculating unit 227c calculates either the cross-sectional area or the unit volume of the blood vessel of the subject, as the blood vessel morphology indices. For example, as the cross-sectional area or the unit volume of the blood vessel, the third calculating unit 227c calculates the cross-sectional area or the unit volume of either the lumen or the internal wall of the blood vessel.

The first setting unit 227d is configured to set a measuring point indicating a site at which a second function index is to be measured, in the blood vessel region indicating the blood vessel of the subject included in the CT images.

In the fifth embodiment, the first setting unit 227d sets the measuring point at a designated point designated by the operator via the input unit 29, in the blood vessel region indicating the blood vessel of the subject. For example, in the blood vessel region, the first setting unit 227d sets measuring points at a plurality of designated points designated by the operator.

For example, in the blood vessel region, the first setting unit 227d sets the measuring points in a designated site and a reference site, as a result of an operation or an automatic process performed by the apparatus. In this situation, for example, the designated site is set at a site in the blood vessel region which the operator wishes to evaluate, such as a lesion site where a pathological issue (e.g., a stenosis) has occurred. Further, for example, the reference site is set at a site in the blood vessel region which the operator wishes to compare with the designated site, such as a normal site where no pathological issue has occurred.

Alternatively, for example, the first setting unit 227d may set a plurality of designated points at regular intervals as the measuring points, in the blood vessel region indicating the blood vessel of the subject. The intervals between the points may be predetermined so as to be set by the apparatus or may be designated by the operator every time a measuring point setting process is performed.

The first calculating unit 227e is configured to calculate the second physical index of the blood vessel, on the basis of the blood vessel morphology indices in the time series calculated by the third calculating unit 227c. More specifically, the first calculating unit 227e calculates the second physical index at the measuring points set by the first setting unit 227d, on the basis of the blood vessel morphology indices in the time series calculated by the third calculating unit 227c. The definition of the second physical index is the same as the first physical indices. In the following explanations, when not distinguished from each other, the first and the second physical indices may simply be referred to as physical indices.

For example, the first calculating unit 227e calculates, as the second physical index, a second physical index of the same type as the first physical indices indicated by the correlation information stored in the storage unit 65. For example, let us assume that the storage unit 65 has stored therein the first correlation information illustrated in FIG. 4A and the second correlation information illustrated in FIG.

4B. In that situation, the first calculating unit 227e calculates, as a second physical index, at least one selected from between a blood vessel cross-sectional shape change index and a blood flow resistance index at each of the measuring points.

The second physical index calculated by the first calculating unit 227e does not necessarily have to be the blood vessel cross-sectional shape change index and the blood flow resistance index, as long as the second physical index is of the same type as the first physical indices indicated by the correlation information stored in the storage unit 65. Further, when the storage unit 65 has stored therein a plurality of pieces of correlation information, the first calculating unit 227e may calculate a second physical index of a type that is indicated by at least one of the plurality of pieces of correlation information.

In the fifth embodiment, an example will be explained in which the storage unit 65 has stored therein the first correlation information illustrated in FIG. 4A and the second correlation information illustrated in FIG. 4B. In that situation, for example, the first calculating unit 227e calculates, as second physical indices, a blood flow resistance index and a blood vessel cross-sectional shape change index.

In the fifth embodiment, the first calculating unit 227e calculates, as the second physical index, the blood vessel cross-sectional shape change index indicating a chronological change in the blood vessel morphology indices. For example, the first calculating unit 227e calculates a change curve indicating a chronological change in either the cross-sectional area or the unit volume of the blood vessel, as the blood vessel cross-sectional shape change index.

The first calculating unit 227e may calculate, for example, the second physical index only for some or one of the cardiac phases corresponding to the CT images in the time series, instead of calculating the second physical index for each of the cardiac phases. Specifically, the first calculating unit 227e calculates the second physical index for some or one of the cardiac phases corresponding to the CT images in the time series, on the basis of the blood vessel morphology indices corresponding to the some or one of the cardiac phases. For example, when calculating the second physical index for one cardiac phase, the first calculating unit 227e calculates the second physical index on the basis of the blood vessel morphology indices of a predetermined number of cardiac phases including the one cardiac phase. For example, the first calculating unit 227e calculates the second physical index only for the reference phase mentioned above. In this case, for example, the first calculating unit 227e calculates the second physical index on the basis of the blood vessel morphology indices of a predetermined number of cardiac phases including the reference phase.

Further, for example, the first calculating unit 227e may specify the cardiac phase to be used in calculating the second physical index for each of a plurality of blood vessels, and calculate the second physical index for the specified cardiac phase. For example, the first calculating unit 227e specifies, for each of a plurality of blood vessels, the cardiac phase in which the movement of the blood vessel is minimized, and calculates the second physical index on the basis of the blood vessel morphology indices corresponding to the specified cardiac phase. Generally, the left coronary artery and the right coronary artery exhibit slightly different movements, and the blood flows into these arteries at slightly different timing. The first calculating unit 227e may therefore specify an appropriate cardiac phase for each of the left coronary artery and the right coronary artery, for example, and calculate the second physical index for each of the specified cardiac phases. The first calculating unit 227e may also calculate the second physical index for each main branch of the coronary arteries. For example, the first calculating unit 227e may calculate the second physical index for each of the left anterior descending (LAD), the right coronary artery (RCA), and the left circumflex artery (LCX).

As explained above, because the cardiac phases for which the second physical index is calculated are narrow down to some or one of the cardiac phases, information necessary for diagnosis (i.e., a function index in a specific cardiac phase) can be obtained in a short time.

The first identifying unit 227f is configured to identify the second function index of the blood vessel of the subject related to vascular hemodynamics, on the basis of the correlation information stored in the storage unit 65 and at least one selected from between the blood vessel morphology indices and the second physical index of the blood vessel of the subject obtained from the blood vessel morphology indices.

More specifically, the first identifying unit 227f identifies the second function index on the basis of the correlation information and the second physical index obtained from the blood vessel morphology indices in the time series. Even more specifically, the first identifying unit 227f identifies the second function index at each of the measuring points, on the basis of the correlation information and the second physical index calculated by the first calculating unit 227e.

For example, the first identifying unit 227f identifies, as the second function index at each of the measuring points, such a first function index from the correlation information that corresponds to a first physical index equal to the second physical index calculated by the first calculating unit 227e. The first physical index from the correlation information that is equal to the second physical index calculated by the first calculating unit 227e denotes such a first physical index from the correlation information that is of the same type as, and has the same value as, the second physical index.

To explain further in detail, let us discuss an example in which the storage unit 65 has stored therein the first correlation information illustrated in FIG. 4A. In that situation, the first identifying unit 227f identifies a pressure index corresponding to the blood vessel cross-sectional shape change index of the coronary artery calculated by the first calculating unit 227e, as the second function index at a measuring point. Consequently, the image processing apparatus 227 is able to identify the second function index of the blood vessel of the subject related to vascular hemodynamics in the non-invasive manner and at a high speed, without the need to perform a process that uses a dynamic model of a structural fluid analysis or the like and that takes a long processing time.

In the fifth embodiment, the first identifying unit 227f identifies a propagation speed of the blood flowing through the blood vessel of the subject, as a second function index. For example, the first identifying unit 227f identifies the propagation speed of the blood, on the basis of the change curve indicating the chronological change in either the cross-sectional area or the unit volume of the blood vessel calculated by the first calculating unit 227e.

For example, the first identifying unit 227f compares change curves between the designated site designated by the operator and the reference site and further calculates the propagation speed of the blood flowing between the designated site and the reference site, on the basis of the time difference between a temporal phase at a peak point in one of the change curves and a temporal phase at a peak point in the other change curve, as well as the distance between the designated site and the reference site. Alternatively, for example, the first identifying unit 227f may calculate the propagation speed of the blood, by performing a deconvolution process that uses a mathematical propagation function.

Further, in the fifth embodiment, the first identifying unit 227f identifies, as a second function index, at least one selected from between a pressure loss and a pressure loss ratio of the blood vessel of the subject. In addition, the first identifying unit 227f further identifies a flow amount of the blood vessel of the subject, as a second function index.

Further, in the fifth embodiment, the first identifying unit 227f identifies the second function index with respect to the measuring points designated by the operator in the blood vessel region indicating the blood vessel of the subject. For example, the first identifying unit 227f identifies a second function index for each of the measuring points designated by the operator in the blood vessel region indicating the blood vessel of the subject.

For example, the first identifying unit 227f identifies a second function index of the designated site designated by the operator and of the reference site, in the blood vessel region. Alternatively, for example, the first identifying unit 227f may identify a second function index for each of a plurality of measuring points set at regular intervals in the blood vessel region.

Alternatively, the first identifying unit 227f may identify the second function index by using the following method: For example, the first identifying unit 227f first performs a Monte Carlo simulation while varying the value to be set for the ex-ante distribution of the latent variable until the identification ending condition is satisfied, while limiting the value of the ex-ante distribution of the latent variable to the probability distribution (an expected range of possible values of the latent variable corresponding to the first function indices), indicated by the first function indices obtained from the correlation information. As a result of this process, the first identifying unit 227f identifies an ex-post distribution of the latent variable. Further, the first identifying unit 227f identifies the second function index at the measuring point from an identified value in the ex-post distribution.

In this situation, when the identified value in the ex-post distribution of the latent variable is a value indicating a function index, the first identifying unit 227f may identify the identified value as the second function index. For example, when the identified value in the ex-post distribution of the latent variable is a pressure ratio, the first identifying unit 227f identifies the pressure ratio as the second function index.

Alternatively, the first identifying unit 227f may identify the second function index at each of the measuring points by using a dynamic model. In that situation, the first identifying unit 227f constructs the dynamic model, by assigning the identified value in the ex-post distribution of the latent variable that was identified, to a shape model. Further, the first identifying unit 227f identifies the second function index at each of the measuring points by performing either a blood vessel stress analysis or a blood fluid analysis on the constructed dynamic model. The shape model and the dynamic model in this situation are the same as those explained in the second embodiment.

Further, as noted above, when the first calculating unit 227e calculates the second physical index for some or one of the cardiac phases, the first identifying unit 227f identifies the second function index for the corresponding some or one of the cardiac phases.

The display controlling unit 227g is configured to cause the display unit 31 to display information indicating the second function index identified by the first identifying unit 227f. Further, the display controlling unit 227g is configured to cause the display unit 31 to further display information indicating the second physical index calculated by the first calculating unit 227e.

Figure 18:
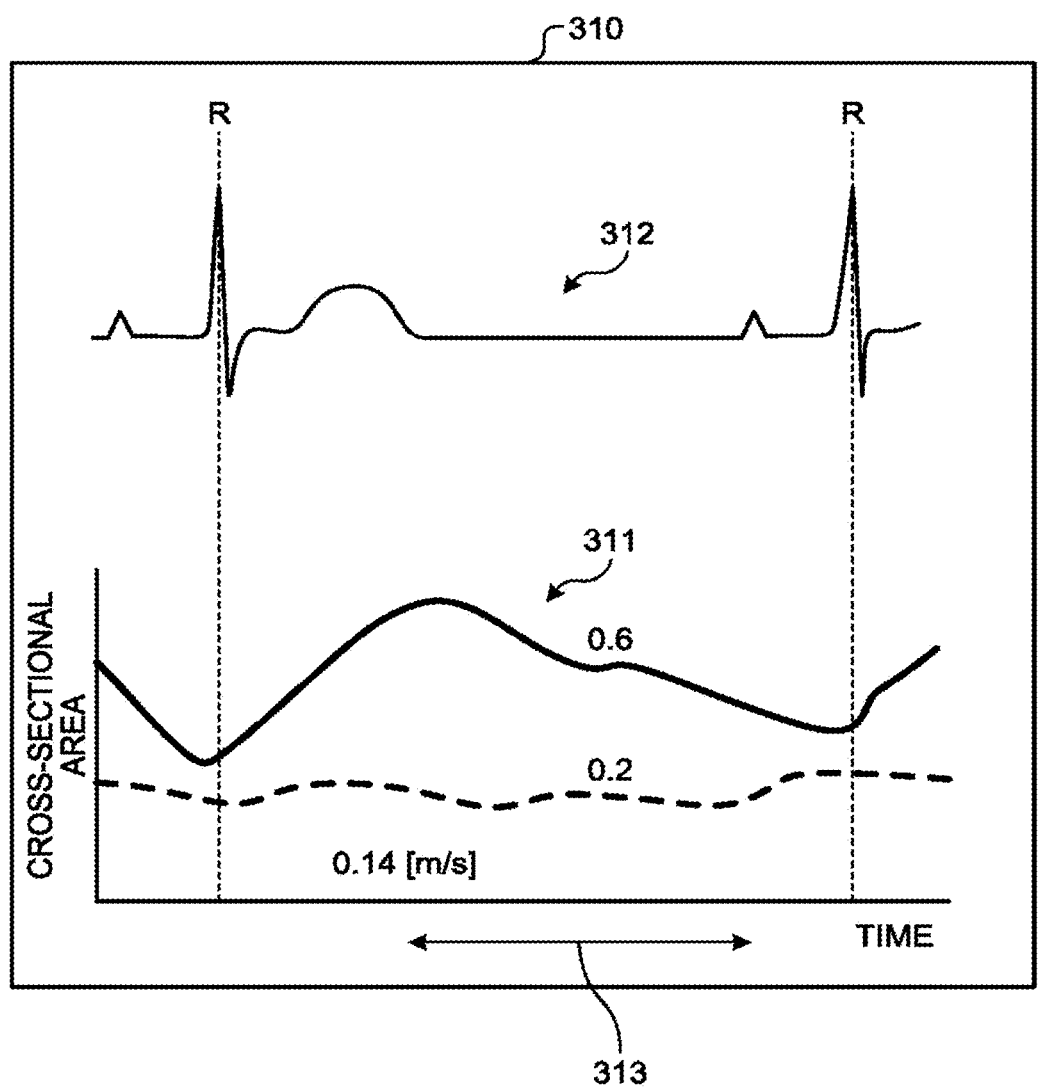
FIG. 18 is a drawing of an example of first display information.

FIG. 18 is a drawing of an example of first display information displayed by the display controlling unit 227g according to the fifth embodiment. For example, the display controlling unit 227g causes the display unit 31 to display first display information 310 illustrated in FIG. 18.

In this situation, the first display information 310 includes information indicating a chronological change in the blood vessel morphology indices. For example, the display controlling unit 227g causes the display unit 31 to display a change curve 311 indicating a chronological change in either the cross-sectional area or the unit volume of the blood vessel of the subject, as the information indicating the chronological change in the blood vessel morphology indices.

For example, as illustrated in the lower section of FIG. 18, the display controlling unit 227g causes the display unit 31 to display a change curve (the curve with a broken line) of the cross-sectional area related to the designated site designated by the operator and a change curve (the curve with a solid line) of the cross-sectional area related to the reference site designated by the operator. In this situation, in place of the change curve of the cross-sectional area of the blood vessel, the display controlling unit 227g may realize a display of a change curve indicating the unit volume of the blood vessel in a similar manner. Further, when causing a plurality of change curves to be displayed, the display controlling unit 227g arranges the change curves to be displayed by using mutually-different types of lines. FIG. 18 illustrates the example in which the change curve related to the designated site is indicated with the broken line, whereas the change curve related to the reference site is indicated with the solid line.

Further, the first display information 310 includes information indicating the blood vessel cross-sectional shape change index, as information indicating the second physical index. For example, as illustrated in the lower section of FIG. 18, the display controlling unit 227g causes the display unit 31 to display a change ratio "0.2" of the cross-sectional area related to the designated area and a change ratio "0.6" of the cross-sectional area related to the reference site. In that situation, the display controlling unit 227g arranges each of the change ratios to be displayed near the corresponding one of the change curves. Further, for example, as indicated by a bidirectional arrow 313 in the lower section of FIG. 18, the display controlling unit 227g may realize a display of information indicating a time span during which the change ratios were measured.

Further, the first display information 310 includes the propagation speed of the blood flowing through the blood vessel of the subject, as the information indicating the second function index. For example, as illustrated in the lower section of FIG. 18, the display controlling unit 227g causes the display unit 31 to display a propagation speed "0.14 [m/s]" of the blood flowing between the designated site and the reference site.

Further, for example, when one or more values of the blood vessel cross-sectional shape change index and the second function index to be displayed exceed a predetermined threshold value, the display controlling unit 227g may realize the display of the blood vessel cross-sectional shape change index and/or the second function index having the value that exceeds the threshold value, by using a display mode that is different from the display modes used for the other values of the blood vessel cross-sectional shape change index and/or the second function index. For example, the display controlling unit 227g realizes the display in such a manner that the blood vessel cross-sectional shape change index and/or the second function index having the value that exceeds the threshold value is displayed in a color different from the color of the other values of the blood vessel cross-sectional shape change index and/or the second function index or in such a manner that the display thereof is turned on and off alternately.

Further, the first display information 310 includes information indicating an electrocardiographic waveform of the subject. The display controlling unit 227g causes the display unit 31 to further display the information indicating the electrocardiographic waveform of the subject, so as to be kept in correspondence with the information indicating the chronological change in the blood vessel morphology indices. For example, as illustrated in the upper section of FIG. 18, the display controlling unit 227g causes the display unit 31 to display information 312 indicating the electrocardiographic waveform in such a manner that the cardiac phases are aligned with the time axis related to the change curves of the cross-sectional areas. In that situation, for example, information indicating electrocardiographic signals of the subject that were actually measured when the CT images in the time series were taken is stored in the storage unit 65 while being kept in correspondence with each of the CT images. Further, for example, when no electrocardiographic signals of the subject were actually measured, the display controlling unit 227g may realize a display of a schematic diagram of an electrocardiographic waveform so as to be kept in correspondence with the information indicating the chronological change in the blood vessel morphology indices, as the information indicating an electrocardiographic waveform.

Although FIG. 18 illustrates the example in which the electrocardiographic waveform is displayed above the change curves of the cross-sectional areas, the positions in which the change curves and the electrocardiographic waveform can be arranged are not limited to those in the example. For instance, the change curves may be displayed above the electrocardiographic waveform.

Further, the example is explained above in which the change curves are displayed to indicate the cross-sectional areas or the unit volumes related to the designated site and the reference site designated by the operator. However, the display of the first display information is not limited to this example. For instance, as the first display information 310, the display unit 31 may display a change curve of either the cross-sectional area or the unit volume at each of a plurality of measuring points that are set in the blood vessel region at regular intervals.

Figure 19:
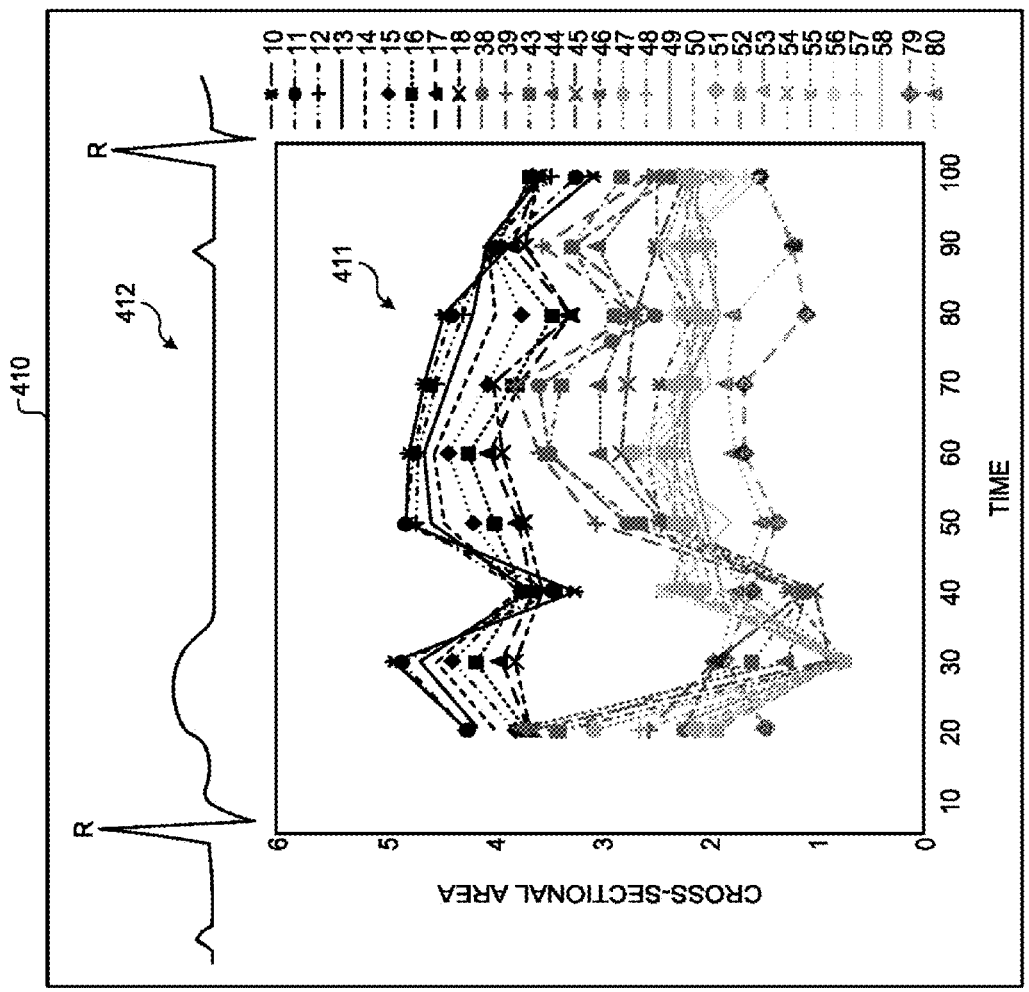
FIG. 19 is a drawing of another example of the first display information.

FIG. 19 is a drawing of another example of the first display information displayed by the display controlling unit 227g according to the fifth embodiment. For example, the display controlling unit 227g causes the display unit 31 to display first display information 410 illustrated in FIG. 19.

In this situation, for example, when a plurality of measuring points "10" to "80" have been set as illustrated in the legend on the right side of FIG. 19, the display controlling unit 227g causes the display unit 31 to display a plurality of change curves 411 related to the measuring points. In that situation also, as illustrated in the upper section of FIG. 19, for example, the display controlling unit 227g causes the display unit 31 to display information 412 indicating an electrocardiographic waveform in such a manner that the cardiac phases thereof are aligned with the time axis related to the change curves of the cross-sectional areas. Further, the display controlling unit 227g realizes the display of the change curves by using the mutually-different types of lines.

FIGS. 18 and 19 illustrate the examples in which the change curves each indicating the chronological change in either the cross-sectional area or the unit volume of the blood vessel are displayed as the information indicating the chronological changes in the blood vessel morphological indices; however, possible embodiments are not limited to these examples. For instance, the display controlling unit 227g may realize a display of a change curve indicating a chronological change in the FFR value. Alternatively, for example, the display controlling unit 227g may realize a display to indicate changes in the FFR value in response to changes of a position (x) that is set on the central line of the coronary artery.

Figure 20:
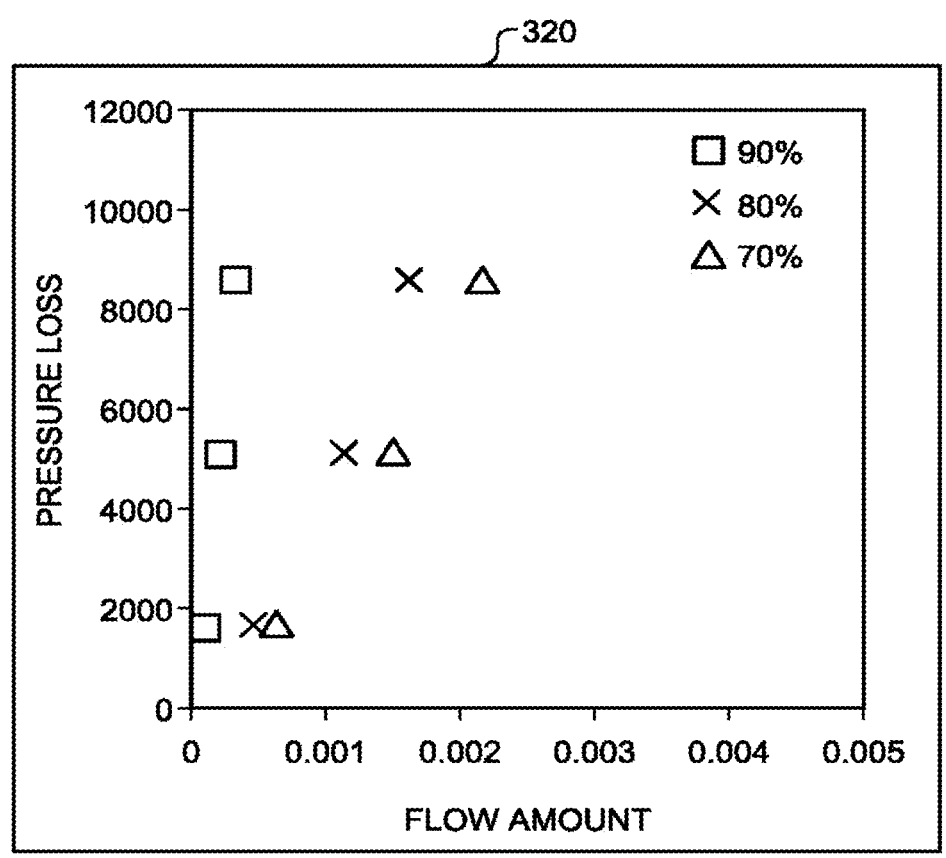
FIG. 20 is a drawing of an example of second display information.

FIG. 20 is a drawing of an example of the second display information displayed by the display controlling unit 227g according to the fifth embodiment. For example, the display controlling unit 227g causes the display unit 31 to display second display information 320 illustrated in FIG. 20.

In this situation, the second display information 320 includes, as information indicating the second function index, information indicating a relationship between a flow amount and at least one selected from between a pressure loss and a pressure loss ratio of the blood vessel of the subject. For example, as illustrated in FIG. 20, the display controlling unit 227g causes the display unit 31 to display a chart in which the vertical axis expresses the pressure loss, whereas the horizontal axis expresses the flow amount. In this situation, for example, the display controlling unit 227g realizes the display of the relationship between the pressure loss and the flow amount in a plurality of cardiac phases for each of the plurality of measuring points.

For instance, in the example illustrated in FIG. 20, the squares (90%), the x's (80%), and the triangles (70%) indicate that the values thereof correspond to mutually-different cardiac phases. Further, the three squares indicate that the values thereof are related to measuring points in mutually-different positions. Similarly, the three x's and the three triangles also indicate that the values thereof are related to measuring points in mutually-different positions. Further, each of the sets made up of one square, one x, and one triangle that are arranged in a horizontal row corresponds to a measuring point in the same position.

Figure 21:
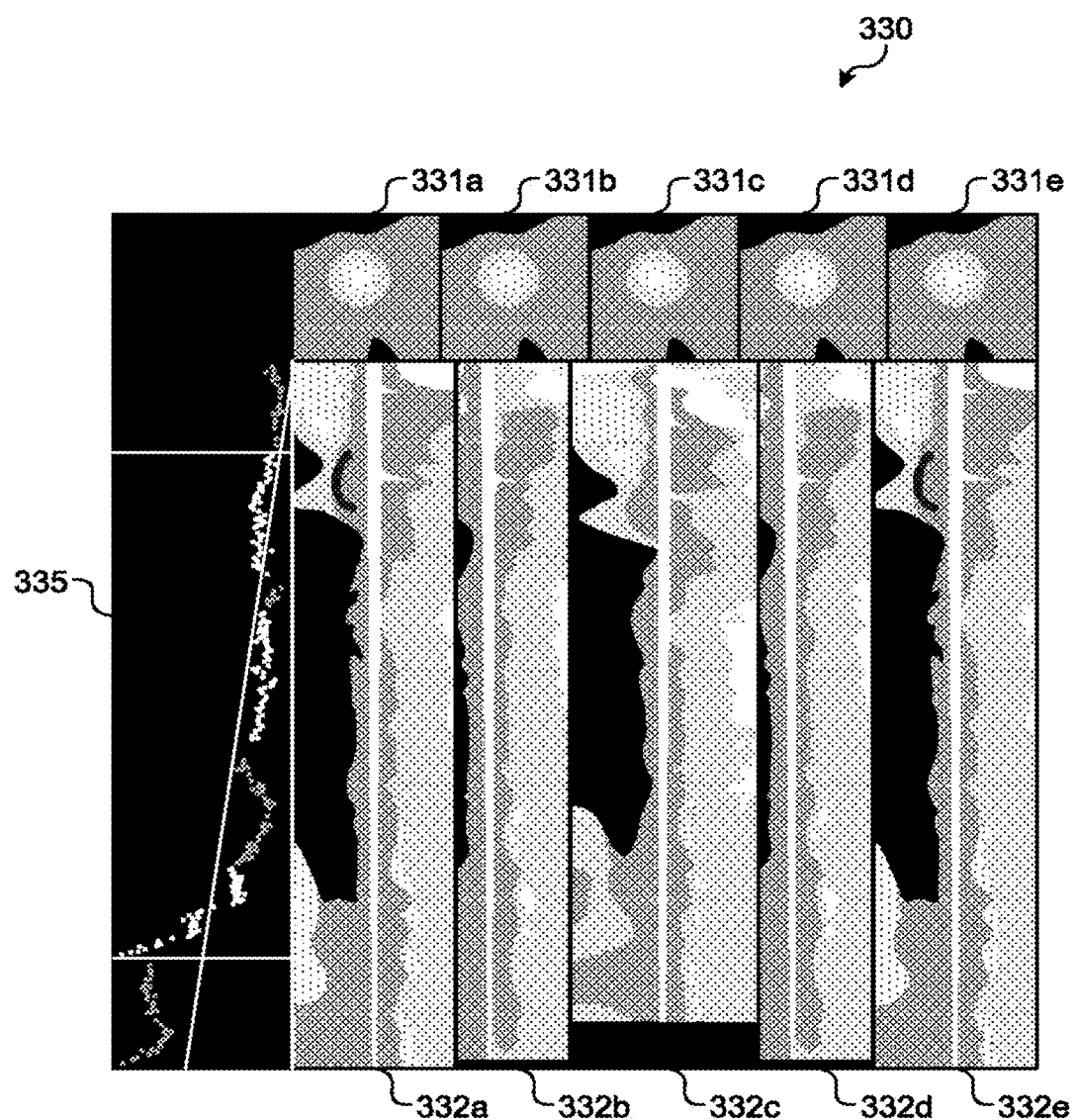
FIG. 21 is a drawing of an example of third display information.

FIG. 21 is a drawing of an example of third display information displayed by the display controlling unit 227g according to the fifth embodiment. For example, the display controlling unit 227g causes the display unit 31 to display third display information 330 illustrated in FIG. 21.

In this situation, the third display information 330 includes cross-sectional images each indicating a cross-sectional plane at a measuring point designated by the operator. For example, the display controlling unit 227g causes the display unit 31 to display, as the cross-sectional images, a cross-sectional image in a first temporal phase indicating a cross-sectional plane at a measuring point designated by the operator and at least one other cross-sectional image in a second temporal phase indicating a cross-sectional plane in such a position that anatomically corresponds to that of the cross-sectional plane in the first temporal phase. For example, as illustrated in the upper section of FIG. 21, the display controlling unit 227g realizes the display of a cross-sectional image 331a indicating the cross-sectional plane at a measuring point designated by the operator and cross-sectional images 331b to 331e in other cardiac phases each indicating a cross-sectional plane in such a position that anatomically corresponds to the cross-sectional plane of the cross-sectional image 331a.

Further, the third display information 330 includes blood vessel long-axis images each including a cross-sectional plane at a measuring point designated by the operator. For example, as the blood vessel long-axis images, the display controlling unit 227g causes the display unit 31 to further display a blood vessel long-axis image in a first temporal phase including the cross-sectional plane at a measuring point designated by the operator and at least one other vessel long-axis image in a second temporal phase including a cross-sectional plane in such a position that anatomically corresponds to that of the cross-sectional plane in the first temporal phase. For example, as illustrated in a section near the center toward the lower right section of FIG. 21, the display controlling unit 227g realizes the display of a blood vessel long-axis image 332a including the cross-sectional plane at a measuring point designated by the operator and blood vessel long-axis images 332b to 332e in other cardiac phases including the cross-sectional plane in such a position that anatomically corresponds to the cross-sectional plane of the blood vessel long-axis image 332a. In this situation, the blood vessel long-axis images may be, for example, Stretched multi-Planar Reconstruction (SPR) images or Curved multi-Planar Reconstruction (CPR) images.

In this situation, for example, the display controlling unit 227g realizes the display of the cross-sectional images 331a to 331e in the plurality of cardiac phases and the plurality of blood vessel long-axis images 332a to 332e while the images are kept in correspondence with one another. For example, as illustrated in FIG. 21, the display controlling unit 227g arranges the plurality of cross-sectional images 331a to 331e and the plurality of blood vessel long-axis images 332a to 332e in such a manner that a cross-sectional image and a blood vessel long-axis image that are in mutually the same cardiac phase are aligned in the up-and-down direction.

FIG. 21 illustrates the example in which the cross-sectional images 331a to 331e are displayed above the blood vessel long-axis images 332a to 332e; however, the positions in which the blood vessel long-axis images 332a to 332e and the cross-sectional images 331a to 331e can be arranged are not limited to those in the example. For instance, the blood vessel long-axis images 332a to 332e may be displayed above the cross-sectional images 331a to 331e.

Further, the third display information 330 includes information indicating a profile of pixel values or cross-sectional areas along the long-axis direction of the blood vessel long-axis images. For example, as illustrated on the left side of FIG. 21, the display controlling unit 227g realizes a display of information 335 indicating a profile of the pixel values along the long-axis direction of the blood vessel long-axis image 332a including the cross-sectional plane at the measuring point designated by the operator. In this situation, the profile of the pixel values along the long-axis direction is a profile of representative values of the pixel values along the long-axis direction in the vascular lumen. For example, the representative values may each be an average value of a plurality of pixels that are in mutually the same position in the long-axis direction in the vascular lumen or the pixel value of a pixel positioned on the central line of the blood vessel. Further, for example, the display controlling unit 227g may realize a display of a profile of pixel values related to the blood vessel long-axis images 332a to 332e in the plurality of cardiac phases so as to be plotted in a single chart area.

In this situation, for example, the display controlling unit 227g realizes the display of the information 335 indicating the profile of the pixel values or the cross-sectional areas and the blood vessel long-axis image on which the profile is based, in such a manner that the positional relationship therebetween in the long-axis direction is kept in correspondence. For example, as illustrated in FIG. 21, the information 335 indicating the profile of the pixel values and the blood vessel long-axis image 332a on which the profile is based are arranged side by side while the sizes and the positions in the long-axis directions are adjusted, so that the positions thereof in the long-axis directions are aligned.

Figure 22:
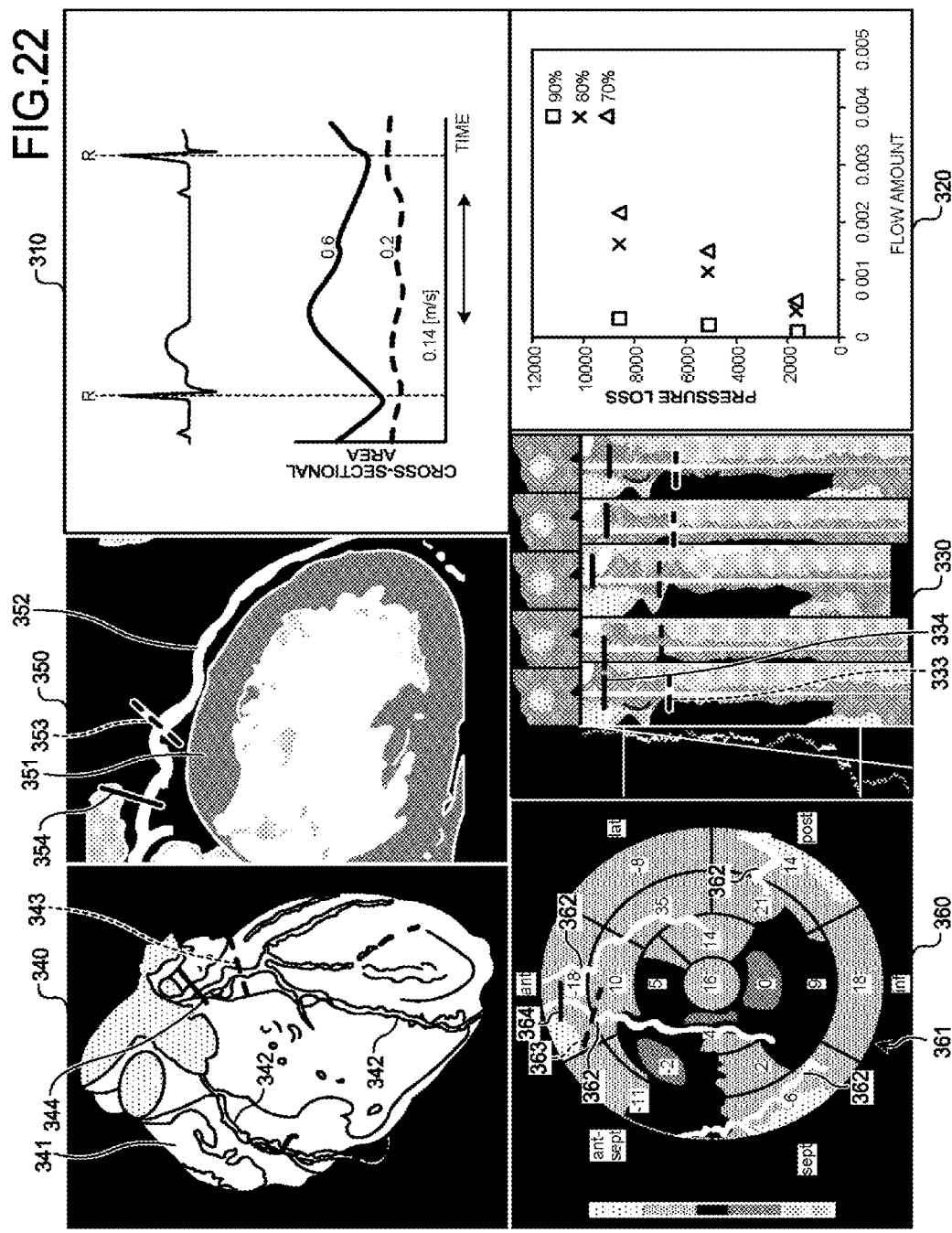
FIG. 22 is a drawing of an example of a result list-view display realized with display information and images.

FIG. 22 is a drawing of an example of a result list-view display realized with display information and images, displayed by the display controlling unit 227g according to the fifth embodiment. For example, as illustrated in FIG. 22, the display controlling unit 227g displays the first display information 310, the second display information 320, the third display information 330, a first reference image 340, a second reference image 350, and a third reference image 360, that are arranged side by side.

In this situation, the first reference image 340, the second reference image 350, and the third reference image 360 each indicate blood vessels of the subject and an organ to which blood is supplied by the blood vessels. In the fifth embodiment, the organ is the heart and the blood vessels are coronary arteries.

For example, the first reference image 340 is a volume rendering image indicating an overall image 341 of the heart of the subject and an overall image 342 of the blood vessels supplying blood to the heart. For example, the display controlling unit 227g generates the volume rendering image by reading a CT image corresponding to the heart serving as a diagnosis target and performing a volume rendering process on the CT image. After that, the display controlling unit 227g realizes the display by using the generated volume rendering image as the first reference image 340.

Further, for example, the second reference image 350 is a Curved multi-Planar Reconstruction (CPR) image indicating an overall image 351 of the heart of the subject and an overall image 352 of the blood vessels supplying blood to the heart. For example, the display controlling unit 227g generates the CPR image by reading a CT image corresponding to the heart and the blood vessels serving as the diagnosis target from the storage unit 65 and performing a cross-section reconstructing process that implements a CPR method on the CT image. After that, the display controlling unit 227g realizes the display by using the generated CPR image as the second reference image 350.

Further, for example, the third reference image 360 is an image obtained by projecting a blood vessel image indicating the blood vessels, onto a bird's-eye-view display of the target site. For example, when the target site is the heart, the third reference image 360 may be an image obtained by projecting a blood vessel image 362 indicating the blood vessels onto a polar map 361 represented by image data resulting from developing three-dimensional data mapping three-dimensional cardiac function information onto a flat plane. In this situation, the polar map may be called a "bull's eye plot" and is represented by the image data resulting from developing the three-dimensional data mapping the three-dimensional cardiac function information onto the flat plane. More specifically, the polar map is represented by image data obtained by projecting information about three-dimensional data on each of a plurality of short-axis cross-sectional planes of the left ventricle that are perpendicular to the long-axis direction extending from the base of the heart where the mitral valve is present to the apex of the heart, onto a "circle of which the center corresponds to the apex of the heart and of which the rim part corresponds to the base of the heart". Even more specifically, the polar map is generated by projecting the three-dimensional data in such a manner that certain positions in the circle indicated by two-dimensional polar coordinates (radii and angles) are kept in correspondence with three-dimensional positions in the myocardia.

For example, the display controlling unit 227g generates the polar map 361 by reading a CT image corresponding to the heart serving as the diagnosis target from the storage unit 65 and performing the abovementioned image processing process on the CT image. Further, the display controlling unit 227g generates the blood vessel image 362 from the CT image and realizes the display by using an image in which the generated blood vessel image 362 is placed over the polar map 361 while the position thereof is being aligned, as the third reference image 360.

Alternatively, for example, when the target site is an intestinal tract or the stomach, the third reference image 360 may be an image obtained by projecting a blood vessel image onto a bird's-eye-view display such as a "fly-thru" development display.

Further, the display controlling unit 227g realizes a display of information indicating the positions of the measuring points designated by the operator, over the reference images. For example, as illustrated in FIG. 22, the display controlling unit 227g arranges graphic elements configured to indicate the positions of the measuring points designated by the operator to be displayed over the first reference image 340, the second reference image 350, and the third reference image 360. FIG. 22 illustrates the example in which graphic elements each rendered as a line segment of a predetermined length are used as the graphic elements.

In this situation, for example, the display controlling unit 227g arranges the graphic elements displayed over the reference images and the change curves in the first display information 310 indicating the cross-sectional areas related to the measuring points corresponding to the graphic elements to be displayed by using lines of mutually the same type. For example, as illustrated in FIG. 22, the display controlling unit 227g arranges the display over the first reference image 340 in such a manner that a graphic element 343 indicating the position of the designated site is displayed by using a broken line like the change curve related to the designated site and that a graphic element 344 indicating the position of the reference site is displayed by using a solid line like the change curve related to the reference site.

Similarly, the display controlling unit 227g arranges the display over the second reference image 350 in such a manner that a graphic element 353 indicating the position of the designated site is displayed by using a broken line and that a graphic element 354 indicating the position of the reference site is displayed by using a solid line. Further, the display controlling unit 227g arranges the display over the third reference image 360 in such a manner that a graphic element 363 indicating the position of the designated site is displayed by using a broken line and that a graphic element 364 indicating the position of the reference site is displayed by using a solid line.

As a result, the operator is able to easily bring the identification regions in the reference images into correspondence with the change curves of the cross-sectional areas included in the first display information 310. Further, the display controlling unit 227g may also similarly arrange a display over the blood vessel long-axis images included in the third display information 330 in such a manner that graphic elements 333 each indicating the position of the designated site and graphic elements 334 each indicating the position of the reference site are displayed by using lines that are of the same type as the respective corresponding change curve.

With reference to FIG. 22, the example is explained in which the graphic elements rendered with the line segments of the predetermined length are used as the graphic elements each indicating the position of the designated site; however, the shapes of the graphic elements are not limited to those in the example. For instance, it is acceptable to use graphic elements having other shapes such as circular shapes or square/rectangular shapes.

With reference to FIG. 22, the example is explained in which the graphic elements each indicating the position of the designated site and the change curve related to the corresponding designated site are displayed by using the lines of mutually the same type. However, the display mode used for keeping the graphic elements and the change curve in correspondence with each other is not limited to this example. For instance, it is acceptable to arrange graphic elements and a change curve corresponding to mutually the same designated site to be displayed in mutually the same color.

Further, the display controlling unit 227g may receive, from the operator, an operation to change the position of any of the graphic elements indicating the measuring points and being displayed over the reference images. In that situation, the display controlling unit 227g instructs the first setting unit 227d to set a new measuring point in accordance with the position changed by the operator. Accordingly, the first calculating unit 227e calculates a second physical index of the blood vessel on the basis of a blood vessel morphology index at the newly-set measuring point. After that, the first identifying unit 227f identifies a second function index of the blood vessel with respect to the newly-set measuring point. The display controlling unit 227g causes the display unit 31 to display information indicating the second physical index and the second function index related to the new measuring point. As a result, the contents displayed in the first display information 310, the second display information 320, and the third display information 330 are updated with the information indicating the second physical index and the second function index that were newly calculated.

As explained above, because the moving of the graphic elements indicating the measuring points is arranged to be in conjunction with the updating of the first display information 310, the second display information 320, and the third display information 330, the operator is able to, while moving the measuring points to desired positions in the reference images, easily check the second function index, the second physical index, and the like of the blood vessel in the desired positions.

The display illustrated in FIG. 22 is merely an example. The display controlling unit 227g does not necessarily have to arrange all of the pieces of information and the images to be displayed. For example, the display controlling unit 227g may arrange a combination of one or more of the following to be displayed: the first display information 310, the second display information 320, the third display information 330, the first reference image 340, the second reference image 350, and the third reference image 360. Further, the layout including the positional arrangements and the sizes of the pieces of information and the images is not limited to the one illustrated in FIG. 22. It is acceptable to change the layout as appropriate.

As explained above, because the reference images indicating the blood vessels of the subject and the organ to which blood is supplied by the blood vessels are displayed, the operator is able to easily understand the part of the organ affected by the blood vessel having a stenosis. In this situation, the images displayed as the reference images are not limited to the first reference image 340, the second reference image 350, and the third reference image 360 illustrated in FIG. 22. It is acceptable to use any other types of images.

Figure 24:
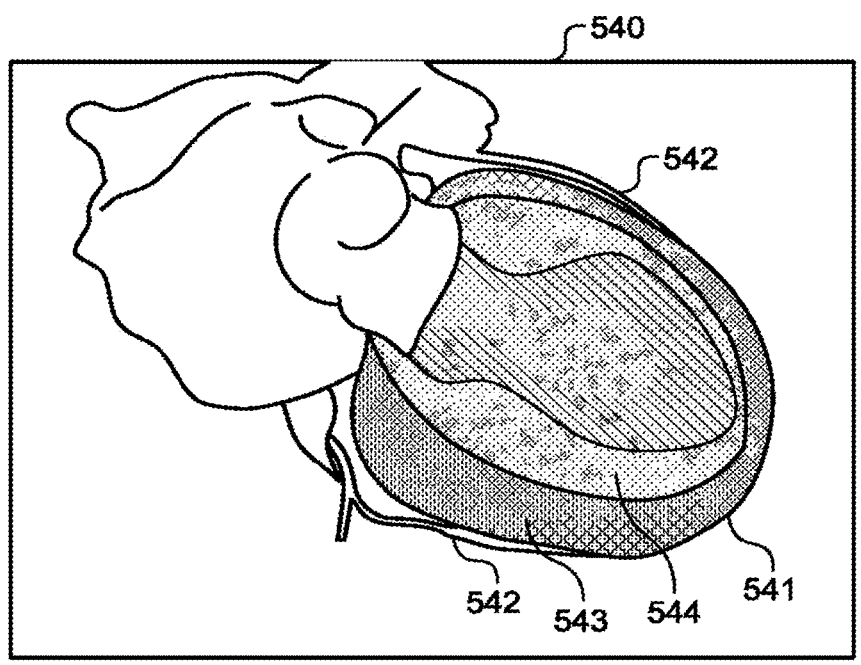
FIG. 24 is a drawing of yet another example of the reference image.
Figure 25:
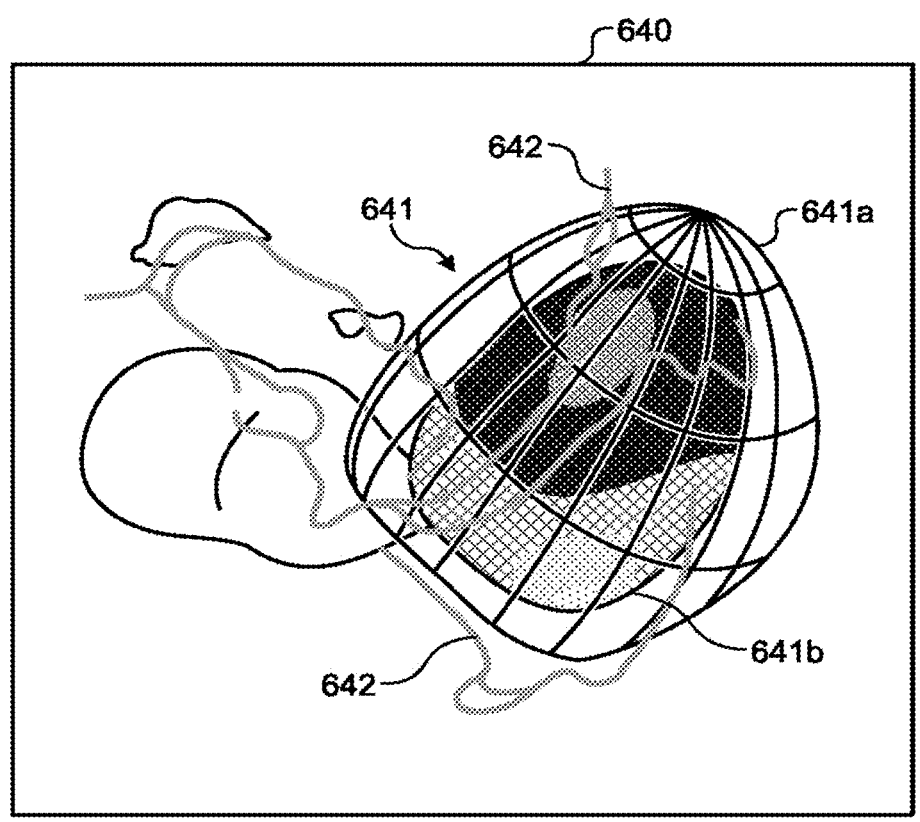
FIG. 25 is a drawing of yet another example of the reference image.

FIGS. 23 to 25 are drawings of other examples of the reference images displayed by the display controlling unit 227g according to the fifth embodiment. For example, as a reference image, the display controlling unit 227g causes the display unit 31 to display an image indicating an organ, blood vessels, and an ischemic state of the organ. For example, as illustrated in FIG. 23, the display controlling unit 227g may display, as a reference image, an image 440 represented by a volume rendering image indicating an overall image 441 of the heart of the subject and an overall image 442 of the blood vessels supplying blood to the heart, in which the display colors of pixels 443 included in the overall image 441 of the heart are varied in accordance with numerical values of perfusion values indicating an ischemic state.

In another example, as illustrated in FIG. 24, the display controlling unit 227g may display, as a reference image, an image 540 represented by a volume rendering image indicating an overall image 541 of the heart of the subject and an overall image 542 of the blood vessels supplying blood to the heart, in which a part of the image of the heart is clipped (cut out). Further, in that situation, for example, the display controlling unit 227g may arrange the image 540 so that the display colors of pixels 543 included in the overall image 541 of the heart and a cross-sectional part 544 exposed due to the clipping are varied in accordance with numerical values of perfusion values indicating an ischemic state. As a result, the operator is able to easily understand the depth of ischemia on the inside of the heart.

In yet another example, as illustrated in FIG. 25, the display controlling unit 227g may display, as a reference image, an image 640 represented by a volume rendering image indicating an overall image 641 of the heart of the subject and an overall image 642 of the blood vessels supplying blood to the heart, in which an external wall part 641a of the myocardia is displayed in a wire form, while the display colors of pixels in an internal wall part 641b of the myocardia are varied in accordance with numerical values of perfusion values.

As explained above, because the image indicating the ischemic state of the organ is displayed as the reference image, the operator is able to easily understand such a part of the organ serving as the diagnosis target that is experiencing hemodynamic failure due to the blood vessel having a stenosis.

Further, for example, the display controlling unit 227g may cause the display unit 31 to display, as a reference image, an image taken by a medical image diagnosis apparatus that is different from the medical image diagnosis apparatus that took the images in the time series stored in the storage unit 65. In the fifth embodiment, the example is explained in which the CT images in the time series that include the images of the entire organ and the entire blood vessels were taken by the X-ray CT apparatus. However, for example, if the storage unit 65 does not have any medical images taken of the entire organ or the entire blood vessels serving as diagnosis targets stored therein, it is acceptable to display, as a reference image, an image taken by a medical image diagnosis apparatus other than the X-ray CT apparatus or a processed image generated from such an image. In that situation, it is assumed that the storage unit 65 has also stored therein the image taken by the medical image diagnosis apparatus other than the X-ray CT apparatus. In this situation, the medical image diagnosis apparatus other than the X-ray CT apparatus may be, for example, a Magnetic Resonance Imaging (MRI) apparatus, an ultrasound diagnosis apparatus, an X-ray diagnosis apparatus, or a nuclear medicine diagnosis apparatus. In other words, for example, it is acceptable to obtain a reference image by combining an overall blood vessel image obtained from a CT apparatus or an MRI apparatus, with an overall organ image obtained from a nuclear medicine diagnosis apparatus. It is also acceptable to combine an overall organ image obtained from an ultrasound image with an overall blood vessel image obtained from a CT image. Further, it is also acceptable to superimpose, onto a local blood vessel image taken by an ultrasound apparatus, an overall blood vessel image that is obtained from a CT image or an MR image and that includes the local site, and to further superimpose thereon an overall organ image obtained from a CT image or an MR image.

As explained above, by displaying the image taken by any of the various types of medical image diagnosis apparatuses as a reference image, it is possible to display a reference image that is more suitable for each diagnosis process.

The third calculating unit 227c may display the information indicating the function index only for the CT images in some or one of the cardiac phases covered by the CT images in the time series, for example, instead of displaying the information indicating the function index for each of the CT images in the time series. For example, the third calculating unit 227c may display the information indicating the function index for the cardiac phase in which the FFR is minimized. Alternatively, the third calculating unit 227c may display the information indicating the function index for the cardiac phases in which the change in the FFR is smaller than a predetermined threshold.

Furthermore, for example, the third calculating unit 227c may further display the stenosis ratio or the FFR difference, next to the FFR value. For example, the third calculating unit 227c displays the FFR value for each of a plurality of different positions of a blood vessel, and displays the stenosis ratio, next to the FFR value. As another example, the third calculating unit 227c may display the FFR value for each of a plurality of different blood vessels, and display the stenosis ratio next to the FFR value. At this time, the third calculating unit 227c may display the stenosis ratio only for a position or a blood vessel having an FFR value smaller than a predetermined threshold, for example. The third calculating unit 227c may also display the stenosis ratio only for a position or a blood vessel having a specific FFR value, for example. The third calculating unit 227c may also display the FFR difference, instead of the stenosis ratio. By displaying the stenosis ratio or the FFR difference next to the FFR value, the operator can determine whether a treatment is required, accurately.

Figure 26:
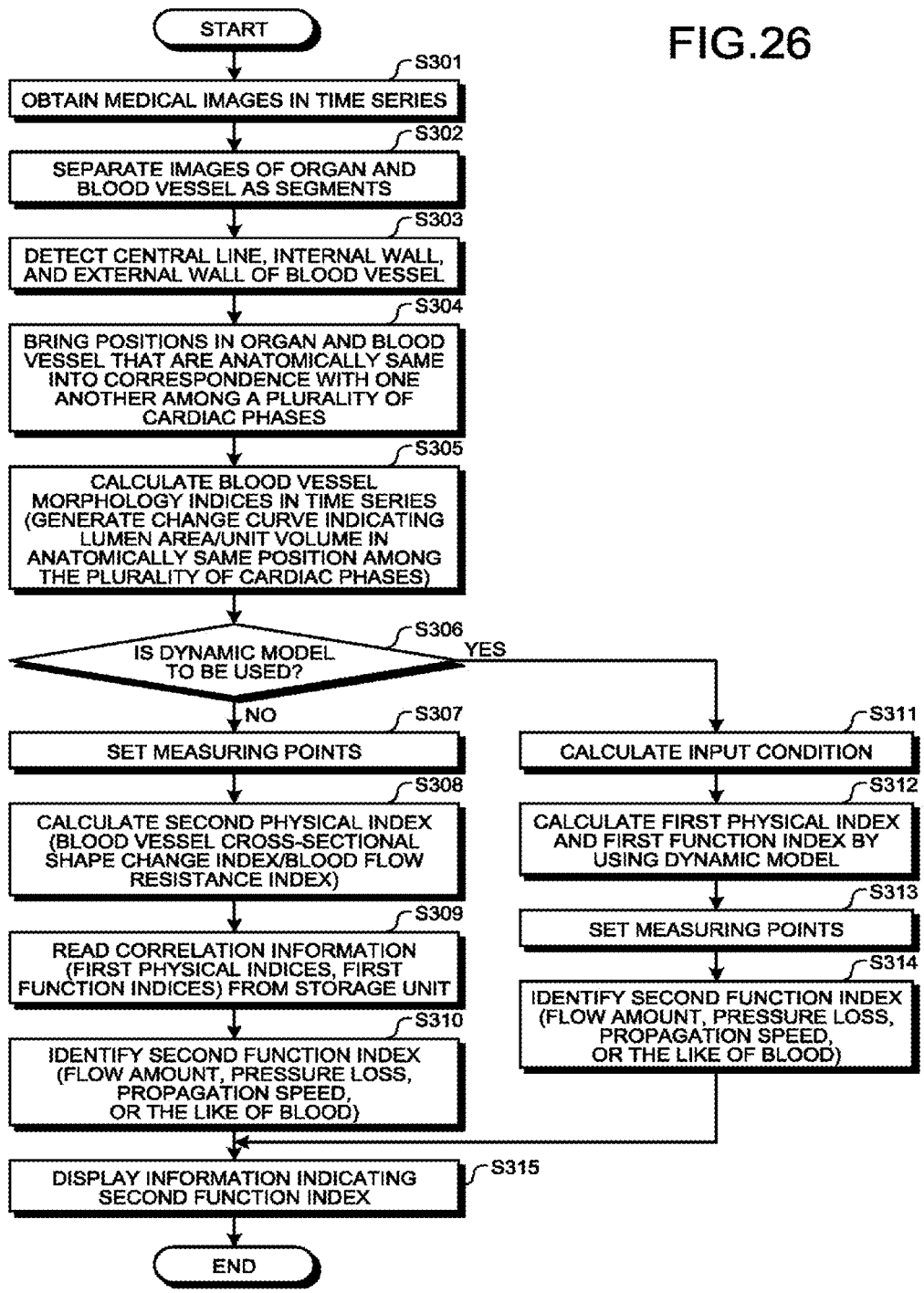
FIG. 26 is a flowchart of a flow in a blood vessel analyzing process.

Next, a flow in a blood vessel analyzing process performed by the image processing apparatus 227 according to the fifth embodiment will be explained. FIG. 26 is a flowchart of the flow in the blood vessel analyzing process performed by the image processing apparatus 227.

As illustrated in FIG. 26, in the image processing apparatus 227 according to the fifth embodiment, the obtaining unit 69 first obtains medical images in a time series indicating a blood vessel of a subject and a site to which blood is supplied by the blood vessel (step S301).

Subsequently, the third calculating unit 227c separates an organ region and a blood vessel region as segments, from the medical images in the time series (step S302). Further, the third calculating unit 227c detects the central line, the internal wall, and the external wall of the blood vessel from the segmented blood vessel region (step S303). Further, the third calculating unit 227c brings positions in the organs and the blood vessel that are anatomically the same as one another among a plurality of cardiac phases into correspondence with one another (step S304).

After that, the third calculating unit 227c calculates blood vessel morphology indices in a time series indicating morphology of the blood vessel of the subject on the basis of the medical images in the time series (step S305). In that situation, for example, the third calculating unit 227c generates a change curve indicating either a lumen area or a unit volume in the anatomically same position among the plurality of cardiac phases.

Further, if a dynamic model is not to be used (step S306: No), the first setting unit 227d sets measuring points each indicating a site at which the second function index is to be measured, in the blood vessel region included in the medical images (step S307).

The judgment of whether a dynamic model is to be used or not may be made according to an instruction issued by the operator via the input unit 29 or may be made on the basis of setting information stored in the storage unit 65 or the like in advance. The judgment is made by, for example, a controlling unit included in the image processing apparatus 227, so that the constituent elements of the image processing apparatus 227 are controlled in accordance with the judgment result.

Subsequently, the first calculating unit 227e calculates a second physical index at the set measuring points, on the basis of the blood vessel morphology indices in the time series (step S308). In this situation, for example, the first calculating unit 227e calculates either a blood vessel cross-sectional shape change index or a blood flow resistance index.

After that, the first identifying unit 227f reads the correlation information (the first physical indices and the first function indices) from the storage unit 65 (step S309). Further, the first identifying unit 227f identifies a second function index (a flow amount, a pressure loss, a propagation speed, or the like of the blood) of the blood vessel of the subject related to vascular hemodynamics, on the basis of the correlation information and the second physical index of the blood vessel (step S310).

On the contrary, if a dynamic model is to be used (step S306: Yes), the first identifying unit 227f calculates an input condition of the dynamic model, on the basis of the blood vessel morphology indices calculated from the medical images in the time series (step S311). Further, the first identifying unit 227f calculates a first physical index and a first function index by using the dynamic model (step S312).

After that, after measuring points are set by the first setting unit 227d (step S313), the first identifying unit 227f identifies a second function index (a flow amount, a pressure loss, a propagation speed, or the like of the blood) of the blood vessel of the subject related to vascular hemodynamics, on the basis of a result of a fluid structure analysis (step S314).

After that, when the second function index has been identified in this manner, the display controlling unit 227g causes the display unit 31 to display information indicating the second function index (step S315).

As explained above, according to the fifth embodiment, the second function index of the blood vessel of the subject related to the vascular hemodynamics is identified and displayed, from the medical images in the time series indicating the blood vessels of the subject and the organ to which blood is supplied by the blood vessels. Consequently, according to the fifth embodiment, it is possible to aid a diagnosis process to evaluate hematogenous ischemia in the blood vessels.

In the exemplary embodiments described above, the example is explained in which the obtaining unit obtains the CT images in the time series as the medical images; however, possible embodiments are not limited to this example. For instance, to perform an image taking process using an X-ray CT apparatus, a prep scan for determining timing to start a main scan may be performed prior to the main scan, which is performed for taking diagnosis-purpose images. According to this image taking method, a change curve indicating a chronological change in CT values that fluctuate in accordance with the concentration level of the contrast agent is calculated from data that is continuously acquired by performing the prep scan, and further, the timing to start the main scan is determined on the basis of the change curve. When this type of image taking process is performed, the obtaining unit may further obtain, for example, the data acquired in the prep scan.

For example, the flow amount and the flow rate of blood are considered to vary depending on the physique and the gender of the subject and the state of the subject. For this reason, for example, when calculating the blood vessel morphology indices, the third calculating unit described in the embodiments above may adjust the blood vessel morphology indices for each subject, on the basis of the data acquired in the prep scan. With this arrangement, it is possible to further improve the precision level of the function index of the blood vessel obtained by performing the blood vessel analyzing process described in the embodiments above.

Other Embodiments

The constituent elements of the apparatuses and the devices referred to in the drawing in the explanation of the embodiments above are based on functional concepts. Thus, it is not necessary to physically configure the elements as indicated in the drawing. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a program that is analyzed and executed by the CPU or may be realized as hardware using wired logic.

Figure 27:
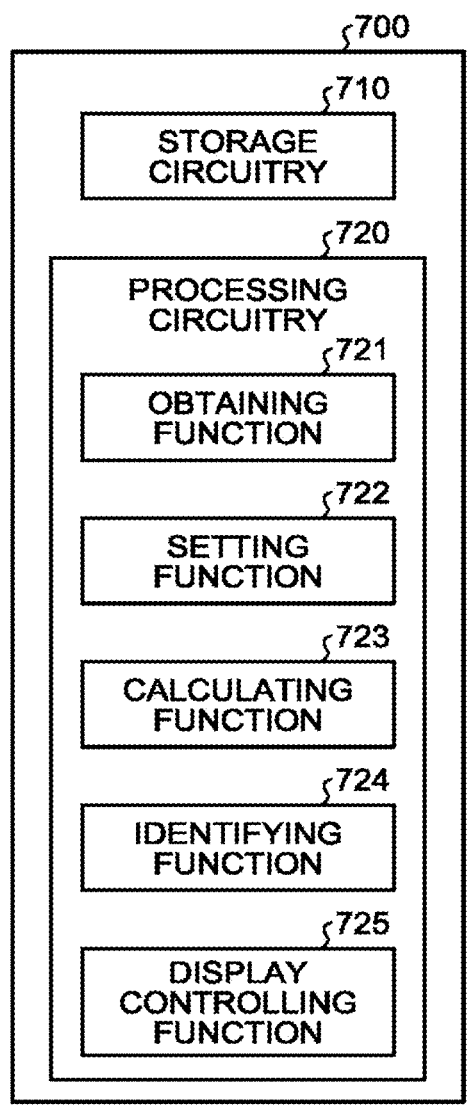
FIG. 27 is a functional block diagram of an image processing apparatus according to another embodiment.

For example, it is acceptable to configure the image processing apparatus explained in any of the embodiments described above as illustrated in FIG. 27. FIG. 27 is a functional block diagram of an image processing apparatus according to another embodiment. As illustrated in FIG. 27, an image processing apparatus 700 includes a storage circuitry 710 and a processing circuitry 720.

The storage circuitry 710 corresponds to the storage unit 65 explained in any of the first, the fourth, and the fifth embodiments, the storage unit 65A explained in the second embodiment, or the storage unit 33 explained in the third embodiment.

Further, the processing circuitry 720 includes an obtaining function 721, a setting function 722, a calculating function 723, an identifying function 724, and a display controlling function 725. The obtaining function 721 is an example of the obtaining unit set forth in the claims. The setting function 722 is an example of the setting unit set forth in the claims. The calculating function 723 is an example of the calculating unit set forth in the claims. The identifying function 724 is an example of the identifying unit set forth in the claims. The display controlling function 725 is an example of the display controlling unit set forth in the claims.

The obtaining function 721 corresponds to the function realized by the obtaining unit 69 explained in any of the first, the second, the fourth, and the fifth embodiments or the first obtaining unit 151 and the second obtaining unit 152 explained in the third embodiment.

The setting function 722 corresponds to the function realized by the first setting unit 51 explained in any of the first, the second, and the fourth embodiments, the setting unit 154 explained in the third embodiment, or the first setting unit 227d explained in the fifth embodiment.

The calculating function 723 corresponds to the function realized by the first calculating unit 67 explained in any of the first, the second, and the fourth embodiments, the calculating unit 153 explained in the third embodiment, or the first calculating unit 227e and the third calculating unit 227c explained in the fifth embodiment.

The identifying function 724 corresponds to the function realized by the first identifying unit 66 explained in either of the first and the fourth embodiments, the first identifying unit 66A explained in the second embodiment, the first identifying unit 156 or 156a explained in the third embodiment, or the first identifying unit 227f explained in the fifth embodiment.

The display controlling function 725 corresponds to the function realized by the display controlling unit 68 explained in the second embodiment, the display controlling unit 157 explained in the third embodiment, or the display controlling unit 227g explained in the fifth embodiment.

For example, processing functions executed by the obtaining function 721, the setting function 722, the calculating function 723, the identifying function 724, and the display controlling function 725, which are constituent elements of the processing circuitry 720 illustrated in FIG. 27, are recorded in the storage circuitry 710 in the form of computer-executable programs. The processing circuitry 720 is a processor configured to realize the functions corresponds to the programs, by reading the programs from the storage circuitry 710 and executing the read programs. In other words, when having read the programs, the processing circuitry 720 has the functions illustrated on the inside of the processing circuitry 720 in FIG. 27.

That is to say, the processing circuitry 720 performs the same processes as those performed by the obtaining unit 69, the first obtaining unit 151 or the second obtaining unit 152, by reading and executing a program corresponding to the obtaining function 721 from the storage circuitry 710. Further, the processing circuitry 720 performs the same processes as those performed by the first setting unit 51, the setting unit 154 or the first setting unit 227d by reading and executing a program corresponding to the setting function 722 from the storage circuitry 710. In addition, the processing circuitry 720 performs the same processes as those performed by the first calculating unit 67, the calculating unit 153, the first calculating unit 227e or the third calculating unit 227c by reading and executing a program corresponding to the calculating function 723 from the storage circuitry 710. Further, the processing circuitry 720 performs the same processes as those performed by the first identifying unit 66, 66A, 156, 156a or 227f by reading and executing a program corresponding to the identifying function 724 from the storage circuitry 710. Furthermore, the processing circuitry 720 performs the same processes as those performed by the display controlling unit 68, 157 or 227g by reading and executing a program corresponding to the display controlling function 725 from the storage circuitry 710.

For example, step S100 illustrated in FIG. 6 is a step realized as a result of the processing circuitry 720 reading and executing a program corresponding to the obtaining unit 69 from the storage circuitry 710. Further, step S101 illustrated in FIG. 6 is a step realized as a result of the processing circuitry 720 reading and executing a program corresponding to the first setting unit 51 from the storage circuitry 710. In addition, step S102 illustrated in FIG. 6 is a step realized as a result of the processing circuitry 720 reading and executing a program corresponding to the first calculating unit 67 from the storage circuitry 710. Furthermore, step S103 illustrated in FIG. 6 is a step realized as a result of the processing circuitry 720 reading and executing a program corresponding to the first identifying unit 66 from the storage circuitry 710.

As other examples, step S1 illustrated in FIG. 9 is a step realized as a result of the processing circuitry 720 reading and executing a program corresponding to the obtaining unit 69 from the storage circuitry 710. Further, step S2 illustrated in FIG. 9 is a step realized as a result of the processing circuitry 720 reading and executing a program corresponding to the first setting unit 51 from the storage circuitry 710. In addition, step S3 illustrated in FIG. 9 is a step realized as a result of the processing circuitry 720 reading and executing a program corresponding to the first identifying unit 66A from the storage circuitry 710. Further, step S4 illustrated in FIG. 9 is a step realized as a result of the processing circuitry 720 reading and executing a program corresponding to the first calculating unit 67 from the storage circuitry 710. In addition, steps S5 through S16 illustrated in FIG. 9 are steps realized as a result of the processing circuitry 720 reading and executing a program corresponding to the first identifying unit 66A from the storage circuitry 710. Furthermore, steps S17 through S20 illustrated in FIG. 9 are steps realized as a result of the processing circuitry 720 reading and executing a program corresponding to the display controlling unit 68 from the storage circuitry 710.

As other examples, step S201 illustrated in FIG. 16 is a step realized as a result of the processing circuitry 720 reading and executing a program corresponding to the obtaining unit 69 from the storage circuitry 710. Further, for example, steps S202 and S203 illustrated in FIG. 16 are steps realized as a result of the processing circuitry 720 reading and executing a program corresponding to the first setting unit 51 from the storage circuitry 710. In addition, for example, steps S204 and S205 illustrated in FIG. 16 are steps realized as a result of the processing circuitry 720 reading and executing a program corresponding to the first calculating unit 67 from the storage circuitry 710. Furthermore, for example, step S206 illustrated in FIG. 16 is a step realized as a result of the processing circuitry 720 reading and executing a program corresponding to the first identifying unit 66 from the storage circuitry 710.

As other examples, step S301 illustrated in FIG. 26 is a step realized as a result of the processing circuitry 720 reading and executing a program corresponding to the obtaining unit 69 from the storage circuitry 710. Further, for example, steps S302 through S306 illustrated in FIG. 26 are steps realized as a result of the processing circuitry 720 reading and executing a program corresponding to the third calculating unit 227c from the storage circuitry 710. In addition, for example, step S307 illustrated in FIG. 26 is a step realized as a result of the processing circuitry 720 reading and executing a program corresponding to the first setting unit 227d from the storage circuitry 710. Furthermore, for example, step S308 illustrated in FIG. 26 is a step realized as a result of the processing circuitry 720 reading and executing a program corresponding to the first calculating unit 227e from the storage circuitry 710. In addition, for example, steps S309 through S314 illustrated in FIG. 26 are steps realized as a result of the processing circuitry 720 reading and executing a program corresponding to the first identifying unit 227f from the storage circuitry 710. Furthermore, for example, step S315 illustrated in FIG. 26 is a step realized as a result of the processing circuitry 720 reading and executing a program corresponding to the display controlling unit 227g from the storage circuitry 710.

FIG. 27 illustrates the example in which each of the processing functions of the obtaining function 721, the setting function 722, the calculating function 723, the identifying function 724, and the display controlling function 725 is realized by using a single processing circuitry. However, it is also acceptable to structure a processing circuitry by combining a plurality of independent processors together, so that the functions are realized as a result of each of the processors executing a corresponding one of the programs.

The term "processors" mentioned above denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device (SPLD), a Complex Programmable Logic Device (CPLD), or Field Programmable Gate Array (FPGA)). The processor realizes the function by reading and executing the program stored in the storage circuitry. Alternatively, it is also acceptable to incorporate the program directly into the circuit of the processor, instead of storing the program in the storage circuitry. In that situation, the processor realizes the function by reading and executing the program incorporated in the circuit thereof. The processors used in the present embodiment do not necessarily have to be each structured as a single circuit. It is also acceptable to combine a plurality of independent circuits together to structure one processor so as to realize the functions thereof. Further, it is also acceptable to integrate the plurality of constituent elements illustrated in FIG. 7 into one processor, so as to realize the functions thereof.

According to at least one aspect of the embodiments described above, it is possible to identify the function index of the blood vessel in the non-invasive manner and at a high speed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus, comprising:
    processing circuitry configured to
        obtain images in a time series including images of a blood vessel of a subject and correlation information indicating a correlational relationship between physical indices of the blood vessel and parameters for a fluid analysis of the blood vessel,
        calculate blood vessel morphology indices in a time series indicating morphology of the blood vessel of the subject, based on the images in the time series,
        calculate a physical index of the blood vessel of the subject, based on the blood vessel morphology indices in the time series, the physical index indicating a temporal change ratio of the blood vessel morphology indices,
        identify a parameter for the fluid analysis of the blood vessel by using the calculated physical index of the blood vessel of the subject, based on the correlation information, and
        identify a pressure ratio in the blood vessel by performing the fluid analysis using the identified parameter and at least one of the calculated blood vessel morphology indices; and
    a display that displays the identified pressure ratio in the blood vessel.

2. The image processing apparatus according to claim 1, wherein
    the processing circuitry is further configured to set an identification target region for the pressure ratio in the blood vessel, in a blood vessel region included in the images, and
    the processing circuitry is further configured to
    calculate the physical index of the identification target region from the blood vessel morphology indices, and
    identify the parameter for the fluid analysis, based on the correlation information and the calculated physical index.

3. The image processing apparatus according to claim 2, wherein
    the processing circuitry is further configured to identify a parameter from the correlation information that corresponds to the physical index equal to the calculated physical index, as the parameter for the fluid analysis.

4. The image processing apparatus according to claim 2, wherein the processing circuitry is further configured to
    set an ex-ante distribution of the parameter for the fluid analysis, which is related to at least one of a shape in a stress-free state and a physical property value of the identification target region,
    calculate a prediction value of at least one of a blood flow amount index and a blood vessel morphology index of the identification target region, based on the ex-ante distribution,
    calculate, based on the images, an observed value of at least one of the blood flow amount index and the blood vessel morphology index,
    identify an ex-post distribution of the parameter for the fluid analysis, based on the prediction value, the observed value, and a parameter from the correlation information that corresponds to the physical index equal to the calculated physical index, so that the prediction value matches the observed value, and identify the pressure ratio in the blood vessel, based on an identified value in the ex-post distribution.

5. The image processing apparatus according to claim 4, wherein the processing circuitry is further configured to
identify the ex-post distribution by setting a data distribution related to an error between the prediction value and the observed value, and further performing a statistical identifying process on a probability distribution indicated by the pressure ratio of the blood vessel and on the data distribution, with respect to the ex-ante distribution, and
keep resetting the ex-ante distribution and performing the statistical identifying process, until the ex-post distribution satisfies an identification ending condition.

6. The image processing apparatus according to claim 4, wherein the processing circuitry is further configured to
obtain first information in which the parameter for the fluid analysis is kept in correspondence with at least one of the blood flow amount index and the blood vessel morphology index, and
calculate, as the prediction value, at least one of the blood flow amount index and the blood vessel morphology index that is from the first information, and that corresponds to the parameter for the fluid analysis indicated by the ex-ante distribution.

7. The image processing apparatus according to claim 4, wherein the processing circuitry is further configured to
calculate blood vessel morphology indices in a time series and blood vessel cross-sectional shape change indices in a time series with respect to an analysis target region in the blood vessel region, based on the images,
construct a dynamic model related to the analysis target region, based on the images, the blood vessel morphology indices in the time series, and the blood vessel cross-sectional shape change indices in the time series, and
calculate the prediction value by analyzing the dynamic model.

8. The image processing apparatus according to claim 4, wherein the processing circuitry is further configured to identify the pressure ratio of the blood vessel by constructing a dynamic model to which the identified value in the ex-post distribution is assigned, and performing either a blood vessel stress analysis or a blood fluid analysis on the dynamic model.

9. The image processing apparatus according to claim 1, wherein the physical indices are at least one of a blood vessel cross-sectional shape change index indicating a change index of a cross-sectional shape of the blood vessel and a blood flow resistance index indicating an index of a blood flow resistance.

10. The image processing apparatus according to claim 1, wherein the processing circuitry is further configured to cause the display to display a combined image obtained by combining a first image indicating the correlation information with a second image indicating the identified pressure ratio.

11. The image processing apparatus according to claim 1, wherein the processing circuitry is further configured to identify the pressure ratio in the blood vessel by further using a concentration change amount of the images.

12. The image processing apparatus according to claim 1, wherein the processing circuitry is further configured to
set, in a blood vessel region included in the images, a first cross-sectional plane of a blood vessel having a stenosis on a downstream side of the stenosis and a second cross-sectional plane of a blood vessel having no stenosis,
calculate the blood vessel morphology indices in the time series with respect to each of the first cross-sectional plane and the second cross-sectional plane, and further calculate a blood vessel cross-sectional shape change index for each of the first cross-sectional plane and the second cross-sectional plane based on the blood vessel morphology indices, and
identify the pressure ratio in the blood vessel, by using the blood vessel cross-sectional shape change index for each of the first cross-sectional plane and the second cross-sectional plane, as the physical index.

13. The image processing apparatus according to claim 12, wherein the correlation information is a one-dimensional mathematical model related to dynamics.

14. The image processing apparatus according to claim 12, wherein the processing circuitry is further configured to set the first cross-sectional plane in a vicinity of a distal part of a coronary artery having the stenosis, and set the second cross-sectional plane in a vicinity of a starting part of a coronary artery having no stenosis.

15. The image processing apparatus according to claim 12, wherein the blood vessel morphology index is a radius and a wall thickness of each of the first cross-sectional plane and the second cross-sectional plane of the blood vessels, whereas the blood vessel cross-sectional shape change index is a change amount in the radius of each of the first cross-sectional plane and the second cross-sectional plane of the blood vessels.

16. The image processing apparatus according to claim 1, wherein the processing circuitry is further configured to
calculate either a cross-sectional area or a unit volume of the blood vessel of the subject, as the blood vessel morphology indices, and
cause the display to further display a change curve indicating a chronological change in either the cross-sectional area or the unit volume.

17. The image processing apparatus according to claim 16, wherein the processing circuitry is further configured to cause the display to further display information indicating an electrocardiographic waveform of the subject during an image taking process, together with the information indicating the chronological change in the blood vessel morphology indices.

18. The image processing apparatus according to claim 17, wherein the processing circuitry is further configured to cause the display to display the information indicating the electrocardiographic waveform so as to be kept in correspondence with the information indicating the chronological change in the blood vessel morphology indices.

19. The image processing apparatus according to claim 16, wherein the processing circuitry is further configured to
identify a propagation speed of blood flowing through the blood vessel of the subject, and
cause the display to display the propagation speed.

20. The image processing apparatus according to claim 16, wherein the processing circuitry is further configured to cause the display to further display cross-sectional images corresponding to a plurality of temporal phases indicating a cross-sectional plane at a measuring point designated by an operator of the image processing apparatus.

21. The image processing apparatus according to claim 16, wherein the processing circuitry is further configured to cause the display to further display a medical image of the subject, together with the information indicating the pressure ratio.

22. The image processing apparatus according to claim 1, wherein the processing circuitry is further configured to calculate the physical index for some or one of cardiac phases corresponding to CT images in the time series, based on the blood vessel morphology indices corresponding to the some or one of the cardiac phases.

23. The image processing apparatus according to claim 22, wherein the processing circuitry is further configured to specify, for each of a plurality of blood vessels, a temporal phase used in calculating the physical index, and to calculate the physical index for the specified temporal phase.

24. The image processing apparatus according to claim 1, wherein the processing circuitry is further configured to display information indicating the pressure ratio for images in some or one of temporal phases covered by the image in the time series on a display.

25. The image processing apparatus according to claim 24, wherein the processing circuitry is further configured to display a fractional flow reserve (FFR) value, as the information indicating the pressure ratio, and to further display a stenosis ratio or an FFR difference next to the FFR value.

26. The image processing apparatus according to claim 25, wherein the processing circuitry is further configured to display the FFR value for each of a plurality of different positions of a blood vessel or for each of a plurality of different blood vessels, and to further display the stenosis ratio or the FFR difference for a position or a blood vessel having an FFR value smaller than a predetermined threshold, or having a specific FFR value.

27. An image processing method, comprising:
obtaining images in a time series including images of a blood vessel of a subject and correlation information indicating a correlational relationship between physical indices of the blood vessel and parameters for a fluid analysis of the blood vessel;
calculating blood vessel morphology indices in a time series indicating morphology of the blood vessel of the subject, based on the images in the time series;
calculating a physical index of the blood vessel of the subject, based on the blood vessel morphology indices in the time series, the physical index indicating a temporal change ratio of the blood vessel morphology indices,
identifying a parameter for a fluid analysis of the blood vessel, by using the calculated physical index of the blood vessel of the subject, based on the correlation information;
identifying a pressure ratio in the blood vessel by performing the fluid analysis using the identified parameter and at least one of the calculated blood vessel morphology indices; and
displaying the identified pressure ratio in the blood vessel.

28. A non-transitory computer-readable storage medium having recorded thereon a plurality of computer-executable instructions that cause the computer to execute the steps of:
obtaining images in a time series including images of a blood vessel of a subject and correlation information indicating a correlational relationship between physical indices of the blood vessel and parameters for a fluid analysis of the blood vessel;
calculating blood vessel morphology indices in a time series indicating morphology of the blood vessel of the subject, based on the images in the time series;
calculating a physical index of the blood vessel of the subject, based on the blood vessel morphology indices in the time series, the physical index indicating a temporal change ratio of the blood vessel morphology indices;
identifying a parameter for a fluid analysis of the blood vessel, by using the calculated physical index of the blood vessel of the subject, based on the correlation information;
identifying a pressure ratio in the blood vessel by performing the fluid analysis using the identified parameter and at least one of the calculated blood vessel morphology indices; and
displaying the identified pressure ratio in the blood vessel.

* * * * *